United States Patent
Kasai et al.

(10) Patent No.: US 8,308,995 B2
(45) Date of Patent: *Nov. 13, 2012

(54) CHROMENE COMPOUND

(75) Inventors: Soko Kasai, Shunan (JP); Shinobu Izumi, Shunan (JP)

(73) Assignee: Tokuyama Corporation, Shunan-Shi, Yamaguchi (JP)

(*) Notice: Subject to any disclaimer, the term of this patent is extended or adjusted under 35 U.S.C. 154(b) by 0 days.

This patent is subject to a terminal disclaimer.

(21) Appl. No.: 13/370,133

(22) Filed: Feb. 9, 2012

(65) Prior Publication Data

US 2012/0138876 A1 Jun. 7, 2012

Related U.S. Application Data

(62) Division of application No. 12/991,859, filed as application No. PCT/JP2009/059025 on May 8, 2009, now Pat. No. 8,147,726.

(30) Foreign Application Priority Data

May 9, 2008 (JP) .................................. 2008-123510
May 29, 2008 (JP) .................................. 2008-141128

(51) Int. Cl.
*G02B 5/23* (2006.01)
*C07D 311/78* (2006.01)
*C07D 311/94* (2006.01)

(52) U.S. Cl. ............... 252/586; 252/582; 428/411.1; 544/31; 544/79; 544/150; 546/167; 546/196; 549/24; 549/382; 549/388

(58) Field of Classification Search .......... 252/582, 252/586; 428/411.1; 544/31, 79, 150; 546/167, 546/196; 549/24, 382, 388
See application file for complete search history.

(56) References Cited

U.S. PATENT DOCUMENTS

| | | | |
|---|---|---|---|
| 5,698,141 A | 12/1997 | Kumar | |
| 5,723,072 A | 3/1998 | Kumar | |
| 6,296,785 B1 | 10/2001 | Nelson et al. | |
| 2003/0040623 A1 | 2/2003 | Mann et al. | |
| 2003/0092918 A1 | 5/2003 | Qin | |
| 2005/0092972 A1 | 5/2005 | Chan et al. | |
| 2007/0246692 A1* | 10/2007 | Melzig et al. | 252/586 |

FOREIGN PATENT DOCUMENTS

| | | |
|---|---|---|
| JP | 2000-504031 A | 4/2000 |
| JP | 2001-512434 A | 8/2001 |
| JP | 2003-513017 A | 4/2003 |
| JP | 2004-509109 A | 3/2004 |
| JP | 2007-516961 A | 6/2007 |
| JP | 2009-067680 | * 4/2009 |
| JP | 2009-67680 A | 4/2009 |
| JP | 2009-108159 A | 5/2009 |
| WO | WO 97/48993 A1 | 12/1997 |
| WO | WO 98/32037 A1 | 7/1998 |
| WO | WO 01/19813 A1 | 3/2001 |
| WO | WO 03/025638 A1 | 3/2003 |
| WO | WO 03/082849 A1 | 10/2003 |
| WO | WO 2005/047277 A1 | 5/2005 |
| WO | WO 2006/045495 A1 | 5/2006 |

OTHER PUBLICATIONS

European Search Report, dated Mar. 30, 2011, for Application No. 09742792.6.
International Preliminary Report on Patentability and Translation of Written Opinion of the International Searching Authority, dated Dec. 23, 2010, for International Application No. PCT/JP2009/059025 (Forms PCT/IB/338, PCT/IB/373 and PCT/ISA/237).
International Search Report, dated Jul. 21, 2009, for International Application No. PCT/JP2009/059025.
U.S. PTO Office Action, dated Apr. 20, 2011, for copending U.S. Appl. No. 12/991,859.
U.S. PTO Office Action, dated Aug. 26, 2011, for copending U.S. Appl. No. 12/991,859.

* cited by examiner

*Primary Examiner* — Bijan Ahvazi
(74) *Attorney, Agent, or Firm* — Birch, Stewart, Kolasch & Birch, LLP

(57) ABSTRACT

A chromene compound represented by the following formula (1):

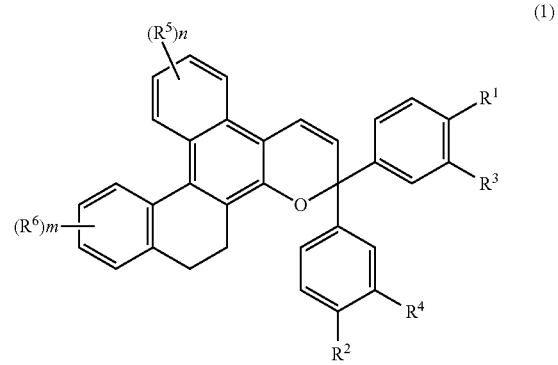

wherein $R^1$, $R^2$, $R^3$, $R^4$, $R^5$, $R^6$, m, and n are defined in the specification. The chromene compound is rarely deteriorated by exposure.

20 Claims, No Drawings

CHROMENE COMPOUND

This application is a Divisional of U.S. application Ser. No. 12/991,859, filed Nov. 9, 2010 now U.S. Pat. No. 8,147,726, which is a national phase under 35 U.S.C. §371 of PCT International Application No. PCT/JP2009/059025 which has an international filing date of May 8, 2009, which claims priority to Application No. 2008-141128, filed in Japan on May 29, 2008, and Application No. 2008-123510, filed in Japan on May 9, 2008. The entire contents of all of the above applications are hereby incorporated by reference.

TECHNICAL FIELD

The present invention relates to a novel chromene compound and its use.

BACKGROUND OF THE ART

Photochromism is the reversible function of a certain compound that it changes its color swiftly upon exposure to light including ultraviolet light such as sunlight or light from a mercury lamp and returns to its original color when it is put in the dark by stopping its exposure to light. A compound having this property is called "photochromic compound" and used as a material for photochromic plastic lenses.

For the photochromic compound used for this purpose, the following properties are required: (I) the degree of coloration at a visible light range before ultraviolet light is applied (initial coloration) should be low, (II) the degree of coloration upon exposure to ultraviolet light (to be referred to as "color optical density" hereinafter) should be high, (III) the speed from the time when the application of ultraviolet light is started to the time when the color optical density reaches saturation should be high (to be also referred to as "high color development sensitivity" hereinafter), (IV) the speed from the stoppage of the application of ultraviolet light to the time when the compound returns to its original state (to be referred to as "fading speed" hereinafter) should be high, (V) the repeat durability of this reversible function should be high, and (VI) the solubility in a monomer composition as a host material of the photochromic compound should be high so that its dispersibility in the host material in use becomes high when it is cured.

To meet the above requirements, a wide variety of photochromic compounds have been synthesized. Since a chromene compound in particular has high durability and high sensitivity to ultraviolet light, a large number of researches have been made on the chromene compound.

To use the above photochromic compound in a photochromic plastic lens, the following manufacturing methods are known: one in which a polymer film containing a photochromic compound dispersed uniformly therein is sandwiched between lenses to manufacture a photochromic plastic lens, one in which a photochromic compound is dispersed in a polymerizable monomer and then the monomer is polymerized by a predetermined technique to obtain a photochromic plastic lens, one in which a photochromic compound is dissolved in, for example, silicone oil to impregnate its surface with the silicone oil at 150 to 200° C. for 10 to 60 minutes and the surface is further covered with a curable material to obtain a photochromic plastic lens, one in which the above polymer film is formed on the surface of a lens and the surface is covered with a curable material to obtain a photochromic plastic lens, and one in which a coating agent comprising a photochromic curable composition containing a photochromic compound and a polymerizable monomer (to be simply referred to as "coating agent containing a photochromic compound" hereinafter) is applied to the surface of a lens substrate and cured to obtain a photochromic plastic lens.

Out of the above methods of manufacturing a photochromic plastic lens, one in which a coating agent containing a photochromic compound is applied to the surface of a lens substrate and cured by photopolymerization is excellent because the most use is made of the characteristic properties of the lens substrate and excellent photochromic properties are obtained.

However, when the inventors of the present invention prepared various coating agents comprising a photochromic compound and cured the obtained coating films by photopolymerization, they found that, though the initial coloration of a coating agent containing a certain photochromic compound is little, the photochromic compound deteriorates by light during photopolymerization, the coating film may yellow, and further its photochromic properties deteriorate after that. Particularly chromene compounds which develop a yellow color (may be referred to as "yellow compounds" hereinafter) are used for color control and other purposes but have the following problems.

For example, they found that a coating film formed by applying a coating agent containing a chromene compound represented by the following formula (A) (refer to WO06/045495) yellows after photopolymerization and deteriorates in durability though its initial coloration is little.

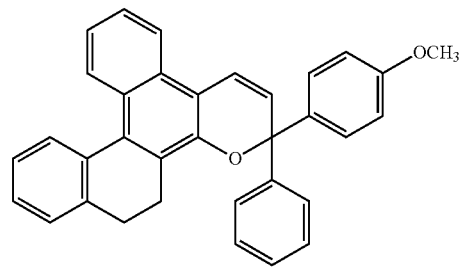

(A)

Further, although a coating film formed by applying a coating agent containing a chromene compound represented by the following formula (B) (refer to WO03/082849) rarely experiences initial coloration and does not yellow after photopolymerization, its color optical density is low and its fading speed is too high. Further, its developed color is orange, and it is desired that its absorption wavelength should be made short to use it as a yellow compound.

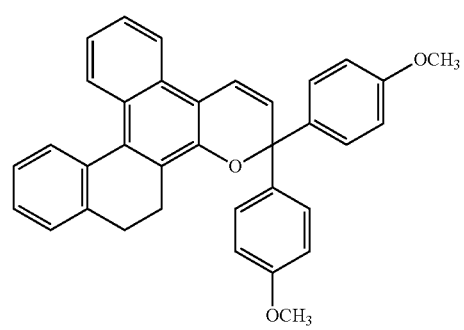

(B)

Although a coating film formed by applying a coating agent containing a chromene compound represented by the following formula (C) has a high color optical density and a moderate fading speed, its initial coloration is marked. When a photochromic plastic lens is manufactured by using this chromene compound, the transmittance of the photochromic plastic lens before exposure to ultraviolet light becomes low.

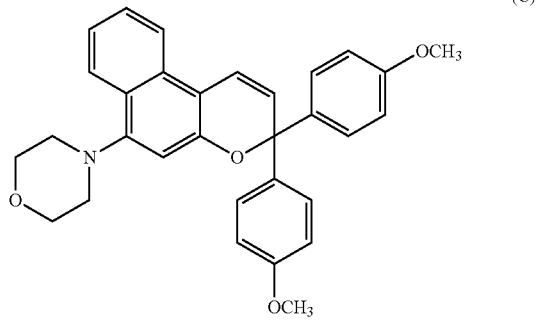

(C)

DISCLOSURE OF THE INVENTION

It is an object of the present invention to provide a chromene compound which can be highly dispersed in a polymerizable monomer and is capable of preventing the yellowing of a curable composition containing the chromene compound even when it is cured by exposure to an energy ray such as ultraviolet radiation and of providing a cured product having excellent photochromic properties such as weak initial coloration, a high color optical density and a practical fading speed.

It is another object of the present invention to provide a chromene composition which comprises the above chromene compound of the present invention and another chromene compound so as to develop a color which cannot be developed only by the chromene compound of the present invention.

It is still another object of the present invention to provide a photochromic curable composition comprising the chromene compound of the present invention or the above chromene composition as well as a photochromic optical product.

Other objects and advantages of the present invention will become apparent from the following description.

According to the present invention, firstly, the above objects and advantages of the present invention are attained by a chromene compound represented by the following formula (1):

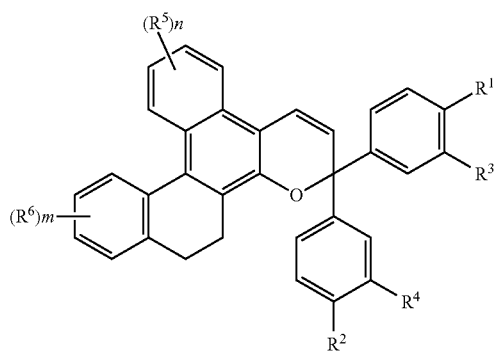

(1)

wherein $R^1$ and $R^2$ are each independently an alkyl group having 1 to 9 carbon atoms, cycloalkyl group having 3 to 12 carbon atoms, perfluoroalkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms or alkoxy group having 1 to 6 carbon atoms, with the proviso that $R^1$ and $R^2$ cannot be alkoxy groups having 1 to 6 carbon atoms at the same time;

$R^3$ and $R^4$ are each independently a hydrogen atom, hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms or aryloxy group having 6 to 10 carbon atoms;

$R^1$ and $R^3$ or $R^2$ and $R^4$ may be bonded together to form an alkylene group or alkylenedioxy group;

$R^5$ and $R^6$ are each independently a hydroxy group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, cyano group, nitro group, halogen atom, halogenoalkyl group having 1 to 6 carbon atoms or halogenoalkoxy group having 1 to 6 carbon atoms, and m and n are each independently an integer of 0 to 4.

According to the present invention, secondly, the above objects and advantages of the present invention are attained by a chromene composition comprising a chromene compound represented by the above formula (1) and a chromene compound having an absorbance due to thermochromism of 0.1 or less and the absorption end of its ultraviolet absorption spectrum at 380 to 430 nm.

The chromene composition comprising a chromene compound having an absorbance due to thermochromism of 0.1 or less and the absorption end of its ultraviolet absorption spectrum at 380 to 430 nm is preferably a chromene composition comprising a chromene compound represented by the following formula (2).

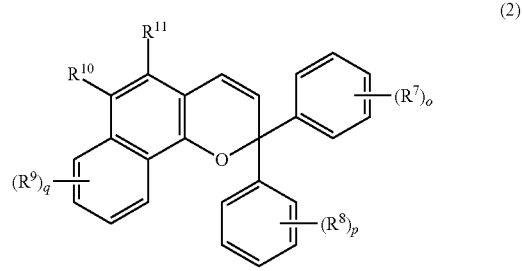

(2)

In the above formula, $R^7$ and $R^8$ are each an alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring, or halogen atom, o and p are each an integer of 0 to 2, with the proviso that when o and p are each an integer of 1 to 2, $R^7$ and $R^8$, two $R^7$'s and two $R^8$'s may be the same or different;

$R^9$ is an alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, amino group, heterocyclic group having a nitrogen atom as a hetero atom and bonded to a benzene ring by the nitrogen atom bonded to the benzene ring, or halogen atom, and q is an integer of 0 to 2;

when q is 2, the both substituents may be bonded together to form an alkylenedioxy group having 1 to 8 carbon atoms;

$R^{10}$ and $R^{11}$ are each a hydrogen atom, hydroxy group, alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, acyloxy group having 2 to 7 carbon atoms (the number of carbon atoms includes the number of carbonyl carbon atoms, the number of carbon atoms of the acyloxy group shall include the number of carbonyl carbon atoms), alkoxycarbonyl group having 2 to 7 carbon atoms (the number of carbon atoms includes the number of carbonyl carbon atoms, the number of carbon atoms of the alkoxycarbonyl group shall include the number of carbonyl carbon atoms), formyl group, carboxyl group, amino group, heterocyclic group having a nitrogen atom as a hetero atom and bonded to a benzene ring by the nitrogen atom bonded to the benzene ring, amide group, halogen atom, halogenoalkyl group having 1 to 6 carbon atoms or halogenoalkoxy group having 1 to 6 carbon atoms;

$R^{10}$ and $R^{11}$ may be bonded together to form a group represented by the following formula (3):

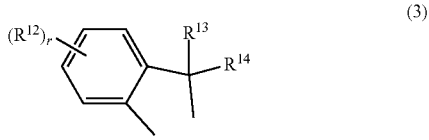

(3)

wherein $R^{12}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and r is an integer of 0 to 3;

$R^{13}$ and $R^{14}$ are each a hydrogen atom, hydroxyl group, alkyl group having 1 to 9 carbon atoms, cycloalkyl group having 3 to 12 carbon atoms, alkoxy group having 1 to 6 carbon atoms, halogenoalkyl group having 1 to 6 carbon atoms or halogenoalkoxy group having 1 to 6 carbon atoms, and further $R^{13}$ and $R^{14}$ may be bonded together to form a cyclic structure;

further $R^{10}$ and $R^{11}$ may be bonded together to form a group represented by the following formula (4):

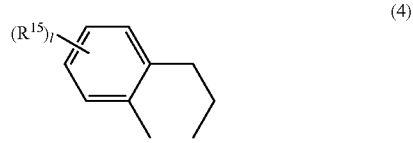

(4)

wherein $R^{15}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and l is an integer of 0 to 3.

According to the present invention, thirdly, the above objects and advantages of the present invention are attained by a photochromic curable composition comprising the above chromene compound or chromene composition and polymerizable monomers.

The content of the above chromene compound or chromene composition is preferably 0.001 to 10 parts by mass based on 100 parts by mass of the polymerizable monomers. The above photochromic curable composition preferably contains a photopolymerization initiator and/or a thermopolymerization initiator.

According to the present invention, in the fourth place, the above objects and advantages of the present invention are attained by a photochromic material containing a polymer material and the above chromene compound or chromene composition dispersed in the polymer material.

According to the present invention, in the fifth place, the above objects and advantages of the present invention are attained by a photochromic optical product which comprises a polymer molded product containing the above chromene compound or chromene composition dispersed therein.

According to the present invention, in the sixth place, the above objects and advantages of the present invention are attained by an optical product which comprises an optical substrate covered with a polymer film containing the above chromene compound or chromene composition dispersed therein.

The above polymer film is preferably a film formed by curing the above photochromic curable composition by optical radical polymerization.

BEST MODE FOR CARRYING OUT THE INVENTION

The chromene compound of the present invention is represented by the following formula (1).

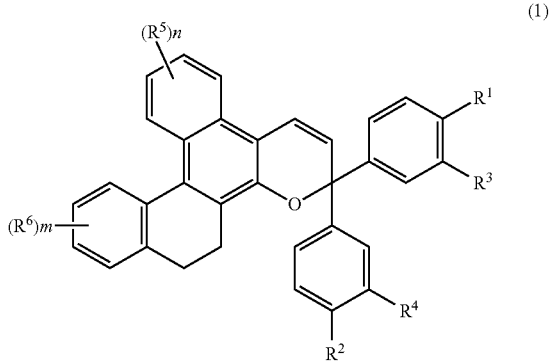

(1)

(Groups $R^1$ and $R^2$)

In the above formula (1), $R^1$ and $R^2$ are each independently an alkyl group having 1 to 9 carbon atoms, cycloalkyl group having 3 to 12 carbon atoms, perfluoroalkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms or alkoxy group having 1 to 6 carbon atoms, with the proviso that $R^1$ and $R^2$ cannot be alkoxy groups having 1 to 6 carbon atoms at the same time.

Examples of the alkyl group having 1 to 9 carbon atoms include methyl group, ethyl group, n-propyl group, isopropyl group, n-butyl group, sec-butyl group, tert-butyl group, pentyl group, hexyl group, heptyl group and octyl group.

Examples of the cycloalkyl group having 3 to 12 carbon atoms include cyclopropyl group, cyclobutyl group, cyclopentyl group, cyclohexyl group, cycloheptyl group and cyclooctyl group.

Examples of the perfluoroalkoxy group having 1 to 6 carbon atoms include trifluoromethoxy group, perfluoroethoxy group, perfluoropropoxy group, perfluorobutoxy group and perfluorohexyloxy group.

Examples of the aralkyl group having 7 to 11 carbon atoms include benzyl group, phenylethyl group, phenylpropyl group, phenylbutyl group and naphthylmethyl group.

Examples of the aralkoxy group having 7 to 11 carbon atoms include benzyloxy group and naphthylmethoxy group.

Examples of the aryl group having 6 to 10 carbon atoms include phenyl group and naphthyl group. Substituted aryl groups formed by substituting one or more hydrogen atoms of the aryl group by the same alkyl group, cycloalkyl group, aralkyl group or aralkoxy group as described above and aryloxy group or alkoxy group which will be described hereinafter may also be preferably used.

Examples of the aryloxy group having 6 to 10 carbon atoms include phenoxy group and naphthoxy group.

Examples of the alkoxy group having 1 to 6 carbon atoms include methoxy group, ethoxy group, n-propoxy group, isopropoxy group, n-butoxy group, sec-butoxy group and tert-butoxy group. $R^1$ and $R^2$ can be alkoxy groups as listed above but one of them must be a group except for the alkoxy group. If both $R^1$ and $R^2$ are alkoxy groups, when a photochromic composition comprising polymerizable monomers and a chromene compound is cured by photopolymerization, the color optical density of the obtained cured product becomes low and the fading speed becomes too high disadvantageously.

In the present invention, to obtain a chromene compound having high photopolymerization resistance and high photochromic durability, the groups $R^1$ and $R^2$ are each preferably an electron donating group. The electron donating group is preferably a substituent based on Hammett's rule, such as alkoxy group, aralkoxy group, cycloalkyl group, alkyl group or perfluoroalkoxy group. The alkyl group and the alkoxy group are particularly preferred because they are easily acquired industrially. Specific preferred examples of the substituent include methyl group, ethyl group and methoxy group. A preferred combination of $R^1$ and $R^2$ is a combination of an alkyl group and an alkoxy group or a combination of an alkyl group and an alkyl group.

(Groups $R^3$ and $R^4$)

$R^3$ and $R^4$ are each independently a hydrogen atom, hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms or aryloxy group having 6 to 10 carbon atoms.

Preferred examples of the alkyl group, cycloalkyl group, alkoxy group, aralkyl group, aralkoxy group, aryl group and aryloxy group are the same as those enumerated for $R^1$ and $R^2$.

In the present invention, in a chromene compound which has a particularly excellent effect, $R^3$ is a hydrogen atom or alkylene group, or $R^4$ is a hydrogen atom or bonded with $R^2$ to form an alkylenedioxy group which will be described hereinbelow.

(Group Formed by Bonding Together $R^1$ and $R^3$ or $R^2$ and $R^4$)

$R^1$ and $R^3$ or $R^2$ and $R^4$ may be bonded together to form an alkylene group or alkylenedioxy group. That is, $R^1$ and $R^3$ or $R^2$ and $R^4$ may be bonded together to form a ring including the carbon atoms of a benzene ring bonded to $R^1$ and $R^3$ or $R^2$ and $R^4$. In a chromene compound which has a particularly excellent effect, $R^2$ and $R^4$ are bonded together to form an alkylene group or alkylenedioxy group.

The alkylene group is preferably an alkylene group having 1 to 8 carbon atoms. That is, the number of carbon atoms of the formed ring including carbon atoms bonded to $R^1$ and $R^3$ or $R^2$ and $R^4$ is preferably 3 to 10. Further, an aromatic hydrocarbon ring such as benzene or naphthalene may be condensed to the ring. The ring may have an alkyl group or alkoxy group having 1 to 5 carbon atoms as a substituent.

The alkylenedioxy group is preferably an alkylenedioxy group having 1 to 8 carbon atoms. That is, the number of carbon atoms of the formed ring including carbon atoms bonded to $R^1$ and $R^3$ or $R^2$ and $R^4$ is preferably 3 to 10. Further, an aromatic hydrocarbon ring such as benzene or naphthalene may be condensed to the ring. The ring may have an alkyl group or alkoxy group having 1 to 5 carbon atoms as a substituent.

Particularly preferred examples of the alkylene group or alkylenedioxy group include the following rings.

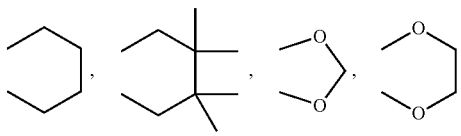

In the present invention, when $R^1$ and $R^3$ or $R^2$ and $R^4$ are bonded together to form a ring, as the chromene compound has high photopolymerization resistance and high photochromic durability, the ring is preferably an electron donating group. The electron donating group is preferably a substituent based on Hammett's rule, such as an alkylenedioxy group. A methylenedioxy group is particularly preferred because it is easily acquired industrially.

(Groups $R^5$ and $R^6$)

In the above formula (1), $R^5$ and $R^6$ are each independently a hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, cyano group, nitro group, halogen atom, halogenoalkyl group having 1 to 6 carbon atoms or halogenoalkoxy group having 1 to 6 carbon atoms.

Preferred examples of the alkyl group, cycloalkyl group, alkoxy group, aralkyl group, aralkoxy group, aryl group and aryloxy group are the same as those enumerated for $R^1$ to $R^4$.

Examples of the halogen atom are fluorine atom, chlorine atom, bromine atom and iodine atom.

The halogenoalkyl group is obtained by substituting one or more hydrogen atoms of the above alkyl group by a fluorine atom, chlorine atom or bromine atom. Specific examples of the halogenoalkyl group include fluoromethyl group, chloromethyl group, bromomethyl group, difluoromethyl group, dichloromethyl group, dibromomethyl group, trifluoromethyl group, trichloromethyl group and tribromomethyl group. Out of these, halogenoalkyl groups obtained by substitution with a fluorine atom are preferred. Preferred examples of the halogenoalkyl group include fluoromethyl group, difluoromethyl group and trifluoromethyl group.

The halogenoalkoxy group is obtained by substituting one or more hydrogen atoms of the above alkoxy group by a fluorine atom, chlorine atom or bromine atom.

Specific examples of the halogenoalkoxy group include fluoromethoxy group, chloromethoxy group, bromomethoxy group, difluoromethoxy group, dichloromethoxy group, dibromomethoxy group, trifluoromethoxy group, trichloromethoxy group and tribromomethoxy group. Out of these, halogenoalkoxy groups obtained by substitution with a fluorine atom are preferred. Particularly preferred examples of the halogenoalkoxy group include fluoromethoxy group, difluoromethoxy group and trifluoromethoxy group.

(n and m)

In the above formula (1), n indicates the number of substituents of $R^5$ and is an integer of 0 to 4. m indicates the number of substituents of $R^6$ and is an integer of 0 to 4. n is preferably an integer of 0 to 1 and m is preferably an integer of 0 to 1 because the obtained chromene compound is easily produced and shows excellent photochromic properties.

(Preferred Chromene Compound)

Particularly preferred examples of the chromene compound in the present invention include the following compounds.

<1> 2,2-bis(4-methylphenyl)-13,14-dihydronaphtho[1,2-h]-benzo[f]-chromene

<2> 2-(4-methylphenyl),2-(4-methoxyphenyl)-13,14-dihydronaphtho[1,2-h]-benzo[f]-chromene <3> 2-(3,4-dimethylphenyl),2-(4-methylphenyl)-13,14-dihydronaphtho[1,2-h]-benzo[f]-chromene <4> 2-(4-methylphenyl),2-(3-methyl-4-methoxyphenyl)-13,14-dihydronaphtho[1,2-h]-benzo[f]-chromene <5> 2-(4-cyclohexylphenyl),2-(4-methylphenyl)-13,14-dihydronaphtho[1,2-h]-benzo[f]-chromene <6> 2-(4-cyclohexylphenyl),2-(4-methoxyphenyl)-13,14-dihydronaphtho[1,2-h]-benzo[f]-chromene <7> 2-(3,4-methylenedioxyphenyl),2-(4-methoxyphenyl)-13,14-dihydronaphtho[1,2-h]-benzo[f]-chromene <8> 2-(3,4-methylenedioxyphenyl),2-(4-methylphenyl)-13,14-dihydronaphtho[1,2-h]-benzo[f]-chromene <9> 2-(4-methylphenyl),2-(4-trifluoromethoxyphenyl)-13,14-dihydronaphtho[1,2-h]-benzo[f]-chromene <10> 2-(4-biphenyl),2-(4-methylphenyl)-13,14-dihydronaphtho[1,2-h]-benzo[f]-chromene <11> 2-(3,4-dimethylphenyl),2-(4-methylphenyl)-6-methoxy-13,14-dihydronaphtho[1,2-h]-benzo[f]-chromene <12> 2-(3,4-dimethoxyphenyl),2-(4-methylphenyl)-6-methoxy-13,14-dihydronaphtho[1,2-h]-benzo[f]-chromene The structural formulas of the above chromene compounds and other preferred chromene compounds are given below.

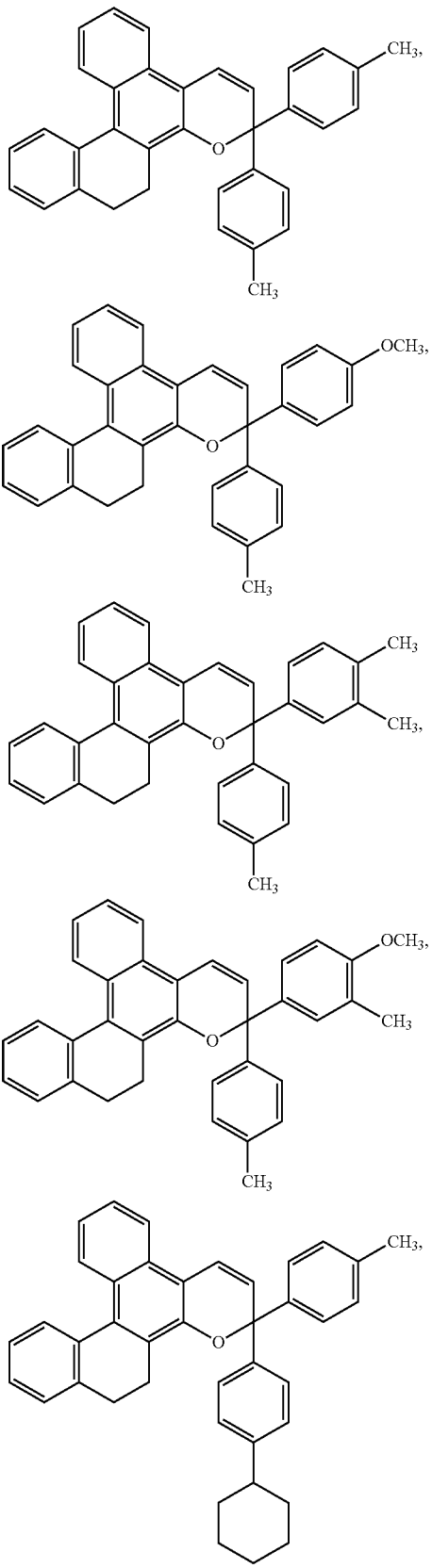

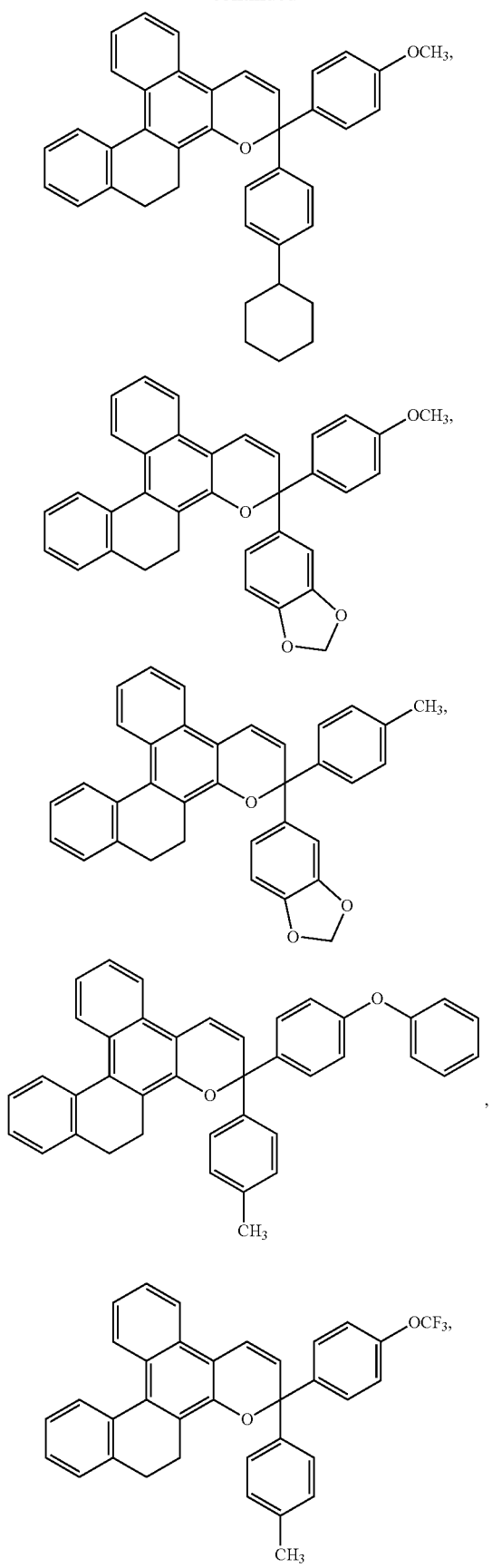

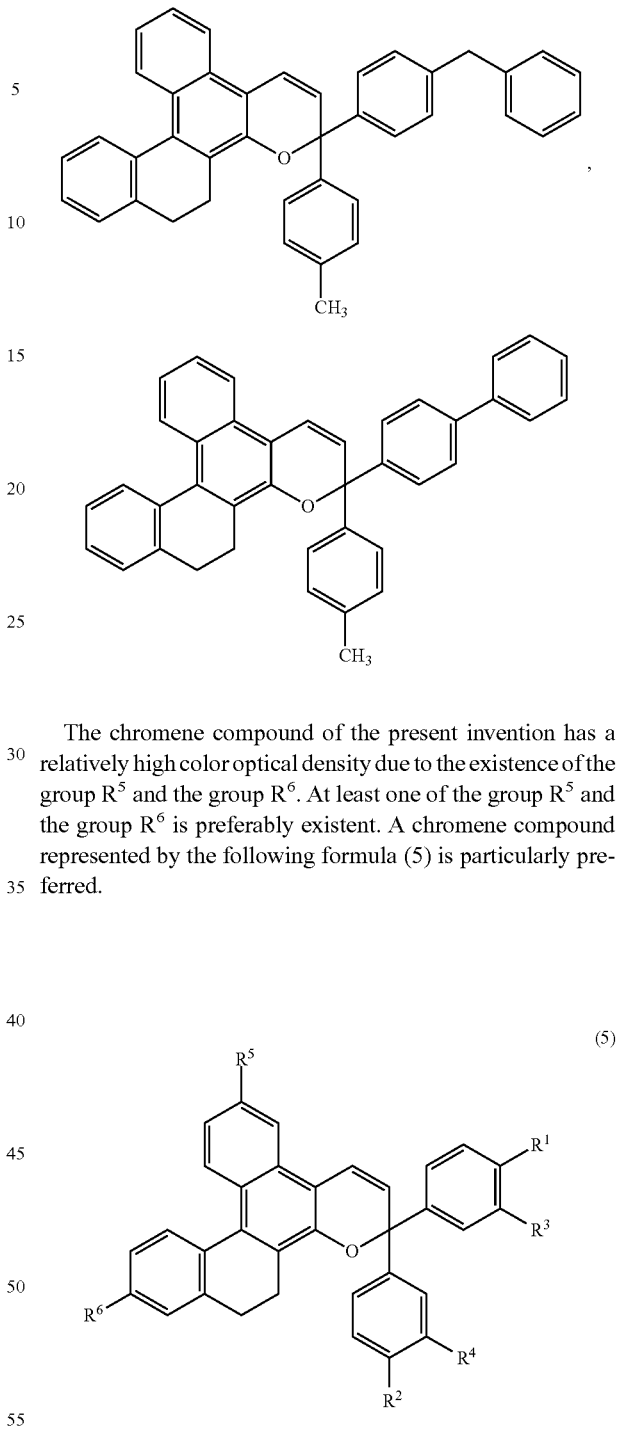

The chromene compound of the present invention has a relatively high color optical density due to the existence of the group $R^5$ and the group $R^6$. At least one of the group $R^5$ and the group $R^6$ is preferably existent. A chromene compound represented by the following formula (5) is particularly preferred.

(5)

In the above formula, $R^1$, $R^2$, $R^3$, $R^4$, $R^5$ and $R^6$ are as defined in the above formula (1). In the above formula (5), $R^5$ and $R^6$ are each preferably an electron donating group, more specifically an alkoxy group or alkyl group explained for the above group $R^1$. In the above formula (5), either one of $R^5$ and $R^6$ may be a hydrogen atom (in the above formula (1), this corresponds to a case where either one of n and m is 0). Preferred examples of the chromene compound represented by the above formula (5) are given below.

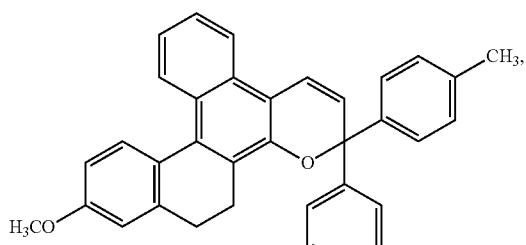

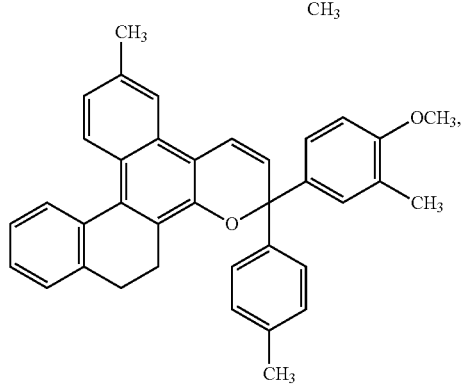

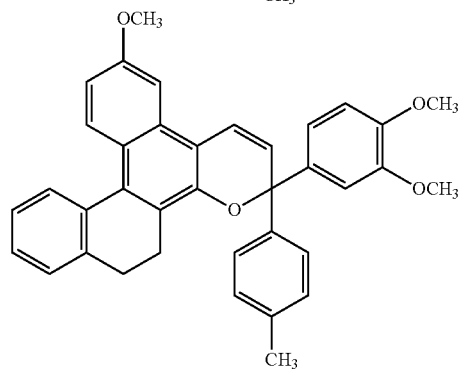

(Identification of Chromene Compound)

The chromene compound of the present invention is existent as an achromatic or light yellow solid or viscous liquid at normal temperature and normal pressure and can be confirmed by the following means (i) to (iii).

(i) Peaks based on an aromatic proton and the proton of an alkene appear at δ of around 5.0 to 9.0 ppm and peaks based on the protons of an alkyl group and an alkylene group appear at δ of around 0.5 to 4.0 ppm when the proton nuclear magnetic resonance spectrum ($^1$H-NMR) of the chromene compound is measured. The number of protons of the bonded groups can be known by comparing the spectral intensities of the peaks relatively.

(ii) The composition of the corresponding product can be determined by elemental analysis.

(iii) A peak based on the carbon of an aromatic hydrocarbon group appears at δ of around 110 to 160 ppm, peaks based on the carbons of an alkene and an alkyne appear at δ of around 80 to 140 ppm, and peaks based on the carbons of an alkyl group and an alkylene group appear at δ of around 10 to 80 ppm.

(Process of Producing Chromene Compound)

The process of producing the chromene compound represented by the formula (1) of the present invention is not particularly limited, and the chromene compound may be obtained by any synthesis process. A typical process which is preferably employed is described below.

The chromene compound represented by the above formula (1) can be produced by reacting a naphthol derivative represented by the following formula (6) with a propargyl alcohol derivative represented by the following formula (7) in the presence of an acid catalyst:

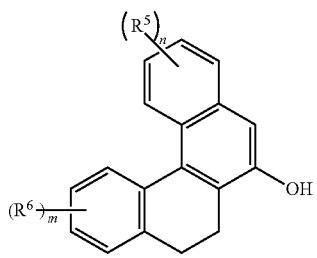

(6)

wherein, $R^5$, $R^6$, m and n are as defined in the above formula (1),

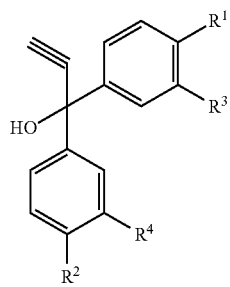

(7)

wherein $R^1$, $R^2$, $R^3$ and $R^4$ are as defined in the above formula (1).

The naphthol derivative represented by the above formula (6) can be synthesized in accordance with a reaction method described in research papers such as Tetrahedoron Lett. 24(50), 5571-5574, 1983, Bioorg. Med. Chem. Lett. 12(11), 1457-1461, 2002, and Tetrahedron 53 (48), 16575-16596, 1997. Specific reaction formulae are given below.

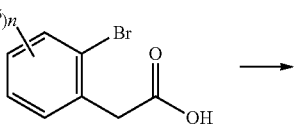

(a)

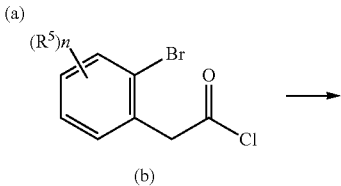

(b)

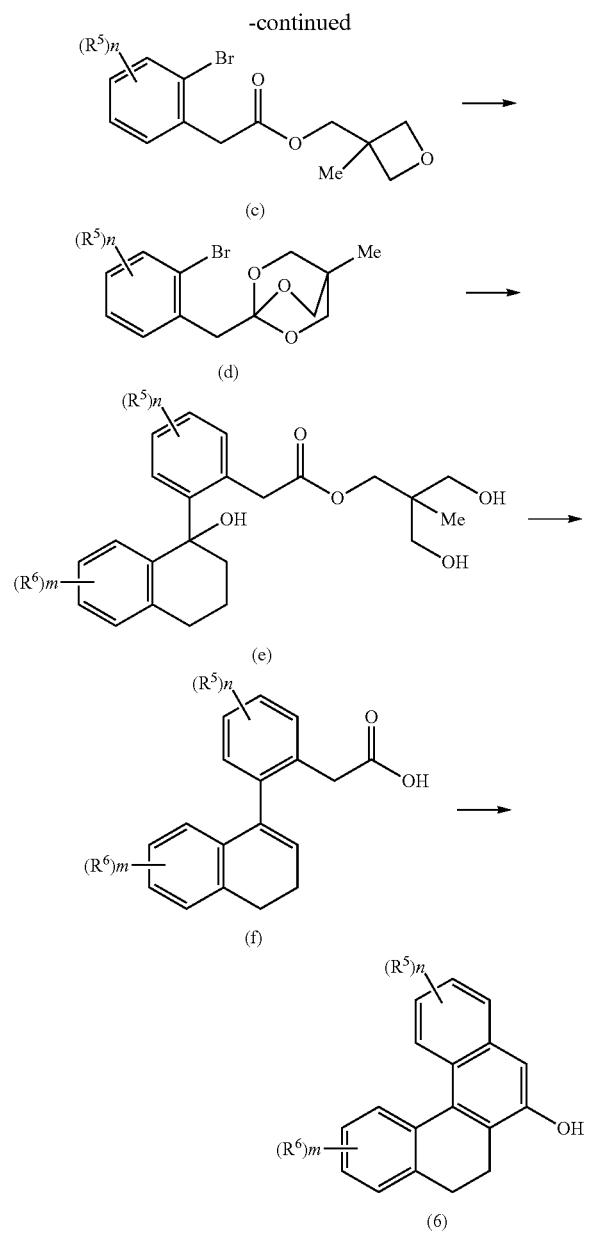

The reaction between the compound represented by the above formula (6) and the compound represented by the above formula (7) in the presence of an acid catalyst is carried out as follows. That is, the reaction ratio of these two compounds is selected from a wide range, preferably 1:10 to 10:1 (molar ratio).

The acid catalyst is preferably selected from sulfuric acid, benzenesulfonic acid, p-toluenesulfonic acid and acidic alumina. The acid catalyst is used in an amount of preferably 0.1 to 10 parts by mass based on the total of the compound represented by the above formula (6) and the compound (reactive substrate) represented by the above formula (7). The reaction temperature is preferably 0 to 200° C., and the solvent is an aprotic organic solvent such as N-methylpyrrolidone, dimethyl formamide, tetrahydrofuran, benzene or toluene.

The method of purifying the product is not particularly limited. For example, the product can be purified with a silica gel column and further by recrystallization.

(Characteristic Properties of Chromene Compound)

The chromene compound of the present invention dissolves well in a general-purpose organic solvent such as toluene, chloroform or tetrahydrofuran. When the chromene compound represented by the above formula (1) is dissolved in the above solvent, the obtained solution is almost achromatic and transparent and has an excellent photochromic function that it develops a color swiftly upon exposure to sunlight or ultraviolet radiation and reversibly returns to its original achromatic state swiftly by blocking off the light. Since the chromene compound of the present invention very rarely experiences initial coloration and is transparent though it is a yellow compound, it is easy to control color by mixing it with another photochromic compound (chromene compound) different from the chromene compound of the present invention, and initial coloration can be greatly reduced even in the prepared photochromic composition.

Another object of the present invention is to provide a photochromic composition which rarely experiences initial coloration. Since the photochromic compound of the present invention develops a yellow to orange color, it must be combined with another photochromic compound to develop another color. Any known compound may be used in combination as the photochromic compound to be combined with. Examples of the photochromic compound to be combined with include fulgide, fulgimide, spirooxazine and chromene. Out of these, spirooxazine and chromene compounds are preferred when photopolymerization resistance and photochromic durability are taken into consideration. Further, chromene compounds are the most preferred when the reduction of initial coloration is taken into consideration.

That is, still another object of the present invention is to provide a photochromic composition (may be referred to as "chromene composition" hereinafter) comprising the chromene compound of the present invention and another chromene compound which rarely experiences initial coloration and providing high transparency.

The term "initial coloration" is connected with two properties of the chromene compound. One of them is initial coloration due to thermochromism and indicates the absorbance of the chromene compound under no exposure to ultraviolet radiation at room temperature. For example, when the composition is used in an optical material such as a spectacle lens and this value is smaller, the composition provides higher transparency at room temperature. The other is coloration when the ultraviolet absorption spectrum of the chromene compound reaches the visible range. As the terminal portion (absorption end) of the ultraviolet absorption spectrum of the Specific conditions for the above reaction will be described hereinbelow. A bromophenylacetic acid derivative (a) as a raw material is changed into an acid chloride (b) by a predetermined method, and this acid chloride (b) is reacted with 3-methyl-3-oxetane methanol in the presence of pyridine in dichloromethane to obtain an ester form (c). Lewis acid is caused to act on the ester form (c) to form an orthoester form (d), and a Grignard reagent for the orthoester form (d) is prepared and then reacted with α-tetralone to obtain an alcohol form (e). This alcohol form (e) is treated with hydrochloric acid to carry out the hydrolysis of the ester in an alkali aqueous solution to obtain a carboxylic acid (f). Subsequently, polyphosphoric acid is caused to act on the carboxylic acid (f) in a toluene solvent to cyclize it, thereby making it possible to obtain the naphthol derivative represented by the above formula (6).

The propargyl alcohol derivative represented by the above formula (7) can be synthesized, for example, by reacting a ketone derivative corresponding to the above formula (7) with a metal acetylene compound such as lithium acetylide.

chromene compound reaches the visible range, the chromene compound is tinged with yellow under no exposure to ultraviolet radiation. Since a plastic lens tinged with yellow is not preferred, to provide a photochromic lens rarely tinged with yellow, it is preferred that the absorption end of the ultraviolet absorption spectrum of the chromene compound should not reach deep the visible range.

(Another Chromene Compound to be Combined with)

Preferably, the another chromene compound to be combined with has an absorbance due to thermochromism of 0.1 or less and the absorption end of its ultraviolet absorption spectrum at 380 to 430 nm because it provides transparency. The absorbance due to thermochromism and the absorption end of the ultraviolet absorption spectrum are values measured by the methods described in the following examples.

To develop a gray or brown color and achieve excellent photochromic properties, another chromene compound represented by the following formula (2) is preferably used in combination. Further, a chromene compound having an absorbance due to thermochromism of 0.03 or less and the absorption end at 380 to 410 nm is particularly preferred to provide high transparency.

Further, as the fading half period of the chromene compound of the present invention can be set to 25 to 120 seconds in a polymer solid matrix which will be described hereinafter, when uniform color at the time of fading in the case of a mixture with another chromene compound is taken into consideration, the another chromene compound to be combined with also preferably has a fading half period of 25 to 120 seconds in the above polymer solid matrix.

A preferred example of the another chromene compound is a chromene compound represented by the following formula (2).

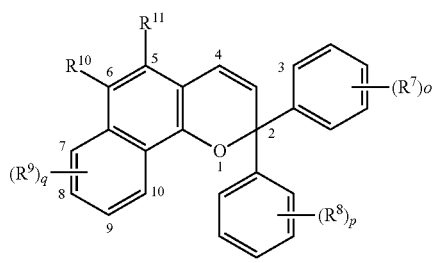

(2)

(Groups $R^7$ and $R^8$)

In the above formula (2), $R^7$ and $R^8$ are each an alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring, or halogen atom, and o and p are each an integer of 0 to 2, with the proviso that when o and p are each an integer of 1 to 2, $R^7$ and $R^8$, two $R^7$'s and two $R^8$'s may be the same or different.

Preferred examples of the alkyl group having 1 to 9 carbon atoms include methyl group, ethyl group, n-propyl group, isopropyl group, n-butyl group, sec-butyl group, tert-butyl group, pentyl group, hexyl group, heptyl group and octyl group.

Preferred examples of the alkoxy group having 1 to 6 carbon atoms include methoxy group, ethoxy group, n-propoxy group, isopropoxy group, n-butoxy group, sec-butoxy group and tert-butoxy group.

Examples of the aryl group having 6 to 10 carbon atoms include phenyl group and naphthyl group. The aryl group may have a substituent, and the aryl group having a substituent is obtained by substituting at least one hydrogen atom of the aryl group by an alkyl group having 1 to 9 carbon atoms, alkoxy group having 1 to 6 carbon atoms, aralkoxy group having 7 to 11 carbon atoms, amino group, halogen atom, aralkyl group having 6 to 10 carbon atoms or aryl group having 6 to 10 carbon atoms.

The amino group may be either one of primary amino group, and secondary amino group and tertiary amino group having a substituent. The typical substituent of the amino group is alkyl group or aryl group. Preferred examples of the substituted amino group (secondary amino group or tertiary amino group) include alkylamino groups such as methylamino group and ethylamino group; dialkylamino groups such as dimethylamino group and diethylamino group; arylamino groups such as phenylamino group; and diarylamino groups such as diphenylamino group.

Examples of the heterocyclic group having a nitrogen atom as a hetero atom and bonded to a benzene ring by the nitrogen atom bonded to the benzene ring include morpholino group, piperidino group, pyrrolidinyl group, piperazino group, N-methylpiperazino group and indolinyl group. Further, the heterocyclic group may have an alkyl group such as methyl group as a substituent. Examples of the heterocyclic group having a substituent include 2,6-dimethylmorpholino group, 2,6-dimethylpiperidino group and 2,2,6,6-tetramethylpiperidino group. When the performance of the finally obtained chromene compound is taken into consideration, morpholino group and piperidino group are preferred.

Examples of the halogen atom are fluorine atom, chlorine atom, bromine atom and iodine atom.

(Group $R^9$)

$R^9$ is an alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, amino group, heterocyclic group having a nitrogen atom as a hetero atom and bonded to a benzene ring (basic skeleton) by the nitrogen atom bonded to the benzene ring, or halogen atom, and q is an integer of 0 to 2. Preferably, $R^9$ has an electron donating group, specifically alkoxy group having 1 to 6 carbon atoms, amino group or heterocyclic group having a nitrogen atom as a hetero atom and bonded to a benzene ring by the nitrogen atom bonded to the benzene ring at the 8-position from the effect of positioning the absorption end of the ultraviolet absorption spectrum at a short wavelength range.

The above alkyl group, cycloalkyl group, alkoxy group, aryl group having 6 to 10 carbon atoms, aryloxy group having 6 to 10 carbon atoms, amino group, heterocyclic group having a nitrogen atom as a hetero atom and bonded to a benzene ring by the nitrogen atom bonded to the benzene ring and halogen atom are not particularly limited and include the same substituents as those enumerated for the groups $R^7$ and $R^8$ in the above formula (2).

Further, when the positioning of the absorption end at a short wavelength range is taken into consideration, it is preferred that $R^9$ should have an alkoxy group, amino group or heterocyclic group having a nitrogen atom as a hetero atom and bonded to a benzene ring (basic skeleton) by the nitrogen atom bonded to the benzene ring, specifically methoxy group, ethoxy group, morpholino group or dimethylamino group, at the 8-position. Further, when the improvement of the fading speed is taken into consideration, it is preferred that $R^9$ should form an alkylenedioxy group having 1 to 8 carbon atoms at the 8- and 9-positions, advantageously methylenedioxy group from the viewpoint of easy acquisition from the industrial field.

(Groups $R^{10}$ and $R^{11}$)

$R^{10}$ and $R^{11}$ are each a hydrogen atom, hydroxy group, alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, acyloxy group having 1 to 7 carbon atoms, alkoxycarbonyl group having 2 to 7 carbon atoms, formyl group, carboxyl group, amino group, heterocyclic group having a nitrogen atom as a hetero atom and bonded to a benzene ring by the nitrogen atom bonded to the benzene ring, amide group, halogen atom, halogenoalkyl group having 1 to 6 carbon atoms or halogenoalkoxy group having 1 to 6 carbon atoms Examples of the alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring and halogen atom are not particularly limited and are the same groups as those enumerated for the groups $R^7$ and $R^8$ in the above formula (2).

Examples of the cycloalkyl group having 3 to 12 carbon atoms include cyclopropyl group, cyclobutyl group, cyclopentyl group, cyclohexyl group, cycloheptyl group and cyclooctyl group.

Examples of the aryloxy group having 6 to 10 carbon atoms include phenoxy group and naphthoxy group. The aryloxy group may have a substituent, and the aryloxy group having a substituent is obtained by substituting one or more hydrogen atoms of the above aryloxy group by an alkyl group having 1 to 9 carbon atoms, alkoxy group having 1 to 6 carbon atoms, aralkoxy group having 6 to 11 carbon atoms, aralkyl group having 7 to 11 carbon atoms, aryl group having 6 to 10 carbon atoms, amino group or halogen atom.

Examples of the acyloxy group having 2 to 7 carbon atoms include acetoxy group, propionyloxy group, butyryloxy group, isobutyryloxy group, valeryloxy group, hexanoyloxy group, cyclohexanoyloxy group and benzoyloxy group. The benzoyloxy group may have a substituent, and the benzoyloxy group having a substituent is obtained by substituting one or more hydrogen atoms of the benzoyloxy group by an alkyl group having 1 to 9 carbon atoms or alkoxy group having 1 to 6 carbon atoms.

Examples of the alkoxycarbonyl group having 2 to 7 carbon atoms include methoxycarbonyl group, ethoxycarbonyl group, propoxycarbonyl group, isopropoxycarbonyl group, butoxycarbonyl group, pentyloxycarbonyl group, cyclopentyloxycarbonyl group, cyclohexyloxycarbonyl group and phenoxycarbonyl group. The phenoxycarbonyl group may have a substituent and the phenoxycarbonyl group having a substituent is obtained by substituting one or more hydrogen atoms of the above phenoxycarbonyl group by an alkyl group having 1 to 9 carbon atoms or alkoxy group having 1 to 6 carbon atoms.

The amide group is preferably an amide group having 1 to 7 carbon atoms which are substituted for the nitrogen of an amide group. Examples of the amide group include N-methylamide, N',N'-dimethylamide, N',N'-diethylamide, cyclopentylamide and cyclohexylamide. Or it may be a group represented by the following formula (9):

wherein W is a hetero ring having 5 to 6 carbon atoms and containing only nitrogen or nitrogen and oxygen.

Further, N-phenylamide and N,N'-diphenylamide having a phenyl group substituting the nitrogen of an amide group are also included. The hetero ring and the N,N'-diphenylamide may have a substituent, and the hetero ring and the N,N'-diphenylamide having a substituent are obtained by substituting one or more hydrogen atoms of a hetero ring and N,N'-diphenylamide group by an alkyl group having 1 to 6 carbon atoms, alkoxy group having 1 to 6 carbon atoms or halogen atom.

The halogenoalkyl group having 1 to 6 carbon atoms is obtained by substituting one or more hydrogen atoms of the above alkyl group by a fluorine atom, chlorine atom or bromine atom. Out of these, halogenoalkyl groups having a fluorine atom as a substituent are preferred. Preferred examples of the halogenoalkyl group include fluoromethyl group, difluoromethyl group and trifluoromethyl group.

The halogenoalkoxy group having 1 to 6 carbon atoms is obtained by substituting one or more hydrogen atoms of the above alkoxy group by a fluorine atom, chlorine atom or bromine atom. Examples of the halogenoalkoxy group include fluoromethoxy group, chloromethoxy group, bromomethoxy group, difluoromethoxy group, dichloromethoxy group, dibromomethoxy group, trifluoromethoxy group, trichloromethoxy group and tribromomethoxy group. Out of these, halogenoalkoxy groups having a fluorine atom as a substituent are preferred. Preferred examples of the halogenoalkoxy group include fluoromethoxy group, difluoromethoxy group and trifluoromethoxy group.

To develop a gray or brown color from a chromene composition obtained by combining these compounds, yellow, red and blue chromene compounds should be used in combination.

Preferred yellow to red compounds are compounds represented by the above formula (2) in which $R^{10}$ and $R^{11}$ are each preferably a hydrogen atom, alkyl group having 1 to 9 carbon atoms, alkoxy group having 1 to 6 carbon atoms, aryl group having 6 to 10 carbon atoms, acyloxy group having 2 to 7 carbon atoms, or alkoxycarbonyl group having 2 to 7 carbon atoms, cyanoalkyleneoxy group or hydroxyalkyl group, and $R^{11}$ is preferably an electron withdrawing group, or branched alkyl group or alkoxycarbonyl group having 3 to 6 carbon atoms, particularly preferably methoxycarbonyl group, cyclohexyloxycarbonyl group, propionylmethoxycarbonyl group, cyanomethyleneoxy group, hydroxymethyl group or isopropyl group when the fading speed is taken into account.

$R^9$ is preferably a hydrogen atom, alkyl group having 1 to 9 carbon atoms, alkoxy group having 1 to 6 carbon atoms, amino group or heterocyclic group having a nitrogen atom as a hetero atom and bonded to a benzene ring by the nitrogen atom bonded to the benzene ring. When the positioning of the absorption end at a short wavelength range is taken into account, $R^9$ is preferably substituted by an alkoxy group, amino group or heterocyclic group having a nitrogen atom as a hetero atom and bonded by the nitrogen atom at the 8-position. Preferred examples of the group include methoxy group, dimethylamino group and morpholino group.

$R^7$ or $R^8$ is preferably a group selected from hydrogen atom, alkyl group having 1 to 9 carbon atoms and alkoxy group having 1 to 6 carbon atoms. When photopolymerization resistance, photochromic durability and fading speed are taken into account, at least one of $R^7$ and $R^8$ is substituted at the 4-position. Examples of $R^7$ and $R^8$ include methoxy group and methyl group.

Preferred examples of the yellow to red compounds include chromene compounds represented by the following formulas (in the formulas, Me is a methyl group and iPr is a isopropyl group, the same shall apply hereinafter).

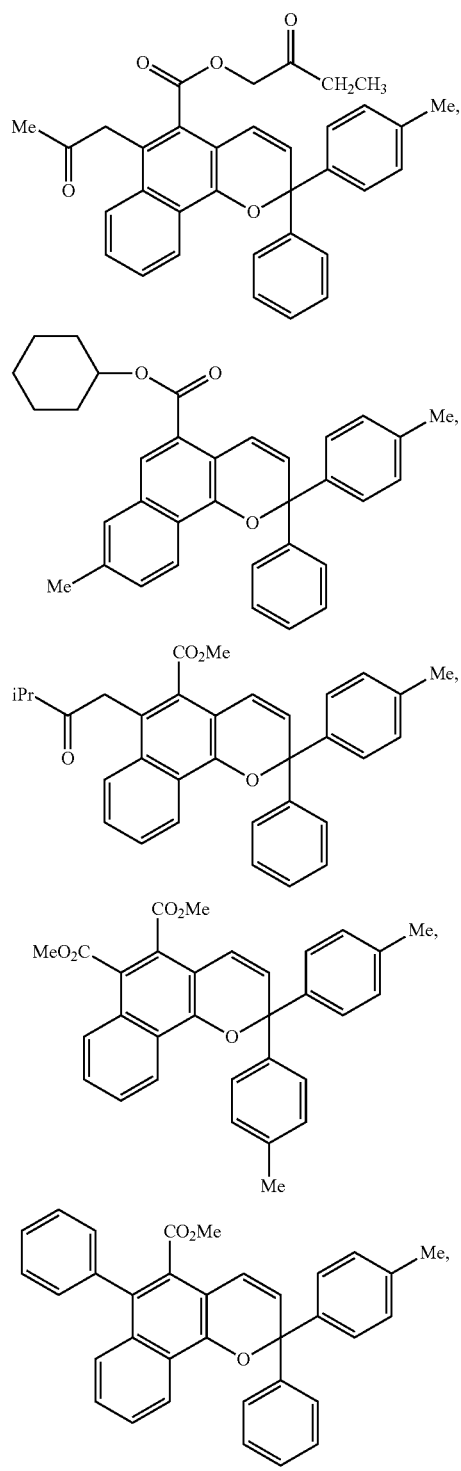

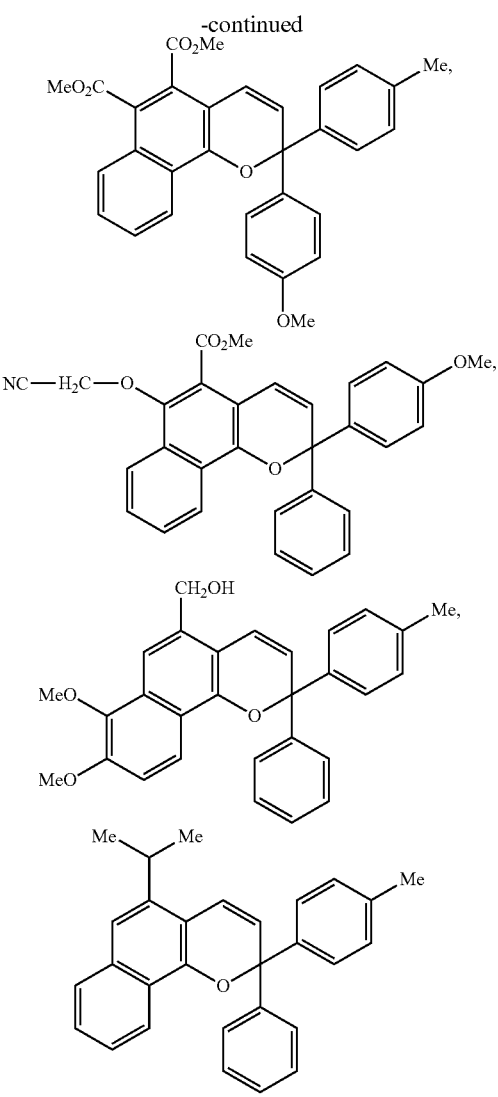

A preferred blue compound is a compound represented by the above formula (2) in which at least one of $R^7$ and $R^8$ is an amino group or heterocyclic group having a nitrogen atom as a hetero atom and bonded to a benzene ring by the nitrogen atom bonded to the benzene ring, particularly preferably substituted at the 4-position when photopolymerization resistance and photochromic durability in particular are taken into account. Specific examples of the group include dimethylamino group, morpholino group and piperidino group.

$R^{10}$ and $R^{11}$ are each preferably a hydrogen atom, alkyl group having 1 to 9 carbon atoms or acyloxyalkyl group having 1 to 6 carbon atoms. Preferred examples of these groups include methyl group and acetyloxymethylene group.

When the positioning of the absorption end at a short wavelength range is taken into account, $R^9$ is substituted by an alkoxy group, amino group or heterocyclic group having a nitrogen atom as a hetero atom and bonded to a benzene ring by the nitrogen atom bonded to the benzene ring at the 8-position. Specific examples of the group include methoxy group, ethoxy group, morpholino group and dimethylamino group. Further, when the improvement of the fading speed is taken into account, $R^9$ preferably has a methylenedioxy group forming a ring structure at the 8- and 9-positions.

Preferred examples of the blue compound are given below.

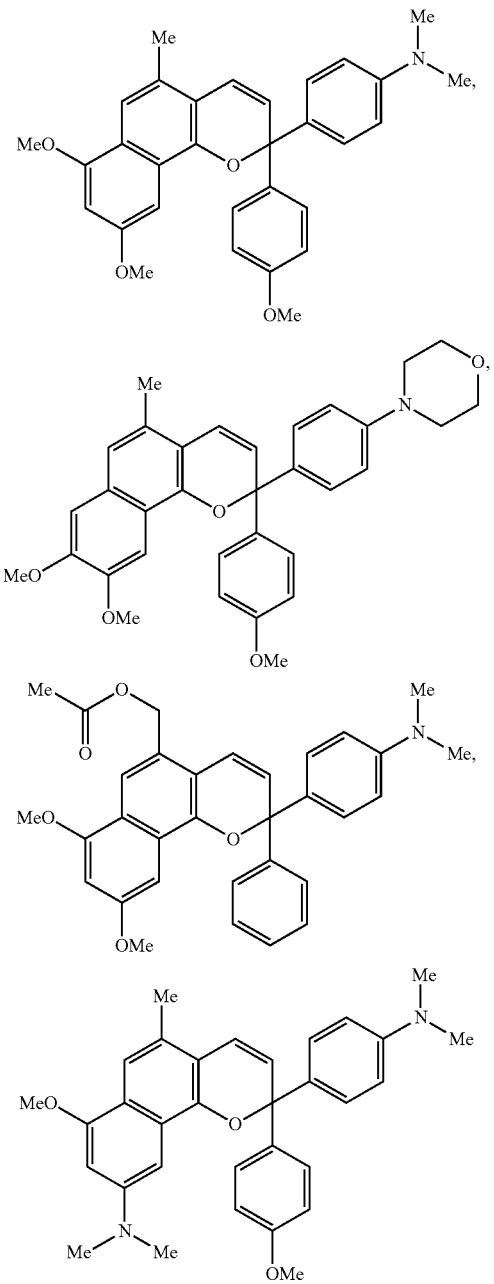

Further, $R^{10}$ and $R^{11}$ in the above formula (2) may be bonded together to form a group represented by the following formula (3).

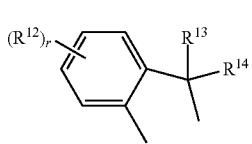

In this case, the above formula (2) is represented by the following formula (10).

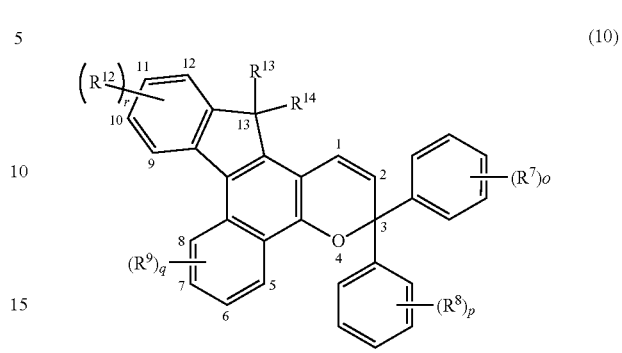

$R^{12}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms.

Examples of $R^{12}$ include the same substituents as those enumerated for $R^{10}$ and $R^{11}$ in the above formula (2). r is an integer of 0 to 3. Specific examples of $R^{12}$ include methyl group, methoxy group, propoxy group, dimethylamino group, morpholino group, fluorine atom, cyano group, trifluoromethyl group, methoxycarbonyl group and carboxyl group.

$R^{13}$ and $R^{14}$ are each a hydrogen atom, hydroxyl group, alkyl group having 1 to 9 carbon atoms, alkoxy group having 1 to 6 carbon atoms, halogenoalkyl group having 1 to 6 carbon atoms or halogenoalkoxy group having 1 to 6 carbon atoms. Examples of the $R^{13}$ and $R^{14}$ include the same substituents as those enumerated for $R^{10}$ and $R^{11}$ in the above formula (2). Preferred examples of the groups include methyl group, ethyl group, butyl group, methoxy group, ethoxy group, butoxy group and hydroxyl group.

Further, $R^{13}$ and $R^{14}$ may be bonded together to form a cyclic structure. The cyclic structure formed by bonding together $R^{13}$ and $R^{14}$ is preferably an aliphatic hydrocarbon ring having 4 to 10 carbon atoms forming the ring. Further, an aromatic hydrocarbon ring such as benzene or naphthalene may be condensed to the aliphatic hydrocarbon ring. The aliphatic hydrocarbon ring may have an alkyl group having 1 to 5 carbon atoms or alkoxy group having 1 to 9 carbon atoms as a substituent. The following rings are preferred from the viewpoint of fading speed. In the rings shown below, the carbon atom (spiro carbon atom) having two bonds at the lowest position corresponds to a carbon atom of the five-membered ring to which $R^{13}$ and $R^{14}$ are bonded.

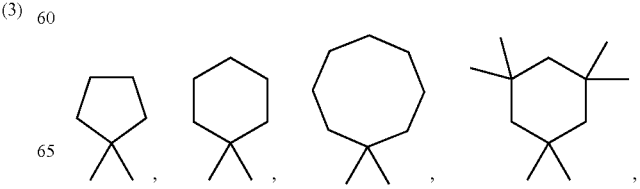

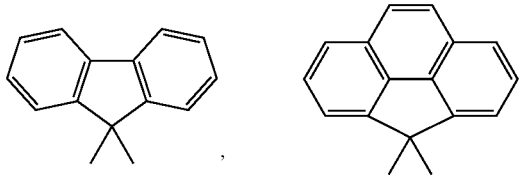

$R^{13}$ and $R^{14}$ are each preferably an alkyl group having 1 to 9 carbon atoms, alkoxy group having 1 to 6 carbon atoms or aliphatic hydrocarbon ring group having 4 to 10 carbon atoms formed by bonding together $R^{13}$ and $R^{14}$ from the viewpoint of photochromic durability and fading speed.

($R^{15}$)

Further, $R^{10}$ and $R^{11}$ may be bonded together to form a group represented by the following formula (4).

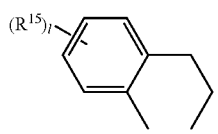

(4)

In this case, the above formula (4) is represented by the following formula (11).

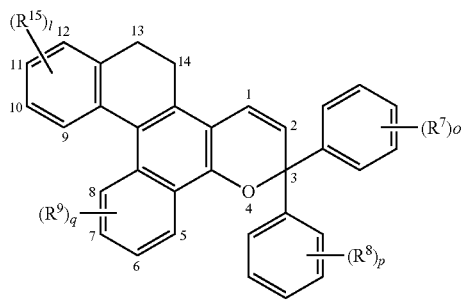

(11)

When $R^{10}$ and $R^{11}$ are bonded together to form a substituent represented by the above formula (10) or (11), a chromene compound which develops not only a blue color but also an intermediate color such as gray or brown can be obtained (intermediate color chromene compound has two absorption maximums at least at around 450 nm and around 580 nm at the time of developing color). When the intermediate color chromene compound is used in combination, the photochromic composition of the present invention can make color uniform during color development and fading and can suppress the shift of the developed color caused by the deterioration of photochromic properties.

Out of the compounds represented by the above formulas (10) and (11), a preferred blue or intermediate color chromene compound is a compound in which $R^7$ and $R^8$ are each preferably a hydrogen atom, alkyl group having 1 to 6 carbon atoms, alkoxy group having 1 to 6 carbon atoms, amino group or heterocyclic group having a nitrogen atom as a hetero atom and bonded by the nitrogen atom, and at least one of $R^7$ and $R^8$ is preferably substituted at the 4-position when photopolymerization durability, photochromic durability and fading speed are taken into consideration. Specific examples of these groups include methyl group, methoxy group, isopropoxy group, butoxy group and morpholino group.

$R^9$ is preferably a hydrogen atom, alkoxy group having 1 to 6 carbon atoms, amino group or heterocyclic group having a nitrogen atom as a hetero atom and bonded by the nitrogen atom, and particularly preferably substituted at the 7-position to position the absorption end at a short wavelength range. Specific examples of $R^9$ include methoxy group and morpholino group. Further, when the positioning of the absorption end at a short wavelength range and the fading speed are both taken into consideration, an electron donating group such as alkylenedioxy, specifically methylenedioxy group is preferably substituted at the 6- and 7-positions.

$R^{15}$ is preferably substituted by an electron absorbing group at the 11-position because the absorption end can be positioned at a short wavelength range and a high fading speed can be obtained. Preferred examples of $R^{15}$ include fluorine atom, cyano group, carboxyl group, methoxycarbonyl group and trifluoromethyl group.

Out of the compounds represented by the above formula (11), a compound in which $R^{15}$ is a hydrogen atom is preferred.

Examples of the preferred compound are chromene compounds represented by the following formulas (in these formulas, nBu is a normal butyl group).

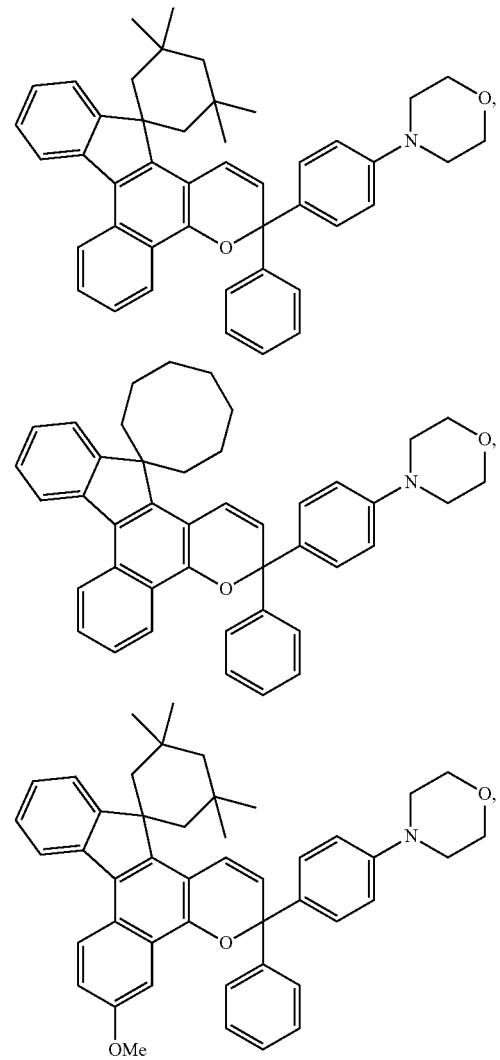

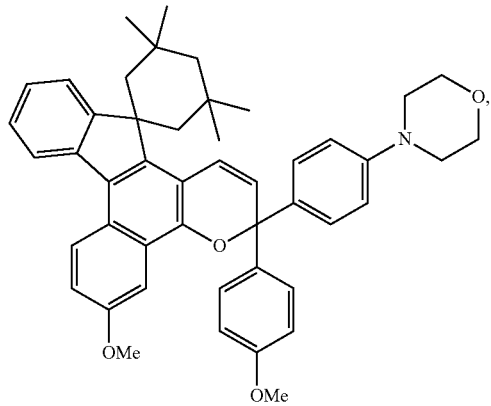
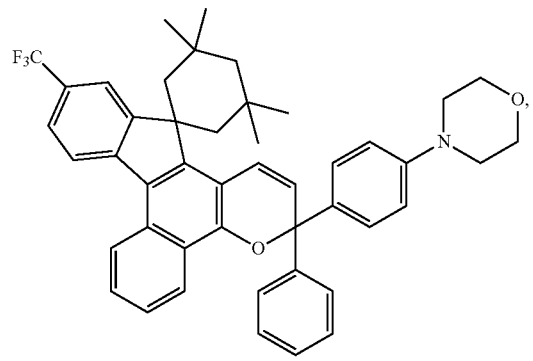
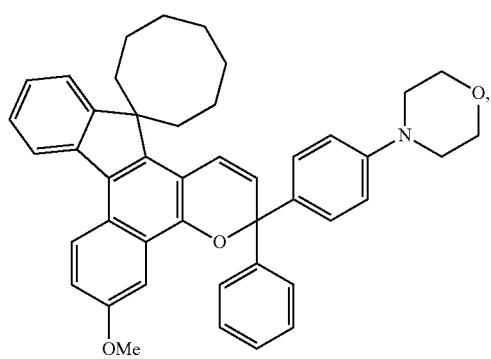
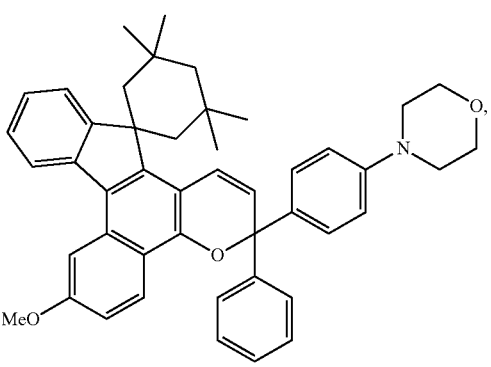
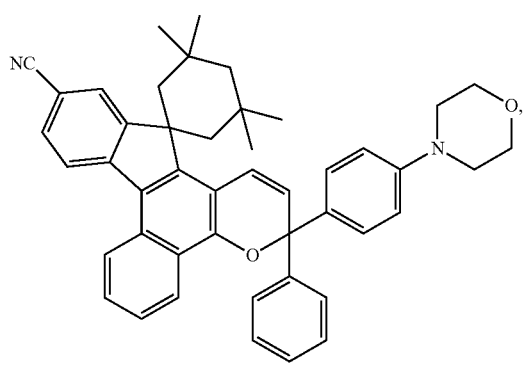
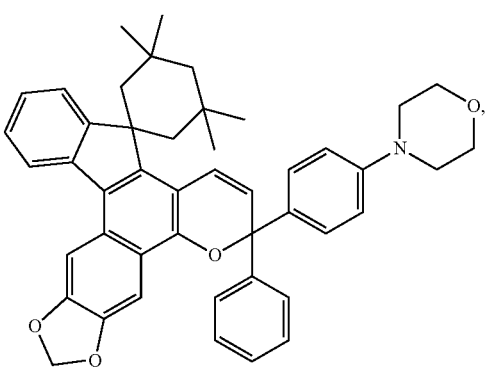
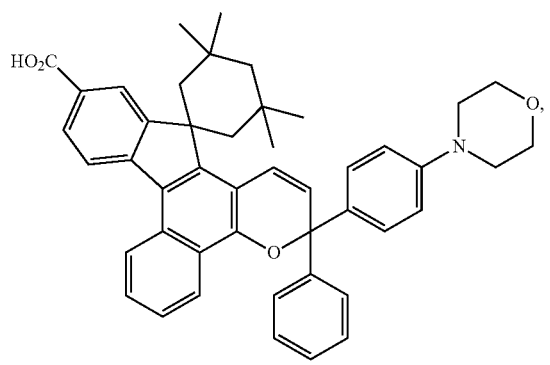
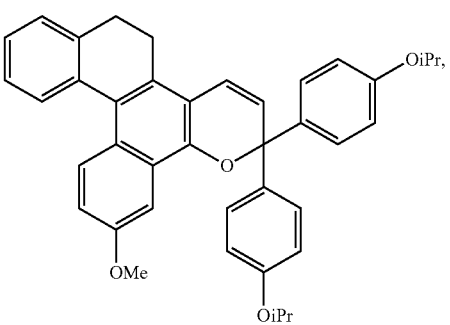

-continued
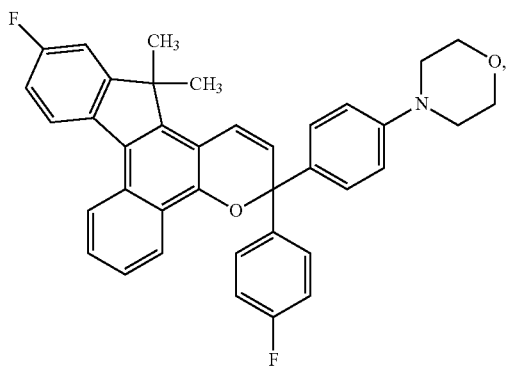
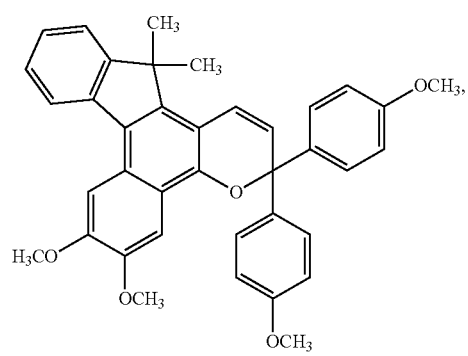
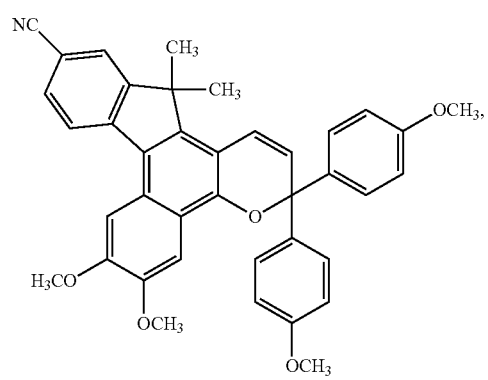
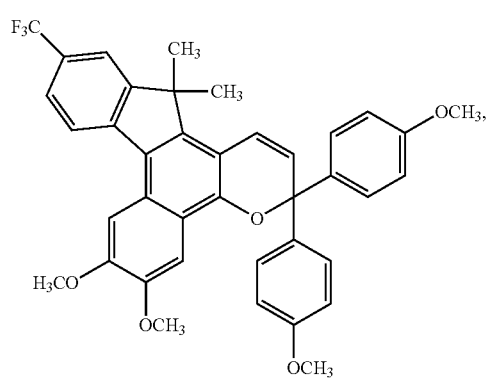
-continued
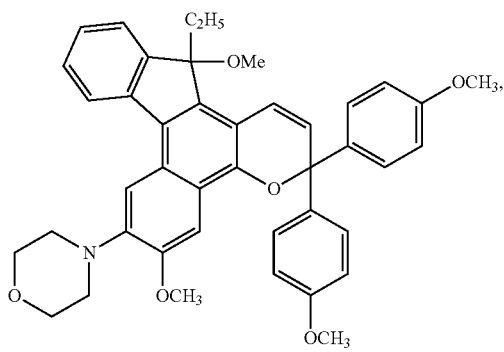
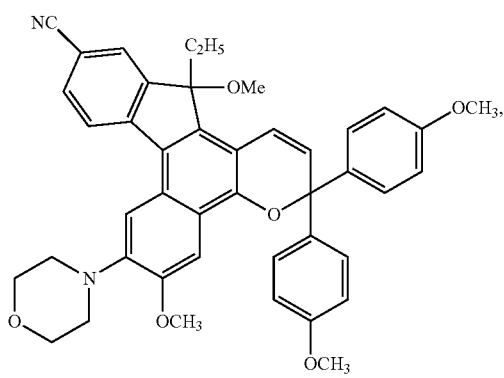
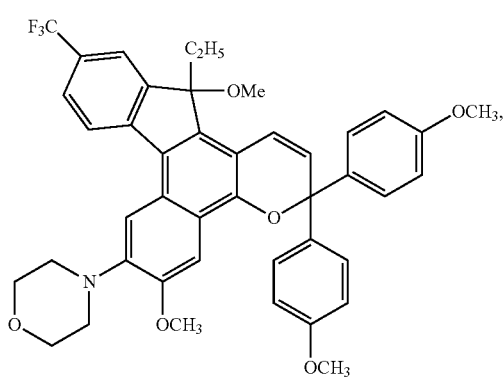
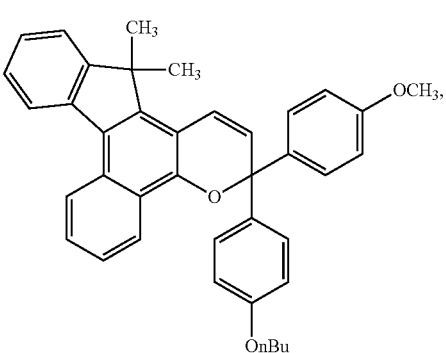

-continued

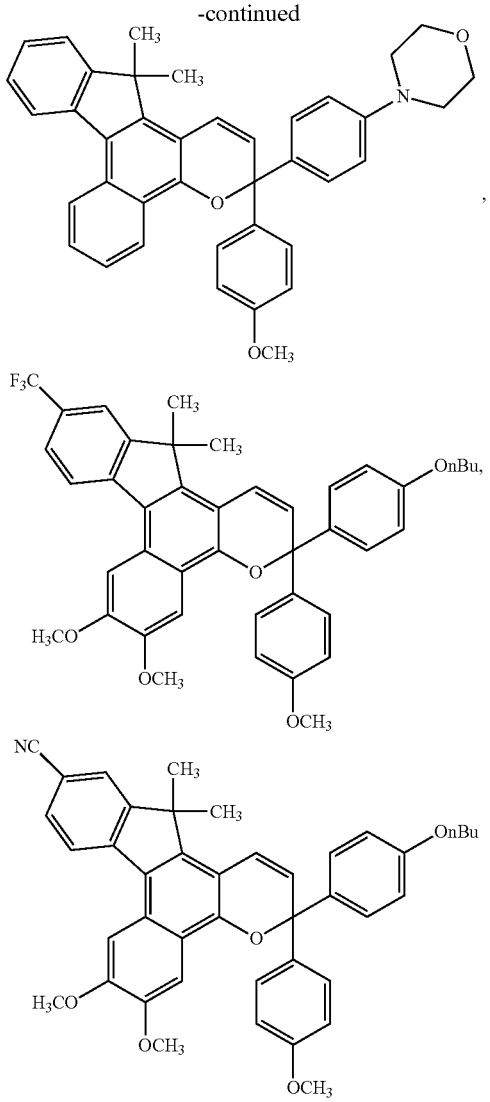

To prepare a chromene composition which comprises the chromene compound of the present invention and chromene compounds represented by the above formulas (2) and (10) or (11), the mixing ratio of these chromene compounds may be suitably determined according to a desired color. In this case, the amount of the chromene compound of the present invention or the chromene composition is preferably 0.001 to 10 parts by mass based on 100 parts by mass of the total of the polymerizable monomers. Stated more specifically, in the case of a coating thin film (such as a film as thin as about 100 μm), the amount of the chromene compound of the present invention is 0.01 to 5.0 parts by mass, the amount of the chromene compound represented by the above formula (2) is 0.01 to 5.0 parts by mass, and the amount of the chromene compound represented by the above formula (10) or (11) is 0.01 to 5.0 parts by mass based on 100 parts by mass of the coating film or the total of the polymerizable monomers which provide the coating film to control color. In the case of a thick cured product (as thick as 1 mm or more), the amount of the chromene compound of the present invention is 0.001 to 0.5 part by mass, the amount of the chromene compound represented by the above formula (2) is 0.001 to 0.5 part by mass, and the chromene compound represented by the above formula (10) or (11) is 0.001 to 0.5 part by mass based on 100 parts by mass of the thick cured product or the total of the polymerizable monomers which provide the thick cured product to control color. For fine color control, another photochromic compound except for the above photochromic compounds may be further mixed.

(Use of Chromene Compound)

The photochromic composition which comprises the chromene compound of the present invention and the chromene compounds represented by the above formulas (2) and (10) or (11) shows excellent photochromic properties in any medium but a dispersion or solution of the composition dispersed or dissolved in a polymer material is the most preferred from a practical point of view and provides excellent photochromic properties in fact.

Any polymer solid matrix (polymer material) is acceptable if the chromene compound of the present invention is uniformly dispersed in the polymer solid matrix. The method of dispersing the chromene compound of the present invention in the above polymer solid matrix (polymer material) is not particularly limited, and commonly used methods may be employed. For example, one in which the above thermoplastic resin and the chromene compounds are kneaded together while they are molten to disperse them into the resin (polymer material), one in which the chromene compounds are dissolved in the above polymerizable monomers and a polymerization catalyst is added to the resulting solution to polymerize it by heat or light so as to disperse the chromene compounds into the resin (polymer material), or one in which the above thermoplastic resin or the surface of the thermoplastic resin is dyed with the chromene compounds to disperse them into the resin (polymer material) may be employed. The photochromic composition which comprises the above thermoplastic resin or thermosetting resin polymer material and the chromene compound of the present invention and is obtained by the above method can be used for various purposes due to its excellent photochromic properties.

From the viewpoint of excellent photochromic properties such as high color optical density, high fading speed and high durability, it is preferred that a curable composition should be prepared by mixing together the following polymerizable monomers and the chromene compounds represented by the above formulas (1), (2) and (10) or (11).

Examples of the curable composition are given below.

1) A Curable Composition to be Used as a Coating Thin Film

This is a curable composition which comprises A) a polymerizable monomer having an L scale Rockwell hardness of a polymer obtained by homopolymerization of 40 or less, B) a polyfunctional polymerizable monomer having a functionality of 3 or more and an L scale Rockwell hardness of a polymer obtained by homopolymerization of 60 or more and C) the chromene compounds represented by the above formulas (1), (2) and (10) or (11) and optionally D) a bifunctional polymerizable monomer having an L scale Rockwell hardness of a polymer obtained by homopolymerization of 60 or more.

2) A Curable Composition to be Used as a Thick Cured Product

This is a curable composition which comprises A) a polymerizable monomer having an L scale Rockwell hardness of a polymer obtained by homopolymerization of 40 or less, B) a polyfunctional polymerizable monomer having a functionality of 3 or more and an L scale Rockwell hardness of a polymer obtained by homopolymerization of 60 or more, C) a bifunctional polymerizable monomer having an L scale Rockwell hardness of a polymer obtained by homopolymerization of 60 or more and D) the chromene compounds represented by the above formulas (1), (2) and (10) or (11) and which has an L scale Rockwell hardness of a cured product thereof of 65 or more.

(Polymerizable Monomer Having an L Scale Rockwell Hardness of a Polymer Obtained by Homopolymerization of 40 or Less)

The polymerizable monomer having an L scale Rockwell hardness of a polymer obtained by homopolymerization of 40 or less (to be simply referred to as "low hardness monomer" hereinafter) is not particularly limited if it is a polymerizable monomer having an L scale Rockwell hardness of a homopolymer obtained by homopolymerization of 40 or less, and any known polymerizable monomer may be used. The term "L scale Rockwell hardness" means hardness measured in accordance with JIS-B7726, and whether the homopolymer of each monomer satisfies the above hardness condition can be easily judged by carrying out this measurement. Stated more specifically, as shown in the examples which will be given hereinafter, this can be easily checked by polymerizing a monomer to obtain a cured product having a thickness of 2 mm and keeping it in a 25° C. chamber for 1 day to measure its L scale Rockwell harness with a Rockwell hardness meter. The cured product obtained from this low hardness monomer has excellent photochromic properties such as high color optical density and high fading speed. To further improve the photochromic properties, the L scale Rockwell hardness of the low hardness monomer is preferably 35 or less.

The polymerizable group is not particularly limited if it shows polymerizability and may be an epoxy group but preferably a group which shows radical polymerizability. Examples of the radically polymerizable group include methacryloyl group, acryloyl group, vinyl group and allyl group. Out of these, methacryloyl group and acryloyl group are particularly preferred.

The polymer to be measured for the above L scale Rockwell hardness is obtained by cast polymerization under the condition that not less than 90 mol % (polymerization ratio of not less than 90%), preferably not less than 95 mol % of the charged monomer is polymerized. When a radically polymerizable monomer which has the above L scale Rockwell hardness value of a polymer obtained by homopolymerizing the monomer in the above polymerization ratio is used, the obtained cured product has excellent photochromic properties such as color optical density and fading speed.

A low hardness monomer disclosed by WO01/05854 may be used as the low hardness monomer. A preferred example of the low hardness monomer is represented by the following formula.

(Bifunctional and Polyfunctional Polymerizable Monomers Having an L Scale Rockwell Hardness of a Polymer Obtained by Homopolymerization of 60 or More)

When the curable composition containing the photochromic compound of the present invention comprises the above low hardness monomer and bifunctional and polyfunctional polymerizable monomers having an L scale Rockwell hardness of a polymer obtained by homopolymerization of 60 or more (to be referred to as "high hardness monomers" hereinafter), the obtained cured product has excellent basic properties such as hardness and heat resistance while maintaining excellent photochromic properties such as color developing speed and fading speed. The method of checking the L scale Rockwell hardness is the same as that for the above low hardness monomer.

The polymerizable group is not particularly limited if it shows polymerizability but preferably a group having radical polymerizability, such as methacryloyl group, acryloyl group, vinyl group or allyl group. Out of these, methacryloyl group and acryloyl group are particularly preferred.

Detailing the polyfunctional high hardness monomer, it is not particularly limited if it is a polymerizable monomer having at least 3 polymerizable groups in the molecule and an L scale Rockwell hardness of a homopolymer obtained by homopolymerization of 60 or more, and any known polyfunctional high hardness monomer may be used. A polyfunctional high hardness monomer having 3 to 6 polymerizable groups in the molecule is preferred because it is easily acquired industrially.

The cured product obtained from the polyfunctional high hardness monomer has greatly improved basic properties such as hardness and heat resistance and further improved photochromic properties such as color development and fading sensitivity. To develop the above effect more markedly, it is preferred that a polyfunctional polymerizable monomer having an L scale Rockwell hardness of 80 to 130 should be used. A low hardness monomer disclosed by WO01/05854 may be used as the high hardness monomer. A preferred example of the high hardness monomer is a polyfunctional high hardness monomer represented by the following formula.

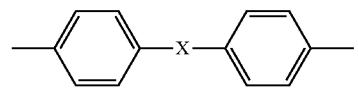

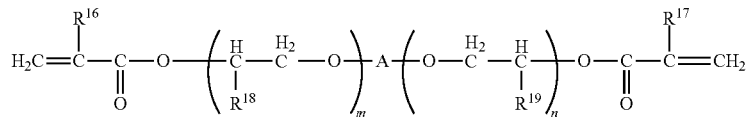

In the above formula, $R^{16}$ and $R^{17}$ are each independently a hydrogen atom or methyl group, $R^{18}$ and $R^{19}$ are each independently a hydrogen atom or alkyl group having 1 to 2 carbon atoms, the group -A- is —CHR$^{18}$—CH$_2$—O— or group represented by the following formula (the group X in the formula is —O—, —S—, —S(=O)$_2$—, —C(=O)—O—, —CH$_2$—, —CH=CH— or —C(CH$_3$)$_2$—), and m and n are each an integer which satisfies (m+n)=8 to 30.

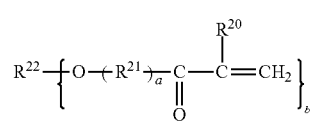

In the above formula, $R^{20}$ is a hydrogen atom or methyl group, the group —$R^{21}$— is —CH$_2$CH$_2$O—, —CH$_2$CH(CH$_3$)O— or —C(=O)CH$_2$CH$_2$CH$_2$CH$_2$CH$_2$O—, $R^{22}$ is a trivalent to hexavalent organic residue, a is an integer of 0 to 3, and b is an integer of 3 to 6.

Giving a detailed description of the bifunctional high hardness monomer, the bifunctional polymerizable monomer having an L scale Rockwell hardness of a polymer obtained by homopolymerization of 60 or more is not particularly limited if it has two polymerizable groups in the molecule and an L scale Rockwell hardness of a homopolymer obtained by homopolymerization of 60 or more, and any known bifunctional polymerizable monomer may be used.

The high hardness monomer has the effect of providing impact resistance to the obtained cured product and maintaining photochromic properties such as fading speed in a well-balanced manner. To develop the above effect more markedly, it is preferred that a high hardness monomer having an L scale Rockwell hardness of 65 to 120 should be used. A high hardness monomer disclosed by WO01/05854 may be used as the above high hardness monomer. A preferred example of the high hardness monomer is a bifunctional high hardness monomer represented by the following formula.

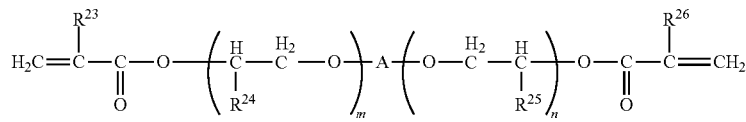

In the above formula, $R^{23}$ and $R^{24}$ are each independently a hydrogen atom or methyl group, $R^{25}$ and $R^{26}$ are each independently a hydrogen atom or alkyl group having 1 to 2 carbon atoms, the group -A- is —$CHR^{24}$—$CH_2$—O— or group represented by the following formula (the group —X— is —O—, —S—, —S(=O)$_2$—, —C(=O)—O—, —$CH_2$—, —CH=CH— or —C(CH$_3$)$_2$—), and m and n are each an integer which satisfies (m+n)=2 to 7.

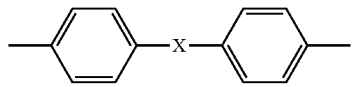

(Curable Composition)

In the present invention, when the curable composition is used as a coating film, it is preferred that the above low hardness monomer and the above high hardness monomers should be mixed together to ensure that the Vickers hardness of a cured layer obtained by copolymerizing the low hardness monomer and the high hardness monomers becomes 2.5 kgf or more, preferably 3.0 kgf or more, particularly preferably 3.5 to 7.0 kgf to achieve excellent photochromic properties. To check the Vickers hardness of the cured layer, a pyramid-like indenter made of quadrilateral diamond having a facing angle α of 136° is pressed into the surface of a material, the surface area S (mm$^2$) is calculated from the length d (mm) of the diagonal line of a dent left behind after a load is removed, and the Vickers hardness can be obtained from a value obtained by dividing a test load F (N) by the calculated surface area S (mm$^2$).

The composition for obtaining the above Vickers hardness value of the cured layer differs according to the types of the monomers in use and cannot be specified unconditionally. However, in general, it is preferred to set the amount of the low hardness monomer to 30 to 90 mass, specifically 40 to 80 mass % and the amount of the high hardness monomers to 10 to 70 mass, specifically 20 to 60 mass % based on the total mass of the both monomers in order to obtain a cured product having excellent photochromic properties and basic properties.

In the present invention, when the curable composition is used as a thick cured product, the above low hardness monomer and the above high hardness monomers are mixed together to ensure that the L scale Rockwell hardness of a cured product obtained by copolymerizing the low hardness monomer and the high hardness monomers becomes 60 or more, preferably 65 or more, particularly preferably 70 to 110. The method of checking the L scale Rockwell hardness of the cured product is the same as that for the above low hardness monomer.

The composition for obtaining the above L scale Rockwell hardness value of the cured layer differs according to the types of the monomers in use and cannot be specified unconditionally. However, in general, it is preferred to set the amount of the low hardness monomer to 1 to 50 mass, specifically 2 to 30 mass % and the amount of the high hardness monomers to 50 to 99 mass, specifically 70 to 98 mass % based on the total mass of the both monomers in order to obtain a cured product having excellent photochromic properties and basic properties.

Further, it is more preferred to set the amount of the polyfunctional high hardness monomer to 1 to 20 mass, specifically 2 to 10 mass % and the amount of the bifunctional high hardness monomer to 80 to 99 mass %, specifically 90 to 98 mass % based on the total mass of all the high hardness monomers in order to improve the hardness and heat resistance of a cured product.

Another polymerizable monomer (may also be referred to as "optional monomer" hereinafter) may be optionally added to the curable composition in limits that do not impair the effect of the present invention in addition to the low hardness monomer and the high hardness monomers.

Examples of the another polymerizable monomer (to be also referred to as "optional monomer" hereinafter) include unsaturated carboxylic acids such as acrylic acid, methacrylic acid and maleic anhydride; acrylate and methacrylate compounds such as methyl methacrylate, benzyl methacrylate, phenyl methacrylate and 2-hydroxyethyl methacrylate; fumarate compounds such as diethyl fumarate and diphenyl fumarate; thioacrylate and thiomethacrylate compounds such as methyl thioacrylate, benzyl thioacrylate and benzyl thiomethacrylate; vinyl compounds such as styrene, chlorostyrene, methyl styrene, vinyl naphthalene, α-methyl styrene dimer and bromostyrene; and other polymerizable monofunctional monomers.

One or a mixture of the above optional monomers may be added, and the amount of the optional monomer is preferably not more than 40 parts by weight, more preferably not more than 30 parts by weight based on 100 parts by weight of the total of the low hardness monomer and the high hardness monomers.

Further, it is preferred that a polymerizable monomer having at least one epoxy group should be contained in an amount of 0.01 to 40 mass %, preferably 0.1 to 30 mass % based on the total of all the polymerizable monomers contained in the curable composition to provide excellent color development sensitivity and fading speed and high photochromic durability. In this case, the polymerizable monomer having at least one epoxy group may be contained in either one of the above low hardness monomer and the high hardness monomer which meet the above requirement or as an optional monomer. For example, a low hardness monomer 5 and a low hardness monomer 6 are used as at least some of the above low hardness monomers to meet the above requirement.

In the present invention, a polymerizable monomer having an epoxy group disclosed by WO01/05854 may be used as the above polymerizable monomer having at least one epoxy group.

(Method of Curing Curable Composition)

The curing method for obtaining a cured product from the photochromic curable composition of the present invention is not particularly limited, and a known radical polymerization technique may be employed. To start polymerization, use of a radical polymerization initiator such as a peroxide or azo compound, exposure to ultraviolet radiation, α-ray, β-ray or γ-ray, or both of them are employed. A typical polymerization technique is cast polymerization in which the photochromic curable composition of the present invention containing a radical polymerization initiator is injected into the space between molds held by an elastomer gasket or spacer and cured in an air furnace and the cured product is taken out. As typical examples of the polymerization initiator, thermopolymerization initiators include diacyl peroxides such as benzoyl peroxide, p-chlorobenzoyl peroxide, decanoyl peroxide, lauroyl peroxide and acetyl peroxide; peroxy esters such as t-butylperoxy-2-ethyl hexanoate, t-butylperoxy neodecanate, cumylperoxy neodecanate and t-butylperoxy benzoate; percarbonates such as diisopropylperoxy dicarbonate and di-sec-butylperoxy dicarbonate; and azo compounds such as azobisisobutyronitrile, and photopolymerization initiators include acetophenone-based compounds such as 1-phenyl-2-hydroxy-2-methylpropan-1-one, 1-hydroxycyclohexylphenyl ketone and 1-(4-isopropylphenyl)-2-hydroxy-2-methyl-propan-1-one; α-dicarbonyl-based compounds such as 1,2-diphenylethane dione and methylphenyl glyoxylate; and acylphosphine oxide-based compounds such as 2,6-dimethylbenzoyl diphenylphosphine oxide, 2,4,6-trimethylbenzoyl diphenylphosphine oxide, methyl 2,4,6-trimethylbenzoyl diphenylphosphinate, 2,6-dichlorobenzoyl diphenylphosphine oxide and 2,6-dimethoxybenzoyl diphenylphosphine oxide. These polymerization initiators may be used alone or in combination of two or more. A thermopolymerization initiator and a photopolymerization initiator may be used in combination. When a photopolymerization initiator is used, a known polymerization accelerator such as a tertiary amine may be used in combination.

In the present invention, when the above polymerization initiator is used, its amount is preferably 0.001 to 10 parts by mass, more preferably 0.01 to 5 parts by mass based on 100 parts by mass of the total of the polymerizable monomers.

When the photochromic curable composition of the present invention is to be polymerized, the temperature out of the polymerization conditions has an influence upon the properties of the obtained photochromic cured product. Since this temperature condition is influenced by the type and amount of the radical polymerization initiator and the types of the monomers, it is not specified unconditionally. In general, so-called "tapered type polymerization" in which polymerization is started at a relatively low temperature, then the temperature is gradually raised, and the composition is cured at a high temperature at the end of polymerization is preferably carried out. Since the polymerization time differs according to various factors like the temperature, the optimum time is preferably determined in accordance with these conditions in advance. It is preferred to select conditions under which polymerization is completed in 2 to 24 hours.

When the cured product is a coating layer, a polymerization technique in which the above curable composition containing a thermopolymerization initiator and/or a photopolymerization initiator is cured by exposure to ultraviolet radiation and heated to complete polymerization is employed. The heating temperature may be suitably determined in consideration of the heat resistance of a substrate. When the curable composition of the present invention is used, it may be heated at 70 to 130° C. for 1 to 3 hours to obtain sufficiently high adhesion to the substrate.

When polymerization is carried out by exposure to ultraviolet radiation, any known light source may be used. Examples of the light source include super high-pressure mercury lamp, high-pressure mercury lamp, low-pressure mercury lamp, xenon lamp, carbon arc, sterilization lamp, metal halide lamp and electroless lamp. The time of exposure using the light source may be suitably determined according to the type, absorption wavelength and sensitivity of the above photopolymerization initiator and the film thickness of the photochromic layer. When an electron beam is used as the light source, the photochromic layer can be cured without adding a photopolymerization initiator.

Although the curable composition of the present invention can be used by itself as a photochromic material after it is cured by using the above polymerization initiator, it is particularly preferably used as a coating material for coating a substrate such as an optical substrate, preferably an optical material such as a spectacle lens.

The optical material is not particularly limited and may be a known optical material such as a spectacle lens or window glass for houses and automobiles.

As the spectacle lens, there are known plastic spectacle lenses made of (meth)acrylic resin, polycarbonate resin, allyl resin, thiourethane resin, urethane resin or thioepoxy resin as well as glass spectacle lenses. When the curable composition of the present invention is used as a coating material for spectacle lenses, it can be used for any spectacle lenses without restriction. It is preferably used as a coating material for plastic spectacle lenses, more preferably for spectacle lenses made of (meth)acrylic resin-based polycarbonate resin, allyl resin, thiourethane resin, urethane resin or thioepoxy resin.

When the curable composition of the present invention is used as a coating material for optical materials such as spectacle lenses, it is applied to an optical material by spin coating, spray coating, dip coating or dip-spin coating and then cured by exposure of light or by heating. More preferably, after it is cured by exposure of light, it is further heated to complete polymerization. When the substrate is coated with the curable composition, the substrate is preferably subjected to a pretreatment which will be described hereinafter in advance. If necessary, a resin layer for obtaining strong adhesion may be formed between the lens and the coating layer. The resin layer for improving adhesion may be any resin layer such as an urethane resin or epoxy resin layer.

The thickness of the coating layer obtained by curing by the above method is not particularly limited but preferably relatively large because sufficiently high color optical density and excellent photochromic durability are obtained even though the concentration of the photochromic compound is low. However, as the thickness of the coating layer is larger, initial yellowness increases. Therefore, the thickness of the coating layer is preferably 10 to 100 μm, more preferably 20 to 50 μm.

(Other Application Methods of Chromene Compound of the Present Invention)

For instance, when the chromene compound of the present invention is used in a photochromic plastic lens, if a photochromic plastic lens is manufactured by a method by which uniform light control performance is obtained, the lens manufacturing method is not particularly limited. Examples of the method include one in which a polymer film containing the chromene compound of the present invention uniformly dispersed therein is sandwiched between lenses, one in which the chromene compound of the present invention is dispersed in the above polymerizable monomers and the polymerizable monomers are polymerized by a predetermined technique, or one in which the chromene compound of the present invention is dissolved in silicone oil, for example, and the resulting solution is impregnated into the surface of a lens at 150 to 200° C. for 10 to 60 minutes so as to cover the surface with the curable substance.

Although the cured product or optical material obtained as described above may be used as a photochromic optical material as it is, it is preferably covered with a hard coat material. The scratch resistance of the photochromic optical material can be improved by covering with the hard coat material.

Any known hard coat material may be used as the hard coat material, and a hard coat agent comprising a silane coupling agent or a sol of a metal oxide such as silicon, zirconium, antimony or aluminum oxide as the main component and a hard coat agent comprising an organic polymer as the main component may be used.

Further, processing and a secondary treatment such as an anti-reflection treatment or antistatic treatment may be carried out by depositing a thin film of a metal oxide such as $SiO_2$, $TiO_2$ or $ZrO_2$ or forming an organic polymer thin coating film on a single cured product of the curable composition of the present invention, the cured surface as a coating material for optical materials, or the hard coated surface after coating.

(Other Applications)

The chromene compound of the present invention can be used as a photochromic material in a wide range of fields, such as recording materials as substitutes for silver halide photosensitive materials, copy materials, printing photosensitive materials, recording materials for cathode ray tubes, photosensitive materials for lasers and photosensitive materials for holography. The photochromic material comprising the chromene compound of the present invention may also be used as an optical article such as photochromic plastic lens, optical filter material, display material, actinometer or ornament.

EXAMPLES

The following examples are provided for the purpose of further illustrating the present invention but are in no way to be taken as limiting.

Example 1

4.9 g (20 mmol) of the following naphthol derivative and 5.2 g (22 mmol) of the following propargyl alcohol derivative were dissolved in 300 ml of toluene, and 0.05 g of p-toluene-sulfonic acid was further added to the resulting solution and stirred at a reflux temperature for 30 minutes. After a reaction, the solvent was removed, and the resulting solution was purified on silica gel by chromatography to obtain 3.5 g of a white powder product.

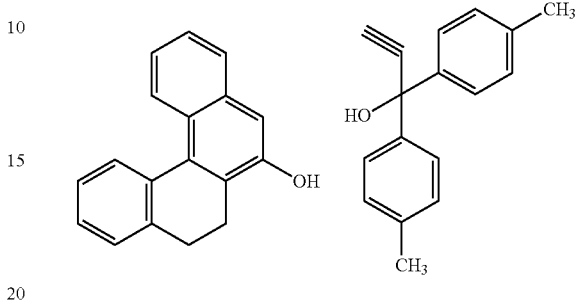

As for the elemental analysis values of this product, 90.30% of C, 6.06% of H and 3.64% of O were contained and perfectly matched 90.52% of C, 6.00% of H and 3.48% of O as calculation values of $C_{35}H_{28}O$.

When the proton nuclear magnetic resonance spectrum of the product was measured, a 10H peak based on an alkylene group was seen at δ of around 0.5 to 4.0 ppm and 18H peak based on an aromatic proton and the proton of an alkene were seen at δ of around 5.0 to 9.0 ppm.

Further, when the $^{13}C$-nuclear magnetic resonance spectrum of the product was measured, a peak based on the carbon of an aromatic ring was seen at δ of around 110 to 160 ppm, a peak based on the carbon of an alkene was seen at δ of around 80 to 140 ppm, and a peak based on the carbon of an alkyl was seen at δ of 20 to 60 ppm.

It was confirmed from the above results that the isolated product was a compound represented by the following structural formula.

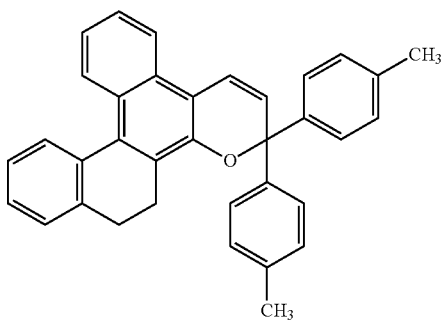

Examples 2 to 16

Chromene compounds shown in Tables 1, 2, 3 and 4 were synthesized in the same manner as in Example 1. When the obtained products were analyzed by using the same structure identification means as in Example 1, it was confirmed that they were compounds represented by structural formulas shown in Tables 1, 2, 3 and 4. The results of structural analysis are shown in Table 5.

TABLE 1
| Ex. No. | Naphthol derivative | Propargyl alcohol derivative | Product | Yield (%) |
|---|---|---|---|---|
| 2 | 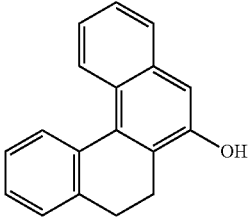 | 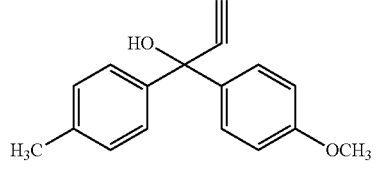 | 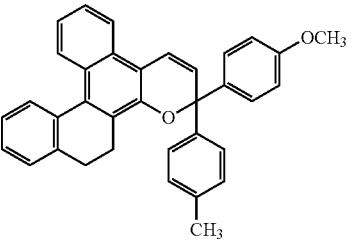 | 36 |
| 3 | 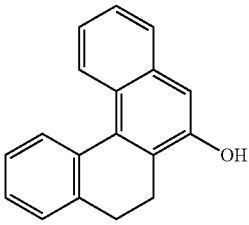 | 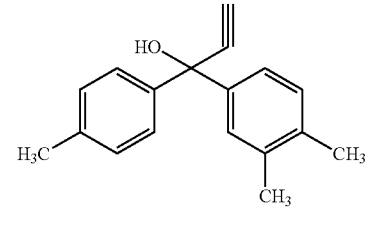 | 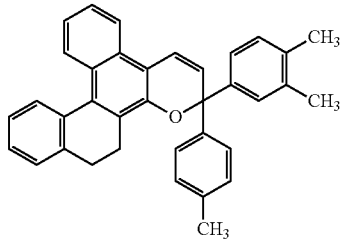 | 24 |
| 4 | 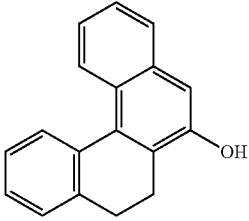 | 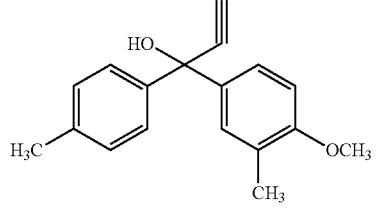 | 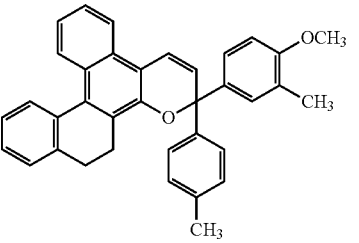 | 21 |
| 5 | 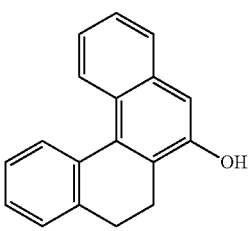 | 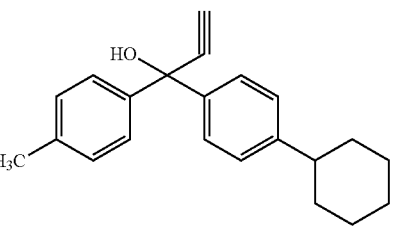 | 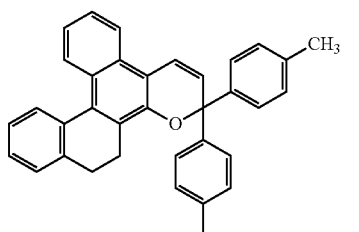 | 39 |
Ex.: Example TABLE 2
| Ex. No. | Raw materials Naphthol derivative | Propargyl alcohol derivative | Product | Yield (%) |
|---|---|---|---|---|
| 6 | 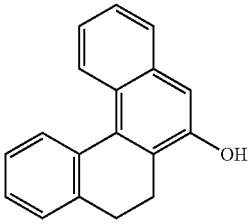 | 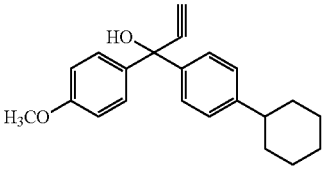 | 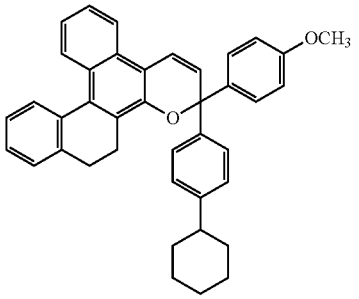 | 37 |
| 7 | 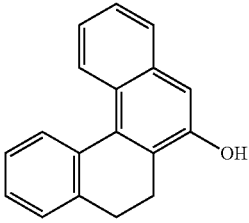 | 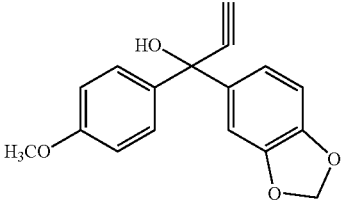 | 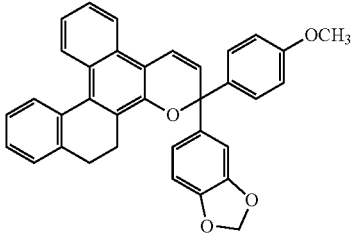 | 17 |
| 8 | 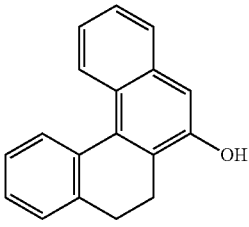 | 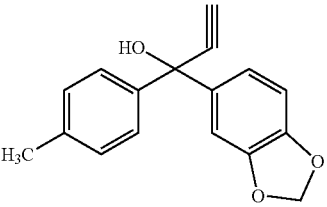 | 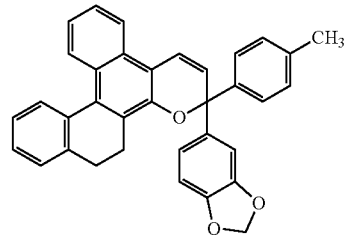 | 19 |
| 9 | 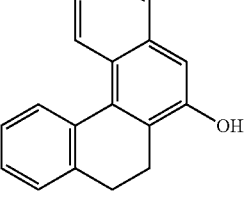 | 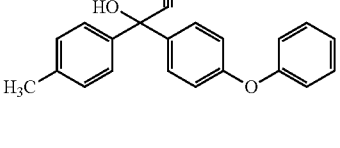 | 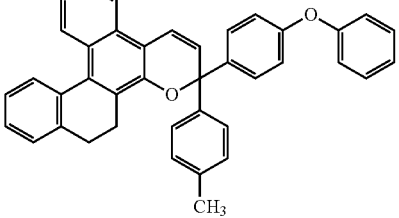 | 29 |
Ex.: Example
TABLE 3
| Ex. No. | Raw materials Naphthol derivative | Propargyl alcohol derivative | Product | Yield (%) |
|---|---|---|---|---|
| 10 | 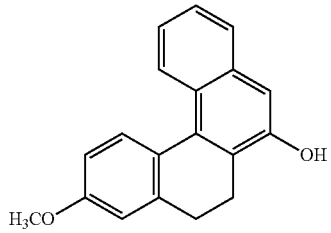 | 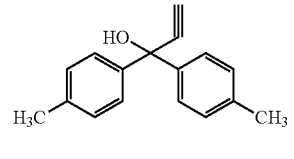 | 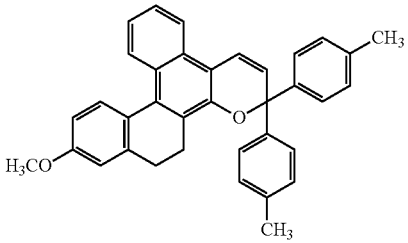 | 33 |

TABLE 3-continued
| Ex. No. | Naphthol derivative | Propargyl alcohol derivative | Product | Yield (%) |
|---|---|---|---|---|
| 11 | 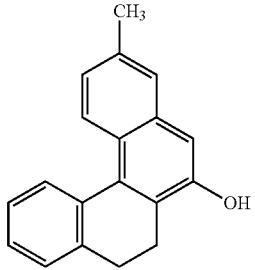 | 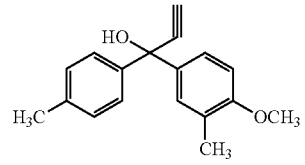 | 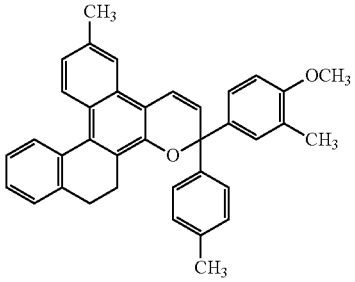 | 26 |
| 12 | 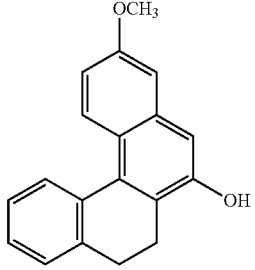 | 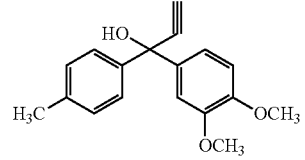 | 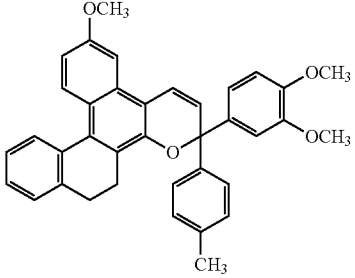 | 29 |
| 13 | 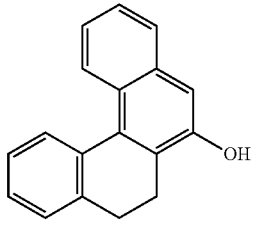 | 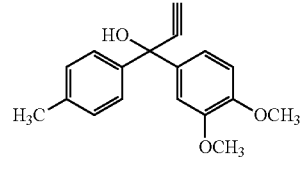 | 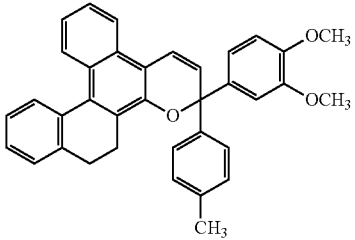 | 31 |
Ex.: Example
TABLE 4
| Ex. No. | Naphthol derivative | Propargyl alcohol derivative | Product | Yield (%) |
|---|---|---|---|---|
| 14 | 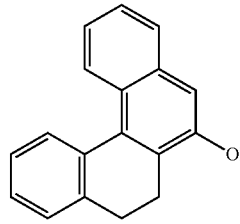 | 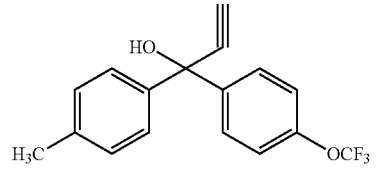 | 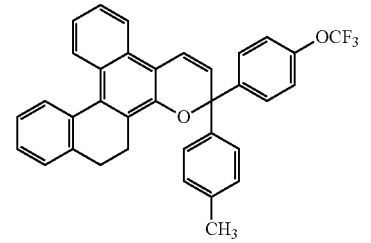 | 35 |

TABLE 4-continued

| Ex. No. | Raw materials | | Product | Yield (%) |
|---|---|---|---|---|
| | Naphthol derivative | Propargyl alcohol derivative | | |
| 15 | [structure] | [structure] | [structure] | 28 |
| 16 | [structure] | [structure] | [structure] | 25 |

Ex.: Example

TABLE 5

| Ex. No. | Elemental analysis value (%) | | | | | | $^1$H-NMR (NMR) |
|---|---|---|---|---|---|---|---|
| | Experimental value | | | Calculated value | | | |
| | C | H | O | C | H | O | |
| 2 | 87.41 | 5.99 | 6.60 | 87.47 | 5.87 | 6.66 | δ5.0-9.0 18H<br>δ0.5-4.0 10H |
| 3 | 90.32 | 6.27 | 3.41 | 90.34 | 6.32 | 3.34 | δ5.0-9.0 17H<br>δ0.5-4.0 13H |
| 4 | 87.32 | 6.17 | 6.51 | 87.42 | 6.11 | 6.47 | δ5.0-9.0 17H<br>δ0.5-4.0 13H |
| 5 | 90.14 | 6.83 | 3.03 | 90.19 | 6.81 | 3.00 | δ5.0-9.0 8H<br>δ0.5-4.0 18H |
| 6 | 87.49 | 6.59 | 5.92 | 87.56 | 6.61 | 5.83 | δ5.0-9.0 18H<br>δ0.5-4.0 18H |
| 7 | 82.22 | 5.14 | 12.64 | 82.33 | 5.13 | 12.53 | δ5.0-9.0 17H<br>δ0.5-4.0 9H |
| 8 | 84.95 | 5.29 | 9.76 | 85.00 | 5.30 | 9.70 | δ5.0-9.0 17H<br>δ0.5-4.0 9H |
| 9 | 88.51 | 5.55 | 5.94 | 88.53 | 5.57 | 5.90 | δ5.0-9.0 23H<br>δ0.5-4.0 7H |
| 10 | 87.35 | 6.13 | 6.52 | 87.42 | 6.11 | 6.47 | δ5.0-9.0 17H<br>δ0.5-4.0 13H |
| 11 | 87.41 | 6.28 | 6.31 | 87.37 | 6.34 | 6.29 | δ5.0-9.0 16H<br>δ0.5-4.0 16H |
| 12 | 82.15 | 5.99 | 11.86 | 82.20 | 5.97 | 11.84 | δ5.0-9.0 16H<br>δ0.5-4.0 16H |
| 13 | 84.80 | 5.94 | 9.26 | 84.68 | 5.92 | 9.40 | δ5.0-9.0 17H<br>δ0.5-4.0 13H |
| 14 | 78.62 | 4.73 | 5.99 | 78.64 | 4.71 | 5.99 | δ5.0-9.0 18H<br>δ0.5-4.0 7H |
| 15 | 91.20 | 5.77 | 3.03 | 91.22 | 5.74 | 3.04 | δ5.0-9.0 23H<br>δ0.5-4.0 7H |
| 16 | 88.55 | 5.74 | 5.71 | 88.46 | 5.79 | 5.75 | δ5.0-9.0 23H<br>δ0.5-4.0 9H |

Ex.: Example

Example 17

Evaluation of Physical Properties of Photochromic Cured Product Formed by Coating The chromene compound obtained in Example 1 was mixed with a photopolymerization initiator and polymerizable monomers, and the resulting mixture was applied to the surface of a lens substrate and exposed to ultraviolet light to observe the polymerization state of the coating film on the surface of the lens substrate. A photochromic curable composition comprising 2,2-bis(4-methacryloyloxypentaethoxyphenyl)propane, polyethylene glycol diacrylate (average molecular weight of 532), trimethylolpropane trimethacrylate, polyester oligomer hexaacrylate (EB-1830 of Daicel UCB Co., Ltd.) and glycidyl methacrylate as polymerizable monomers in a weight ratio of 50/10/10/10/10 part by mass was used. After 1 part by mass of the chromene compound obtained in Example 1 was added to and fully mixed with 90 parts by mass of a mixture of these radically polymerizable monomers, 0.3 part by mass of CGI1800 {a mixture of 1-hydroxycyclohexylphenyl ketone and bis(2,6-dimethoxybenzoyl)-2,4,4-trimethyl-pentyl phosphine oxide (weight ratio of 3:1)} as a photopolymerization initiator, 5 parts by mass of bis(1,2,2,6,6-pentamethyl-4-piperidyl)sebacate as a stabilizer, 7 parts by mass of γ-methacryloyloxypropyl trimethoxysilane as a silane coupling agent and 3 parts by mass of N-methyldiethanolamine were added to and fully mixed with the resulting mixture to obtain a photochromic curable composition.

About 2 g of the photochromic curable composition obtained by the above method was applied to the surface of a lens substrate (CR39: allyl resin plastic lens; refractive index of 1.50) with the 1H-DX2 spin coater of MIKASA Co., Ltd. The lens having a coated surface was exposed to light from a metal halide lamp having an output of 120 mW/cm² in a nitrogen gas atmosphere for 3 minutes to cure the coating film (an optical substrate (photochromic plastic lens) coated with a polymer film comprising the chromene compound dispersed therein was manufactured).

The following photochromic properties of the obtained photochromic plastic lens were evaluated.

[1] maximum absorption wavelength (λmax): This is the maximum absorption wavelength after color development obtained by means of the spectrophotometer (MCPD3000 instantaneous multi-channel photodetector) of Otsuka Denshi Kogyo Co., Ltd. The maximum absorption wavelength is connected with color at the time of color development.

[2] color optical density ($A_0$): difference between absorbance {ε(120)} after 120 seconds of exposure and absorbance ε(0) at the above maximum absorption wavelength. It can be said that as this value becomes larger, photochromic properties become better.

[3] fading half period [τ½ (sec.)]: time required for the reduction of the absorbance at the above maximum absorption wavelength of the sample to ½ of {ε(120)−ε(0)} when exposure is stopped after 120 seconds of exposure. As this time becomes shorter, the fading speed becomes higher.

[4] initial coloration due to thermochromism {ε(0)}: absorbance under no exposure at the above maximum absorption wavelength. For example, in an optical material such as a spectacle lens, it can be said that as this value becomes smaller, photochromic properties become better.

[5] yellow index (YI): To evaluate the yellow index after curing by polymerization, the color difference of the sample cured by polymerization was measured by means of the color difference meter (SM-4) of Suga Shikenki Co., Ltd. As the YI value becomes smaller, the transparency of the product (including a cured film) cured by polymerization becomes higher, or the deterioration degree of the evaluated compound becomes lower.

[6] residual rate ($A_{50}/A_0 \times 100$): The following deterioration promotion test was conducted to evaluate color development durability against exposure. That is, the deterioration of the obtained polymer (sample) was promoted by means of the X25 xenon weather meter of Suga Shikenki Co., Ltd. for 50 hours. Thereafter, the evaluation of the color optical density was carried out before and after the test to measure the color optical density before the test ($A_0$) and the color optical density after the test ($A_{50}$), and the ratio ($A_{50}/A_0$) was taken as the residual rate which is the index of color development durability. As the residual rate becomes higher, color development durability becomes higher.

These results are shown in Table 6.

Examples 18 to 32

Photochromic cured thin films (polymer films containing the chromene compound dispersed therein) were obtained in the same manner as in Example 17 except that the compounds obtained in Examples 2 to 16 were used as the chromene compound, and the characteristic properties of the obtained optical substrates (photochromic plastic lenses) were evaluated. The results are shown in Table 6. The compound No. corresponds to Example No. in Table 6. The chromene compounds of Examples 1 to 16 may be designated as compound Nos. 1 to 16.

TABLE 6

| Ex. No. | Compound No. | λmax (nm) | Color optical density $A_0$ | Fading half period τ½ (sec) | Initial coloration (thermochromism) ε(0) | Yellow index YI | Remaining rate ($A_{50}/A_0$) × 100 |
|---|---|---|---|---|---|---|---|
| 17 | 1 | 448 | 0.69 | 41 | 0.01 | 2.5 | 51% |
| 18 | 2 | 461 | 0.58 | 33 | 0.01 | 2.1 | 68% |
| 19 | 3 | 449 | 0.84 | 68 | 0.02 | 2.4 | 56% |
| 20 | 4 | 460 | 0.70 | 55 | 0.01 | 2.0 | 71% |
| 21 | 5 | 450 | 0.68 | 40 | 0.01 | 2.5 | 54% |
| 22 | 6 | 462 | 0.57 | 31 | 0.01 | 2.1 | 69% |
| 23 | 7 | 468 | 0.72 | 59 | 0.01 | 1.8 | 73% |
| 24 | 8 | 463 | 0.88 | 71 | 0.01 | 2.0 | 62% |
| 25 | 9 | 454 | 0.66 | 42 | 0.01 | 2.3 | 66% |
| 26 | 10 | 443 | 0.73 | 58 | 0.01 | 2.4 | 53% |
| 27 | 11 | 455 | 0.71 | 62 | 0.01 | 1.9 | 70% |
| 28 | 12 | 445 | 0.94 | 68 | 0.01 | 1.9 | 73% |
| 29 | 13 | 462 | 0.89 | 60 | 0.01 | 2.0 | 74% |
| 30 | 14 | 455 | 0.57 | 58 | 0.01 | 2.2 | 65% |
| 31 | 15 | 450 | 0.70 | 38 | 0.01 | 2.5 | 60% |
| 32 | 16 | 462 | 0.60 | 30 | 0.01 | 2.1 | 70% |

Ex.: Example

Comparative Examples 1 to 3

For comparison, photochromic cured thin films (polymer films containing a chromene compound dispersed therein) were obtained likewise from compounds represented by the following formula (A) (Comparative Example 1), the following formula (B) (Comparative Example 2) and the following formula (C) (Comparative Example 3), and the characteristic properties of the obtained optical substrates (photochromic plastic lenses) were evaluated. The results are shown in Table 7.

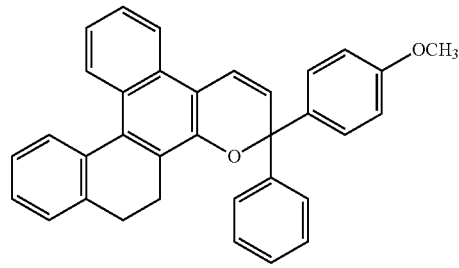

(A)

-continued

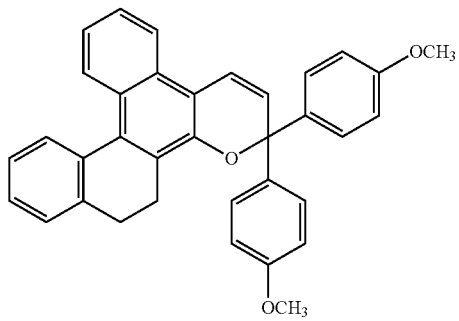

(B)

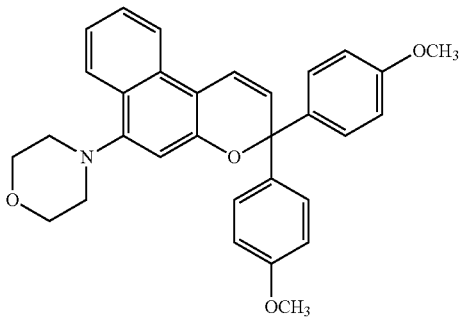

(C)

described hereinafter, and the photochromic properties of the obtained cured product were evaluated by the same methods as in Example 17.

The cured product was fabricated as follows. 0.04 part by mass of the chromene compound, 13 parts by mass of tetraethylene glycol dimethacrylate (trade name: NK Ester 4G, manufactured by Shin Nakamura Kagaku Co., Ltd.), 48 parts by mass of 2,2-bis[4-(methacryloxyethoxy)phenyl]propane (trade name: NK Ester BPE-100, manufactured by Shin Nakamura Kagaku Co., Ltd.), 2 parts by mass of polyethylene glycol monoaryl ether (trade name: Uniox PKA-5009, manufactured by Nichiyu Co., Ltd., Mw (molecular weight) of 550), 20 parts by mass of trimethylolpropane trimethacrylate (trade name: NK Ester TMPT, manufactured by Shin Nakamura Kagaku Co., Ltd.), 9 parts by mass of glycidyl methacrylate, 6 parts by mass of α-methylstyrene, 2 parts by mass of α-methylstyrene dimer and 1 part by mass of t-butylperoxy 2-ethyl hexanoate as a polymerization initiator were added and fully mixed together for 2 hours or longer, and the obtained photochromic curable composition was injected into a casting mold composed of a glass plate and a gasket (diameter of 7.3 cm) made of an ethylene-vinyl acetate copolymer to carry out cast polymerization. The polymerization was carried out in an air furnace by heating at 33° C. for 8 hours, from 33 to 40° C. over 4 hours (temperature elevation rate of 1.75° C./h), from 40 to 55° C. over 4 hours (temperature elevation rate of 1.25° C.) and from 55 to 90° C. over 2 hours (temperature elevation rate of 17.5° C./h). After the

TABLE 7

| Comparative Example No. | Compound No. | λmax (nm) | Color optical density $A_0$ | Fading half period $\tau^{1/2}$ (sec) | Initial coloration (thermochromism) $\epsilon(O)$ | Yellow index YI | Remaining rate $(A_{50}/A_0) \times 100$ |
|---|---|---|---|---|---|---|---|
| 1 | A | 457 | 0.56 | 36 | 0.01 | 8.0 | 4% |
| 2 | B | 473 | 0.41 | 19 | 0.01 | 1.9 | 70% |
| 3 | C | 454 | 0.79 | 48 | 0.06 | 5.2 | 64% |

In Comparative Example 1, though the color optical density and the fading half period were satisfactory, the yellow index after curing by polymerization was extremely large and the durability evaluated by means of the X25 xenon weather meter of Suga Shikenki Co., Ltd. was extremely low. In Comparative Example 2, though the yellow index after curing by polymerization was small and the durability evaluated by means of the X25 xenon weather meter of Suga Shikenki Co., Ltd. was high, the color optical density was low and the fading speed was high, which is not preferred for color control. In Comparative Example 3, though the color optical density was high and the fading speed was moderate, initial coloration was large. In contrast to this, in Examples 17 to 32 in which the chromene compound of the present invention was used, the yellow index after curing by polymerization was small, that is, photopolymerization resistance was high, the durability evaluated by means of the X25 xenon weather meter of Suga Shikenki Co., Ltd. was satisfactory, and the color optical density was high. Thus, they had excellent photochromic properties. Since the chromene compound of the present invention has high durability and an appropriate fading half period, it is easy to use it for color control.

Example 33

A photochromic cured product was obtained from the chromene compound (Chromene compound No. 1) of Example 1 by a polymerization method which will be composition was kept at 90° C. for 2 hours, the temperature was reduced to 80° C. over 1 hour (temperature reduction rate of 10° C./h). After the end of polymerization, the polymer was removed from the casting glass mold and heated at 110° C. in a heating oven for 2 hours to obtain a cured product. The obtained cured product (photochromic cured product having a thickness of 2 mm) was evaluated by the same methods as in Example 17 as described above. The absorbance due to thermochromism and the position of the absorption end of the ultraviolet absorption spectrum of the cured product were measured by the following methods. The results are shown in Table 8. Compound No. in Table 8 corresponds to Example No. In the above photochromic curable composition, the monomer composition (refractive index of cured product of 1.55) excluding the chromene compound may be simply referred to as "polymerization monomer (A)".

In the present invention, the absorbance due to thermochromism and the position of the absorption end of the ultraviolet absorption spectrum were obtained by measuring a photochromic cured product having a thickness of 2 mm obtained by curing a photochromic curable composition consisting of the above polymerization monomer (A) and a chromene compound under the above polymerization conditions.

1. Absorbance Due to Thermochromism

The cured product (thickness of 2 mm) obtained under the above conditions is first caused to develop color at room temperature as a sample so as to obtain its maximum absorption wavelength. Then, the absorbance under no exposure at the maximum absorption wavelength is measured at room temperature and taken as "absorbance due to thermochromism". This absorbance is measured by means of the spectrophotometer of Otsuka Denshi Kogyo Co., Ltd. (MCPD3000 instantaneous multi-channel photodetector). When the absorbance is 0.1 or less, a photochromic cured product which rarely experiences initial coloration is obtained and when the absorbance is 0.03 or less, a photochromic cured product having transparency is obtained.

2. Position of Absorption End of Ultraviolet Absorption Spectrum

After the cured product (thickness of 2 mm) obtained under the above conditions is kept in the dark for one day as a sample, its UV transmittance (T %) at 350 to 800 nm is measured by means of an ultraviolet-visible spectrophotometer (UV-2550 of Shimadzu Corporation) at room temperature. A tangent line is drawn on the obtained ultraviolet absorption curve to ensure that the transmittance (T %) of the ultraviolet absorption curve passes a point of 50% so as to obtain an absorption wavelength at which the transmittance (T %) of the tangent becomes 0 as the absorption end (absorption end of the UV spectrum). When the absorption end is at 380 to 430 nm, a photochromic cured product whose initial coloration is weak is obtained and when the absorption end is at 380 to 410 nm, a photochromic cured product having transparency is obtained.

Examples 34 to 48

Photochromic cured products were manufactured in the same manner as in Example 33 except that the chromene compound was changed as shown in Table 8. The results are shown in Table 8. Compound No. in Table 8 corresponds to Example No.

Example 49

A photochromic plastic lens was obtained in the same manner as in Example 17 except that 1.4 parts by mass of the chromene compound obtained in Example 1 and 1.8 parts by mass of a chromene compound (D) shown below were used. When light including ultraviolet light such as sunlight or light from a mercury lamp was applied to this photochromic lens, it developed a gray color. The evaluation results of the photochromic properties of the photochromic plastic lens are shown in Table 9.

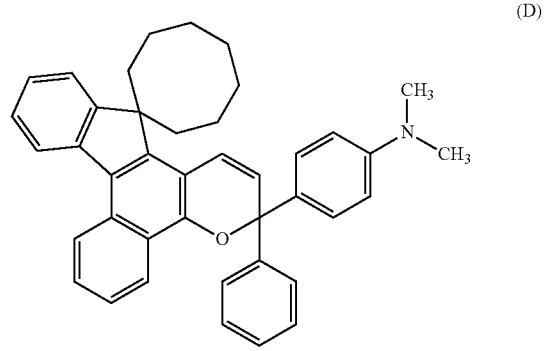

(D)

TABLE 8

| Example No. | Compound No. | λmax (nm) | Color optical density $A_0$ | Fading half period $\tau^{1/2}$ (sec) | Absorbance (thermochromism) $\epsilon(0)$ | Initial coloration (absorption end) nm | Yellow index YI | Remaining rate % $(A_{50}/A_0) \times 100$ |
|---|---|---|---|---|---|---|---|---|
| 33 | 1 | 449 | 0.91 | 63 | 0.01 | 396 | 3.4 | 91 |
| 34 | 2 | 462 | 0.88 | 54 | 0.01 | 396 | 3.2 | 93 |
| 35 | 3 | 450 | 0.95 | 75 | 0.01 | 396 | 3.4 | 91 |
| 36 | 4 | 460 | 0.92 | 64 | 0.01 | 396 | 3.0 | 93 |
| 37 | 5 | 450 | 0.89 | 56 | 0.01 | 396 | 3.4 | 90 |
| 38 | 6 | 463 | 0.76 | 48 | 0.01 | 396 | 3.5 | 91 |
| 39 | 7 | 469 | 0.94 | 63 | 0.01 | 396 | 3.1 | 94 |
| 40 | 8 | 463 | 1.11 | 73 | 0.01 | 396 | 2.8 | 92 |
| 41 | 9 | 455 | 0.91 | 65 | 0.01 | 396 | 3.0 | 92 |
| 42 | 10 | 444 | 0.93 | 65 | 0.01 | 398 | 3.3 | 89 |
| 43 | 11 | 454 | 0.91 | 59 | 0.01 | 399 | 3.4 | 92 |
| 44 | 12 | 463 | 1.18 | 69 | 0.01 | 399 | 3.0 | 93 |
| 45 | 13 | 462 | 1.11 | 65 | 0.01 | 396 | 2.9 | 93 |
| 46 | 14 | 455 | 0.87 | 58 | 0.01 | 396 | 3.2 | 92 |
| 47 | 15 | 449 | 0.91 | 45 | 0.01 | 396 | 3.4 | 90 |
| 48 | 16 | 463 | 0.75 | 42 | 0.01 | 396 | 3.0 | 90 |

Even the photochromic cured products having a thickness of 2 mm obtained in Examples 33 to 48 had the same excellent photochromic properties as the photochromic cured product obtained by coating. The evaluated chromenes (chromene compound Nos. 1 to 16) of Examples 1 to 16 had a low absorbance due to thermochromism of 0.01 and an absorption end at 396 to 399 nm. It was thus found that they were chromene compounds which rarely experienced initial coloration.

Example 50

A photochromic plastic lens was obtained in the same manner as in Example 49 except that 1.0 part by mass of the chromene compound obtained in Example 1, 0.9 parts by mass of the above chromene compound (D) and 0.6 part by mass of a chromene compound (E) shown below were used. When light including ultraviolet light such as sunlight or light from a mercury lamp was applied to this photochromic lens, it developed a brown color. The evaluation results of the photochromic properties of the photochromic plastic lens are shown in Table 9.

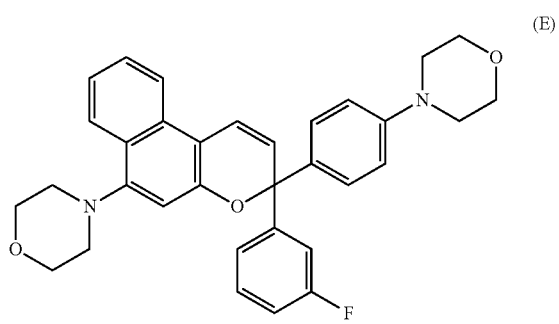

(E)

Example 51

A photochromic plastic lens was obtained in the same manner as in Example 49 except that 0.2 part by mass of the chromene compound obtained in Example 3, 0.4 part by mass of the chromene compound obtained in Example 13, 1.0 part by mass of the above chromene compound (D) and 1.0 part by mass of a chromene compound (F) shown below were used. When light including ultraviolet light such as sunlight or light from a mercury lamp was applied to this photochromic lens, it developed a gray color. The evaluation results of the photochromic properties of the photochromic plastic lens are shown in Table 9.

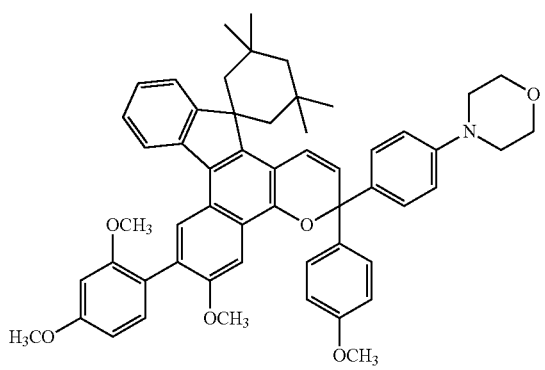

(F)

Example 52

A photochromic plastic lens was obtained in the same manner as in Example 49 except that 0.5 part by mass of the chromene compound obtained in Example 3, 0.5 part by mass of the chromene compound obtained in Example 13 and 1.5 parts by mass of the above chromene compound (F) were used. When light including ultraviolet light such as sunlight or light from a mercury lamp was applied to this photochromic lens, it developed a brown color. The evaluation results of the photochromic properties of the photochromic plastic lens are shown in Table 9.

The photochromic lenses of Examples 49 to 52 rarely experienced initial coloration and had high durability.

Comparative Example 4

For comparison, a photochromic plastic lens was obtained in the same manner as in Example 33 except that 1.8 parts by mass of the chromene compound (A) shown in Comparative Example 1 and 1.8 parts by mass of the above chromene compound (D) were used. When light including ultraviolet light such as sunlight or light from a mercury lamp was applied to this photochromic lens, it developed a gray color. However, when a durability test was carried out by using the X25 xenon weather meter of Suga Shikenki Co., Ltd., its color changed to blue.

Comparative Example 5

For comparison, a photochromic plastic lens was obtained in the same manner as in Example 33 except that 1.4 parts by mass of the chromene compound (C) shown in Comparative Example 3 and 1.8 parts by mass of the above chromene compound (D) were used. When light including ultraviolet light such as sunlight or light from a mercury lamp was applied to this photochromic lens, it developed a gray color. However, since its initial coloration before exposure was large, its indoor transmittance was low disadvantageously.

TABLE 9

| Example No. | λmax (nm) | Color optical density $A_0$ | Fading half period $\tau^{1/2}$ (sec) | Initial coloration (thermochromism) $\epsilon(0)$ | Yellow index YI | Remaining rate $(A_{50}/A_0) \times 100$ |
|---|---|---|---|---|---|---|
| 49 | 448 | 0.84 | 38 | 0.02 | 2.6 | 69% |
|  | 586 | 1.10 | 42 | 0.02 |  | 72% |
| 50 | 457 | 0.92 | 45 | 0.03 | 3.5 | 71% |
|  | 584 | 0.71 | 43 | 0.02 |  | 70% |
| 51 | 455 | 0.88 | 49 | 0.02 | 2.4 | 74% |
|  | 590 | 1.05 | 51 | 0.02 |  | 75% |
| 52 | 459 | 0.96 | 52 | 0.02 | 2.3 | 70% |
|  | 585 | 0.78 | 55 | 0.01 |  | 72% |

TABLE 9-continued

| Comparative Example No | λmax (nm) | Color optical density $A_0$ | Fading half period $\tau^{1/2}$ (sec) | Initial coloration (thermochromism) $\epsilon(0)$ | Yellow index YI | Residual rate $(A_{50}/A_0) \times 100$ |
|---|---|---|---|---|---|---|
| 4 | 458 | 0.77 | 51 | 0.02 | 9.1 | 8% |
|   | 586 | 1.08 | 40 | 0.01 |     | 68% |
| 5 | 453 | 0.93 | 41 | 0.08 | 7.1 | 70% |
|   | 586 | 1.12 | 45 | 0.03 |     | 71% |

Example 53

A photochromic plastic lens (photochromic cured product) was obtained in the same manner as in Example 33 except that 0.02 part by mass of the chromene compound obtained in Example 1 and 0.05 part by mass of a chromene compound (G) shown below were used. When light including ultraviolet light such as sunlight or light from a mercury lamp was applied to this photochromic plastic lens, it developed a gray color. The evaluation results of the photochromic properties are shown in Table 10.

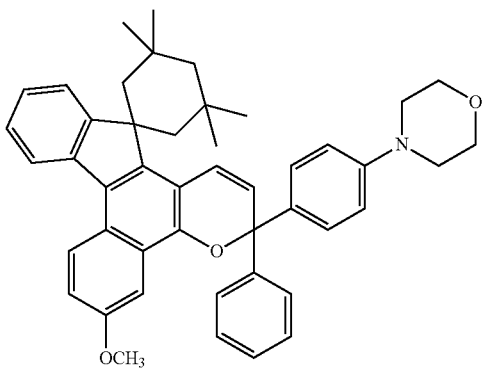

(G)

Example 54

A photochromic plastic lens (photochromic cured product) was obtained in the same manner as in Example 53 except that 0.02 part by mass of the chromene compound obtained in Example 3, 0.03 part by mass of the chromene compound obtained in Example 13 and 0.03 part by mass of the above chromene compound (G) were used. When light including ultraviolet light such as sunlight or light from a mercury lamp was applied to this photochromic plastic lens, it developed a brown color. The evaluation results of the photochromic properties are shown in Table 10.

Comparative Example 6

For comparison, a photochromic plastic lens (photochromic cured product) was obtained in the same manner as in Example 53 except that 0.06 part by mass of the chromene compound (B) shown in Comparative Example 2 and 0.03 part by mass of the above chromene compound (G) were used. When light including ultraviolet light such as sunlight or light from a mercury lamp was applied to this photochromic plastic lens, it developed a brown color.

TABLE 10

| Ex. No. | λmax (nm) | Color optical density $A_0$ | Fading half period $\tau^{1/2}$ (sec) | Absorbance (thermochromism) $\epsilon(0)$ | Yellow index YI |
|---|---|---|---|---|---|
| 53 | 448 | 0.79 | 57 | 0.02 | 3.8 |
|    | 584 | 0.96 | 65 | 0.02 |     |
| 54 | 456 | 0.95 | 63 | 0.02 | 3.1 |
|    | 585 | 0.72 | 65 | 0.01 |     |

| C. Ex. No. | λmax (nm) | Color optical density $A_0$ | Fading half period $\tau^{1/2}$ (sec) | Absorbance (thermochromism) $\epsilon(0)$ | Yellow index YI |
|---|---|---|---|---|---|
| 6 | 472 | 0.83 | 25 | 0.01 | 2.9 |
|   | 586 | 0.72 | 65 | 0.01 |     |

Ex.: Example
C. Ex.: Comparative Example

Since initial coloration (absorbance) was little and the fading half periods at two wavelengths were almost the same in Example 53 and Example 54, when exposure was stopped, they were excellent in terms of uniform color fading. Meanwhile, though initial coloration (absorbance) was little in Comparative Example 6 in which the comparative compound (B) was used, the difference in fading half period was large and therefore its color changed from brown to blue when exposure was stopped. This color nonuniformity at the time of fading is not preferred for the photochromic plastic lens.

Reference Examples 1 to 18

When the chromene compound of the present invention is used in a photochromic cured product, the chromene compound of the present invention may be used alone but to obtain a desired color, it is preferred that it should be used in combination with other photochromic compounds. As a matter of course, to obtain a photochromic cured product whose initial coloration is weak and having transparency, compounds whose initial coloration is weak must be used.

In the reference examples, the initial colorations (absorbances due to thermochromism, the absorption ends of the ultraviolet absorption spectra) of the chromene compounds represented by the following formulas 17 to 34 were investigated in detail by the same methods as in Example 33. The results are shown in Table 11. The maximum absorption wavelengths, color optical densities and fading speeds of the chromene compounds were evaluated as well. The results are shown in Table 11 (in the formulas, Me is a methyl group and iPr is an isopropyl group).

17
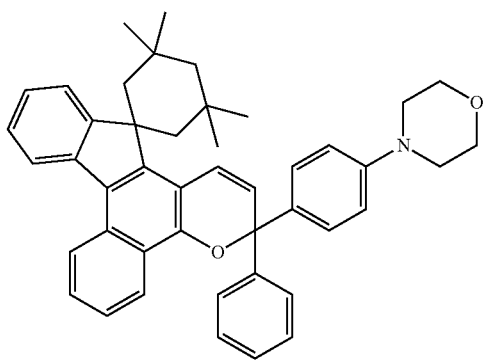
18
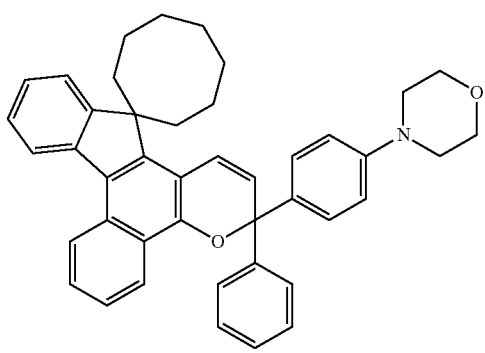
19
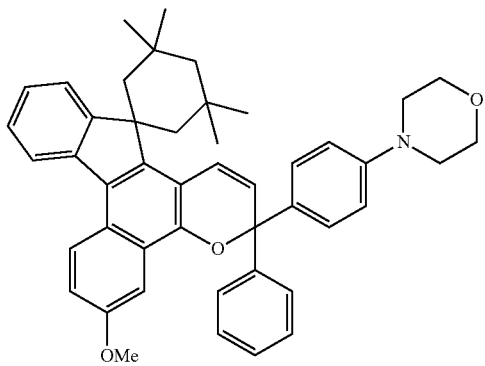
20
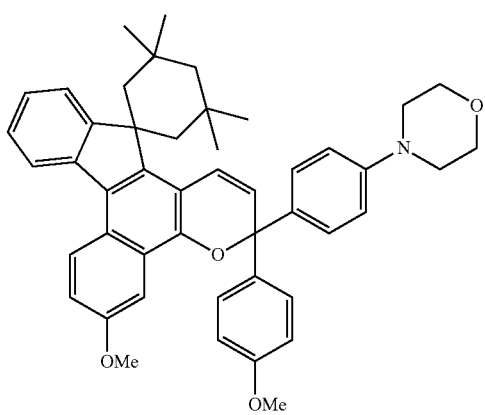
21
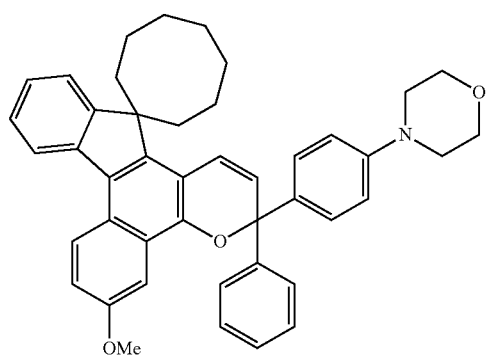
22
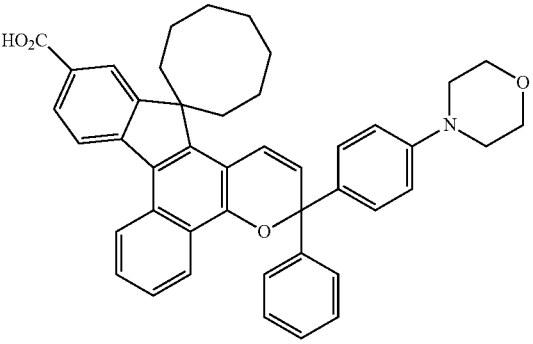
23
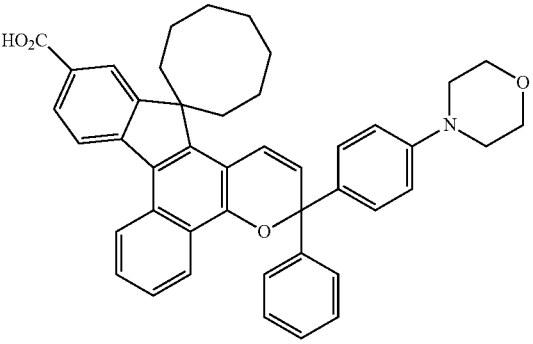
24

25
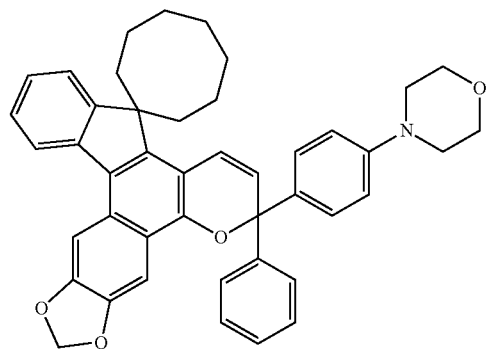
26
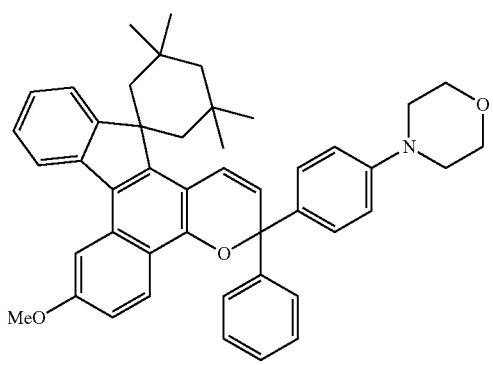
27
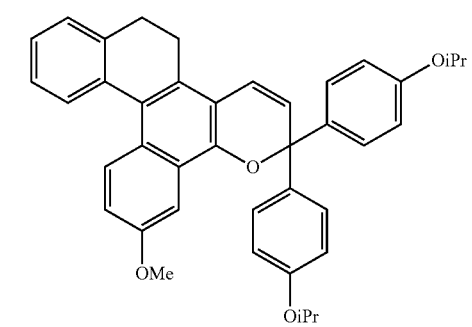
28
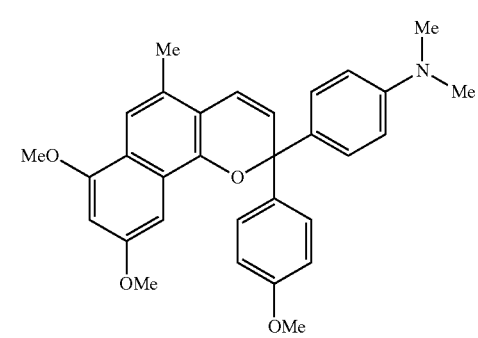
29
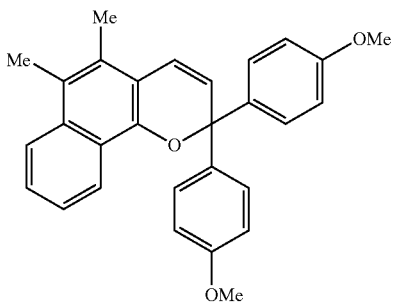
30
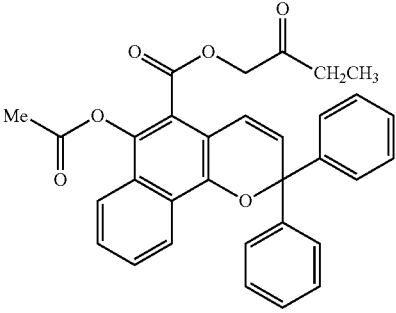
31
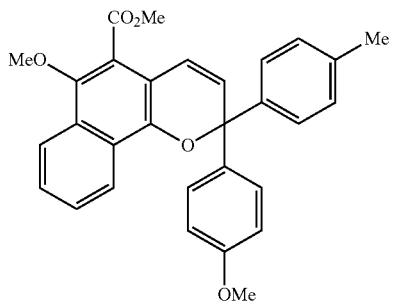
32
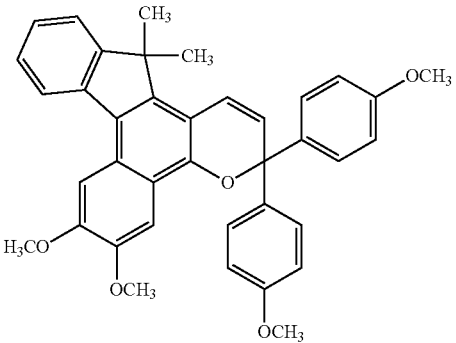
33
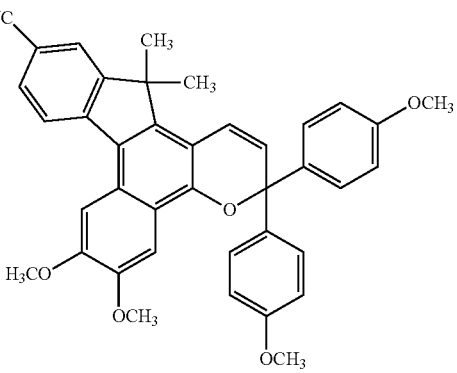

34

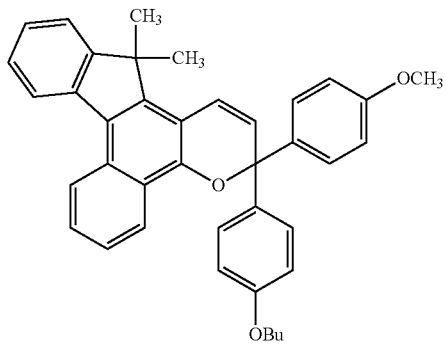

Examples 55 to 75

The chromene compounds (chromene compound Nos. 1 to 16) of Examples 1 to 16 of the present invention and the chromene compound Nos. 17 to 34 were mixed together in ratios shown in Tables 12 and 13 to obtain photochromic cured products. The characteristic properties of the obtained photochromic cured products were evaluated by the same methods as in Example 33. The evaluation results are shown in Table 14. The photochromic cured products were obtained by using the monomer composition shown in Example 33 as the polymerization monomer (A) and the same polymerization method as in Example 33. As the polymerization monomer (B), a monomer composition consisting of 45 parts by mass of tripropylene glycol dimethacrylate, parts by mass of urethane acrylate (trade name: EB8402, manufactured by

TABLE 11

| Reference Example No. | Chromene compound No. | Maximum absorption wavelength $\lambda$max (nm) | Color optical density Absorbance | Fading half period $\tau_{1/2}$ (sec) | Absorbance (thermochromism) $\epsilon(0)$ | Initial coloration (absorption end) nm |
|---|---|---|---|---|---|---|
| 1 | 17 | 564 | 0.84 | 39 | 0.01 | 396 |
| 2 | 18 | 564 | 1.15 | 74 | 0.01 | 396 |
| 3 | 19 | 477 | 0.46 | 63 | 0.02 | 406 |
|   |    | 579 | 0.86 |    |      |     |
| 4 | 20 | 471 | 0.44 | 72 | 0.02 | 406 |
|   |    | 591 | 0.61 |    |      |     |
| 5 | 21 | 477 | 0.63 | 118 | 0.02 | 406 |
|   |    | 579 | 1.24 |    |      |     |
| 6 | 22 | 572 | 0.38 | 28 | 0.01 | 392 |
| 7 | 23 | 572 | 0.35 | 26 | 0.02 | 392 |
| 8 | 24 | 560 | 0.45 | 35 | 0.01 | 392 |
| 9 | 25 | 477 | 0.81 | 100 | 0.01 | 396 |
|   |    | 580 | 0.9  |    |      |     |
| 10 | 26 | 470 | 0.41 | 51 | 0.01 | 391 |
|    |    | 554 | 0.84 |    |      |     |
| 11 | 27 | 443 | 0.73 | 68 | 0.02 | 396 |
|    |    | 569 | 0.78 |    |      |     |
| 12 | 28 | 489 | 0.57 | 73 | 0.01 | 385 |
|    |    | 580 | 0.9  |    |      |     |
| 13 | 29 | 503 | 0.8  | 70 | 0.01 | 372 |
| 14 | 30 | 464 | 0.55 | 85 | 0.01 | 375 |
| 15 | 31 | 482 | 0.52 | 69 | 0.01 | 369 |
| 16 | 32 | 455 | 1.11 | 150 | 0.01 | 400 |
|    |    | 576 | 0.71 |    |      |     |
| 17 | 33 | 458 | 0.67 | 95 | 0.02 | 395 |
|    |    | 574 | 0.43 |    |      |     |
| 18 | 34 | 572 | 0.81 | 74 | 0.01 | 396 |

The photochromic cured products comprising the compound Nos. 17 to 34 had a low absorbance of 0.01 to 0.02 and an absorption end at 406 nm or less. Therefore, it was found that the chromene compounds rarely experienced initial coloration. Further, they had sufficiently high color optical density and a practical fading speed of 150 seconds or less. The chromene compound Nos. 17 to 34 can be used as preferred chromene compounds which can provide a photochromic curable composition rarely experiencing initial coloration when mixed with the chromene compound of the present invention.

Daicel Sytec Co., Ltd.), 10 parts by mass of trimethylolpropane trimethacrylate, 10 parts by mass of tetraethylene glycol dimethacrylate, 3 parts by mass of glycidyl methacrylate and 2 parts by mass of α-methylstyrene dimer was used. A photochromic cured product was obtained by carrying out polymerization in the same manner as in Example 33 except that the monomer composition was changed and evaluated for its characteristic properties in the same manner as described above. In the case of the polymerization monomer (B), the cured product had a refractive index of 1.50. The results are shown in Table 14.

TABLE 12

| Example No. | | Photochromic compound | | | | | | Color |
|---|---|---|---|---|---|---|---|---|
| 55 | Compound No. | 1 | 17 | 18 | 19 | 21 | Polymerization monomer (A) | Gray |
| | Amount (parts by mass) | 0.015 | 0.01 | 0.005 | 0.04 | 0.005 | 100 | |
| 56 | Compound No. | 4 | 17 | 18 | 19 | 29 | Polymerization monomer (A) | Brown |
| | Amount (parts by mass) | 0.02 | 0.001 | 0.0075 | 0.03 | 0.004 | 100 | |
| 57 | Compound No. | 8 | 18 | 19 | 20 | 21 | Polymerization monomer (B) | Gray |
| | Amount (parts by mass) | 0.013 | 0.005 | 0.04 | 0.01 | 0.007 | 100 | |
| 58 | Compound No. | 11 | 18 | 19 | 21 | 29 | Polymerization monomer (B) | Brown |
| | Amount (parts by mass) | 0.02 | 0.01 | 0.03 | 0.0025 | 0.004 | 100 | |
| 59 | Compound No. | 3 | 22 | 18 | 19 | 21 | Polymerization monomer (A) | Gray |
| | Amount (parts by mass) | 0.015 | 0.02 | 0.005 | 0.04 | 0.005 | 100 | |
| 60 | Compound No. | 2 | 23 | 18 | 19 | 29 | Polymerization monomer (A) | Gray |
| | Amount (parts by mass) | 0.02 | 0.02 | 0.0075 | 0.03 | 0.004 | 100 | |
| 61 | Compound No. | 8 | 24 | 19 | 20 | 21 | Polymerization monomer (B) | Gray |
| | Amount (parts by mass) | 0.013 | 0.005 | 0.04 | 0.01 | 0.007 | 100 | |
| 62 | Compound No. | 5 | 17 | 18 | 25 | 21 | Polymerization monomer (A) | Gray |
| | Amount (parts by mass) | 0.015 | 0.01 | 0.005 | 0.04 | 0.005 | 100 | |
| 63 | Compound No. | 9 | 26 | 18 | 19 | 29 | Polymerization monomer (A) | Gray |
| | Amount (parts by mass) | 0.02 | 0.001 | 0.0075 | 0.03 | 0.004 | 100 | |

TABLE 13

| Example No. | | Photochromic compound | | | | Color |
|---|---|---|---|---|---|---|
| 64 | Compound No. | 6 | 27 | 29 | Polymerization monomer (A) | Brown |
| | Amount (parts by mass) | 0.015 | 0.03 | 0.01 | 100 | |
| 65 | Compound No. | 14 | 27 | 30 | Polymerization monomer (B) | Brown |
| | Amount (parts by mass) | 0.03 | 0.01 | 0.02 | 100 | |
| 66 | Compound No. | 10 | 27 | 31 | Polymerization monomer (A) | Brown |
| | Amount (parts by mass) | 0.015 | 0.03 | 0.01 | 100 | |
| 67 | Compound No. | 7 | 28 | 31 | Polymerization monomer (B) | Brown |
| | Amount (parts by mass) | 0.03 | 0.01 | 0.01 | 100 | |
| 68 | Compound No. | 12 | 29 | 32 | Polymerization monomer (A) | Brown |
| | Amount (parts by mass) | 0.015 | 0.01 | 0.02 | 100 | |
| 69 | Compound No. | 13 | 29 | 33 | Polymerization monomer (A) | Brown |
| | Amount (parts by mass) | 0.015 | 0.01 | 0.03 | 100 | |
| 70 | Compound No. | 15 | 29 | 34 | Polymerization monomer (A) | Gray |
| | Amount (parts by mass) | 0.015 | 0.01 | 0.03 | 100 | |
| 71 | Compound No. | 16 | 29 | 34 | Polymerization monomer (B) | Gray |
| | Amount (parts by mass) | 0.02 | 0.01 | 0.03 | 100 | |
| 72 | Compound No. | 4 | 29 | 33 | Polymerization monomer (B) | Brown |
| | Amount (parts by mass) | 0.02 | 0.01 | 0.03 | 100 | |

TABLE 14

| Ex. No. | Maximum absorption wavelength $\lambda$max (nm) | Color optical density Absorbance | Fading half period $\tau^{1}/_{2}$(sec) | Absorbance (thermochromism) $\varepsilon(0)$ | Initial coloration (absorption end) nm | Remaining rate $(A_{50}/A_0) \times 100$ | Yellow index YI | Color |
|---|---|---|---|---|---|---|---|---|
| 55 | 468 | 0.8 | 62 | 0.02 | 409 | 71 | 1.7 | Gray |
| | 576 | 1.31 | 65 | | | 72 | | |
| 56 | 456 | 1.61 | 60 | 0.02 | 404 | 69 | 3.1 | Brown |
| | 568 | 0.88 | 65 | | | 70 | | |

TABLE 14-continued

| Ex. No. | Maximum absorption wavelength λmax (nm) | Color optical density Absorbance | Fading half period τ½(sec) | Absorbance (thermochromism) ε(0) | Initial coloration (absorption end) nm | Remaining rate (A50/A0) × 100 | Yellow index YI | Color |
|---|---|---|---|---|---|---|---|---|
| 57 | 452 | 0.96 | 71 | 0.02 | 409 | 73 | 2.1 | Gray |
|  | 579 | 1.36 | 72 |  |  | 74 |  |  |
| 58 | 454 | 2.2 | 63 | 0.02 | 404 | 70 | 2.8 | Brown |
|  | 570 | 1.0 | 66 |  |  | 72 |  |  |
| 59 | 466 | 0.85 | 69 | 0.02 | 409 | 72 | 2.3 | Gray |
|  | 570 | 1.34 | 58 |  |  | 74 |  |  |
| 60 | 467 | 0.71 | 52 | 0.02 | 404 | 68 | 2.5 | Gray |
|  | 575 | 1.03 | 52 |  |  | 71 |  |  |
| 61 | 460 | 1.0 | 38 | 0.02 | 409 | 73 | 2.6 | Gray |
|  | 578 | 1.3 | 30 |  |  | 74 |  |  |
| 62 | 452 | 1.1 | 87 | 0.02 | 409 | 71 | 2.5 | Gray |
|  | 572 | 1.4 | 89 |  |  | 75 |  |  |
| 63 | 470 | 0.76 | 56 | 0.02 | 404 | 70 | 3.2 | Gray |
|  | 575 | 0.90 | 65 |  |  | 71 |  |  |
| 64 | 459 | 0.95 | 56 | 0.02 | 410 | 72 | 2.8 | Brown |
|  | 580 | 0.58 | 69 |  |  | 75 |  |  |
| 65 | 454 | 0.82 | 60 | 0.02 | 406 | 70 | 2.9 | Brown |
|  | 563 | 0.20 | 68 |  |  | 72 |  |  |
| 66 | 452 | 0.94 | 65 | 0.02 | 410 | 73 | 3 | Brown |
|  | 577 | 0.58 | 68 |  |  | 75 |  |  |
| 67 | 458 | 0.81 | 64 | 0.02 | 406 | 70 | 2.8 | Brown |
|  | 566 | 0.22 | 73 |  |  | 71 |  |  |
| 68 | 471 | 1.10 | 105 | 0.02 | 404 | 69 | 2.7 | Brown |
|  | 570 | 0.35 | 150 |  |  | 72 |  |  |
| 69 | 464 | 1.03 | 78 | 0.02 | 404 | 70 | 3.1 | Brown |
|  | 567 | 0.32 | 90 |  |  | 73 |  |  |
| 70 | 454 | 0.46 | 63 | 0.02 | 408 | 72 | 2.5 | Gray |
|  | 575 | 0.60 | 74 |  |  | 74 |  |  |
| 71 | 452 | 0.50 | 60 | 0.02 | 408 | 71 | 2.4 | Gray |
|  | 572 | 0.60 | 74 |  |  | 73 |  |  |
| 72 | 452 | 1.2 | 68 | 0.02 | 404 | 70 | 3.2 | Brown |
|  | 567 | 0.3 | 80 |  |  | 72 |  |  |

Ex: Example

As shown in Table 14, the photochromic cured product obtained by curing the chromene composition of the present invention has a low absorbance due to thermochromism of 0.02 and very rarely experiences initial coloration with an absorption end at 410 nm or less. The photochromic cured product can be advantageously used as a photochromic plastic lens.

Comparative Examples 7, 8, 9 and 10

The physical properties of photochromic cured products (Comparative Examples 7 and 8) were evaluated by carrying out the same operation as in Examples 55 and 56 except that the chromene compounds of the present invention in Examples 55 and 56 were substituted by the above chromene compound (C). The compositions of the chromene compositions are shown in Table 15, and the results of the photochromic properties are shown in Table 16. Further, the physical properties of photochromic cured products (Comparative Examples 9 and 10) were evaluated in the same manner as in Comparative Examples 7 and 8 except that the chromene compound No. 19 in Comparative Example was substituted by the following chromene compound (H). The results are shown in Tables 15 and 16. As supplementary information, the initial coloration characteristics of the chromene compound (C) and the chromene compound (H) were evaluated in the same manner as in Example 33, and the results are shown in Table 17.

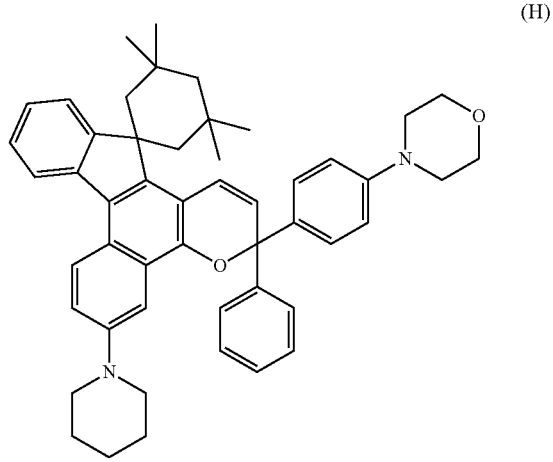

(H)

TABLE 15

| Comparative Example No. | | | Photochromic compound | | | | | Color |
|---|---|---|---|---|---|---|---|---|
| 7 | Compound No. | (C) | 17 | 18 | 19 | 21 | Polymerization monomer (A) | Gray |
| | Amount (parts by mass) | 0.015 | 0.01 | 0.005 | 0.04 | 0.005 | 100 | |
| 8 | Compound No. | (C) | 17 | 18 | 19 | 29 | Polymerization monomer (B) | Gray |
| | Amount (parts by mass) | 0.02 | 0.001 | 0.075 | 0.03 | 0.004 | 100 | |
| 9 | Compound No. | (C) | 17 | 18 | (H) | 21 | Polymerization monomer (A) | Blown |
| | Amount (parts by mass) | 0.015 | 0.01 | 0.005 | 0.04 | 0.005 | 100 | |
| 10 | Compound No. | (C) | 17 | 18 | (H) | 29 | Polymerization monomer (B) | Blown |
| | Amount (parts by mass) | 0.02 | 0.001 | 0.075 | 0.03 | 0.004 | 100 | |

TABLE 16

| Comparative Example No. | Maximum absorption wavelength $\lambda$max(nm) | Color optical density Absorbance | Fading half period $\tau_{1/2}$(sec) | Absorbance (thermochromism) $\epsilon(0)$ | Initial coloration (absorption end) nm | Remaining rate % $(A_{50}/A_0) \times 100$ | Color |
|---|---|---|---|---|---|---|---|
| 7 | 470 | 0.83 | 64 | 0.08 | 404 | 72 | Gray |
| | 572 | 1.36 | 60 | | | | |
| 8 | 462 | 0.78 | 58 | 0.08 | 404 | 70 | Gray |
| | 579 | 0.91 | 65 | | | | |
| 9 | 470 | 1.30 | 75 | 0.12 | 435 | 72 | Blown |
| | 590 | 1.24 | 76 | | | | |
| 10 | 462 | 1.25 | 70 | 0.12 | 435 | 70 | Blown |
| | 590 | 1.20 | 81 | | | | |

TABLE 17

| Compound No. | Absorbance (thermochromism) $\epsilon(0)$ | Initial coloration (absorption end) (nm) |
|---|---|---|
| (C) | 0.06 | 390 |
| (H) | 0.1 | 435 |

In Comparative Examples 7 and 8, initial coloration due to the absorption end was suppressed but absorbance due to thermochromism was large. Therefore, the photochromic cured products of these comparative examples were unsatisfactory as photochromic plastic lenses. In Comparative Examples 9 and 10, as absorbance due to thermochromism and initial coloration due to the absorption end were not suppressed, initial coloration was strong. Therefore, these photochromic cured products were not preferred as photochromic plastic lenses.

EFFECT OF THE INVENTION

The chromene compound of the present invention has at least two substituents except for the hydrogen atom at a specific position, whereby the obtained cured product does not yellow and can have a practical fading speed and excellent photochromic properties such as durability even when an energy lay such as ultraviolet radiation is applied to a photochromic curable composition comprising the chromene compound and polymerizable monomers.

As another effect, when a cured product is obtained by curing the photochromic curable composition comprising the chromene compound of the present invention and polymerizable monomers by a method other than photopolymerization, for example, heating, as the initial coloration of the photochromic curable composition is little, the cured product is transparent with high transmittance. When the photochromic composition is used in a plastic lens having a difference in thickness between the peripheral portion and the center portion, as the difference in transmittance between the peripheral portion and the center portion can be minimized, an appearance problem such as so-called "reverse panda phenomenon (white center portion and dark peripheral portion)" does not occur. Further, it can retain high transparency during its long-time use due to little yellowing at the time of deterioration by ultraviolet radiation and can be used for long time due to excellent repeat durability of its photochromic properties.

Therefore, the chromene compound of the present invention can be advantageously used in optical products having photochromic properties.

The invention claimed is:

1. A chromene composition comprising a chromene compound represented by the following formula (1) and a chromene compound having an absorbance due to thermochromism of 0.1 or less and the absorption end of its ultraviolet absorption spectrum at 380 to 430 nm and represented by the following formula (2):

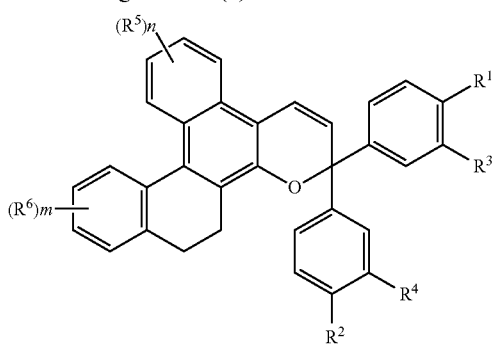

(1)

wherein $R^1$ and $R^2$ are each independently an alkyl group having 1 to 9 carbon atoms, cycloalkyl group having 3 to 12 carbon atoms, perfluoroalkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms or alkoxy group having 1 to 6 carbon atoms, with the proviso that $R^1$ and $R^2$ cannot be alkoxy groups having 1 to 6 carbon atoms at the same time;

$R^3$ and $R^4$ are each independently a hydrogen atom, hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms or aryloxy group having 6 to 10 carbon atoms;

$R^1$ and $R^3$ or $R^2$ and $R^4$ may be bonded together to form an alkylene group or alkylenedioxy group;

$R^5$ and $R^6$ are each independently a hydroxy group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, cyano group, nitro group, halogen atom, halogenoalkyl group having 1 to 6 carbon atoms or halogenoalkoxy group having 1 to 6 carbon atoms, and m and n are each independently an integer of 0 to 4;

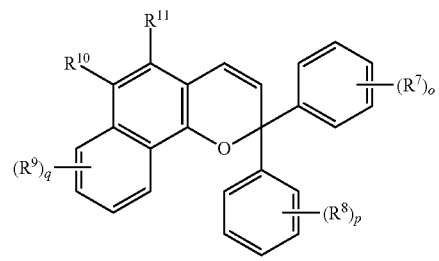

(2)

wherein $R^7$ and $R^8$ are each an alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring, or halogen atom, o and p are each an integer of 0 to 2, with the proviso that when o and p are each an integer of 1 to 2, $R^7$ and $R^8$, two $R^7$'s and two $R^8$'s may be the same or different;

$R^9$ is an alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, amino group, heterocyclic group having a nitrogen atom as a hetero atom and bonded to a benzene ring by the nitrogen atom bonded to the benzene ring, or halogen atom, and q is an integer of 0 to 2;

when q is 2, the both substituents may be bonded together to form an alkylenedioxy group having 1 to 8 carbon atoms;

$R^{10}$ and $R^{11}$ are bonded together to form a group represented by the following formula (3):

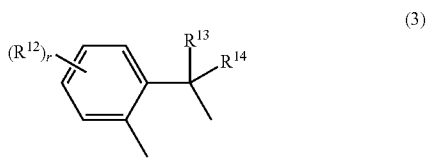

(3)

wherein $R^{12}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and r is an integer of 0 to 3;

$R^{13}$ and $R^{14}$ are each a hydrogen atom, hydroxyl group, alkyl group having 1 to 9 carbon atoms, cycloalkyl group having 3 to 12 carbon atoms, alkoxy group having 1 to 6 carbon atoms, halogenoalkyl group having 1 to 6 carbon atoms or halogenoalkoxy group having 1 to 6 carbon atoms, and further $R^{13}$ and $R^{14}$ may be bonded together to form a cyclic structure;

further $R^{10}$ and $R^{11}$ may be bonded together to form a group represented by the following formula (4):

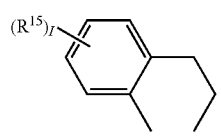

(4)

wherein $R^{15}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and l is an integer of 0 to 3.

2. A photochromic curable composition comprising the chromene composition of claim 1, and polymerizable monomers.

3. The photochromic curable composition according to claim 2, wherein the content of the chromene composition is 0.001 to 10 parts by mass based on 100 parts by mass of the polymerizable monomers.

4. The photochromic curable composition according to claim 3 which further comprises a photopolymerization initiator.

5. The photochromic curable composition according to claim 4 which further comprises a thermopolymerization initiator.

6. An optical product which comprises an optical substrate covered with a polymer film containing a chromene composition dispersed therein, wherein the chromene composition comprises a chromene compound represented by the following formula (1) and a chromene compound having an absorbance due to thermochromism of 0.1 or less and the absorption end of its ultraviolet absorption spectrum at 380 to 430 nm and represented by the following formula (2):

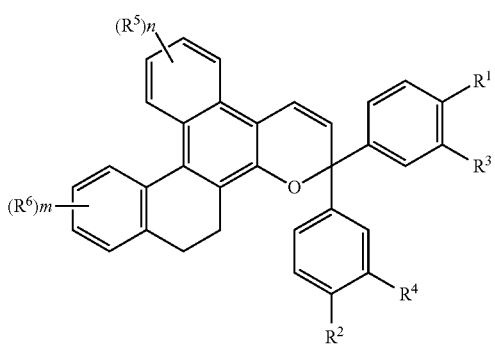
(1)

wherein $R^1$ and $R^2$ are each independently an alkyl group having 1 to carbon atoms, cycloalkyl group having 3 to 12 carbon atoms, perfluoroalkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms or alkoxy group having 1 to 6 carbon atoms, with the proviso that $R^1$ and $R^2$ cannot be alkoxy groups having 1 to 6 carbon atoms at the same time;

$R^3$ and $R^4$ are each independently a hydrogen atom, hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms or aryloxy group having 6 to 10 carbon atoms;

$R^1$ and $R^3$ or $R^2$ and $R^4$ may be bonded together to form an alkylene group or alkylenedioxy group;

$R^5$ and $R^6$ are each independently a hydroxy group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, cyano group, nitro group, halogen atom, halogenoalkyl group having 1 to 6 carbon atoms or halogenoalkoxy group having 1 to 6 carbon atoms, and m and n are each independently an integer of 0 to 4;

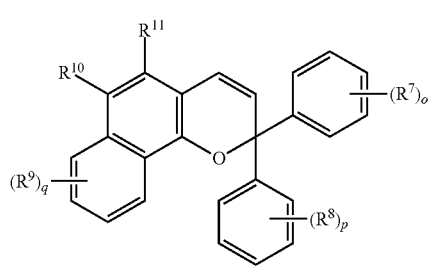
(2)

wherein $R^7$ and $R^8$ are each an alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring, or halogen atom, o and p are each an integer of 0 to 2, with the proviso that when o and p are each an integer of 1 to 2, $R^7$ and $R^8$, two $R^7$'s and two $R^8$'s may be the same or different;

$R^9$ is an alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, amino group, heterocyclic group having a nitrogen atom as a hetero atom and bonded to a benzene ring by the nitrogen atom bonded to the benzene ring, or halogen atom, and q is an integer of 0 to 2;

when q is 2, the both substituents may be bonded together to form an alkylenedioxy group having 1 to 8 carbon atoms;

$R^{10}$ and $R^{11}$ are bonded together to form a group represented by the following formula (3):

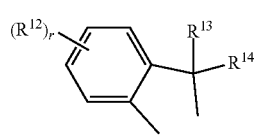
(3)

wherein $R^{12}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and r is an integer of 0 to 3;

$R^{13}$ and $R^{14}$ are each a hydrogen atom, hydroxyl group, alkyl group having 1 to 9 carbon atoms, cycloalkyl group having 3 to 12 carbon atoms, alkoxy group having 1 to 6 carbon atoms, halogenoalkyl group having 1 to 6 carbon atoms or halogenoalkoxy group having 1 to 6 carbon atoms, and further $R^{13}$ and $R^{14}$ may be bonded together to form a cyclic structure;

further $R^{10}$ and $R^{11}$ may be bonded together to form a group represented by the following formula (4):

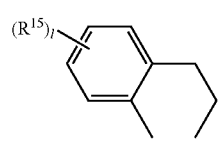
(4)

wherein $R^{15}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and l is an integer of 0 to 3, wherein the polymer film is a film cured by the optical radical polymerization of the photochromic curable composition of claim 5.

7. An optical product which comprises an optical substrate covered with a polymer film containing a chromene composition dispersed therein, wherein the chromene composition comprises a chromene compound represented by the following formula (1) and a chromene compound having an absorbance due to thermochromism of 0.1 or less and the absorption end of its ultraviolet absorption spectrum at 380 to 430 nm and represented by the following formula (2):

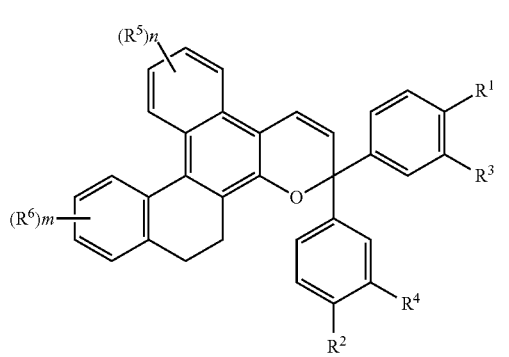

(1)

wherein $R^1$ and $R^2$ are each independently an alkyl group having 1 to 9 carbon atoms, cycloalkyl group having 3 to 12 carbon atoms, perfluoroalkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms or alkoxy group having 1 to 6 carbon atoms, with the proviso that $R^1$ and $R^2$ cannot be alkoxy groups having 1 to 6 carbon atoms at the same time;

$R^3$ and $R^4$ are each independently a hydrogen atom, hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms or aryloxy group having 6 to 10 carbon atoms;

$R^1$ and $R^3$ or $R^2$ and $R^4$ may be bonded together to form an alkylene group or alkylenedioxy group;

$R^5$ and $R^6$ are each independently a hydroxy group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, cyano group, nitro group, halogen atom, halogenoalkyl group having 1 to 6 carbon atoms or halogenoalkoxy group having 1 to 6 carbon atoms, and m and n are each independently an integer of 0 to 4;

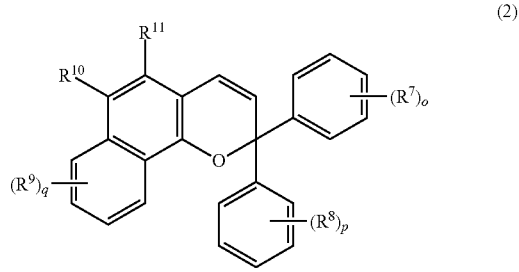

(2)

wherein $R^7$ and $R^8$ are each an alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring, or halogen atom, o and p are each an integer of 0 to 2, with the proviso that when o and p are each an integer of 1 to 2, $R^7$ and $R^8$, two $R^7$'s and two $R^8$'s may be the same or different;

$R^9$ is an alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, amino group, heterocyclic group having a nitrogen atom as a hetero atom and bonded to a benzene ring by the nitrogen atom bonded to the benzene ring, or halogen atom, and q is an integer of 0 to 2;

when q is 2, the both substituents may be bonded together to form an alkylenedioxy group having 1 to 8 carbon atoms;

$R^{10}$ and $R^{11}$ are bonded together to form a group represented by the following formula (3):

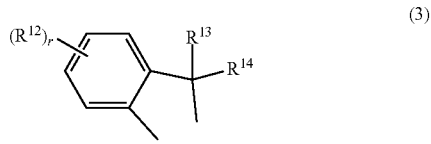

(3)

wherein $R^{12}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and r is an integer of 0 to 3;

$R^{13}$ and $R^{14}$ are each a hydrogen atom, hydroxyl group, alkyl group having 1 to 9 carbon atoms, cycloalkyl group having 3 to 12 carbon atoms, alkoxy group having 1 to 6 carbon atoms, halogenoalkyl group having 1 to 6 carbon atoms or halogenoalkoxy group having 1 to 6 carbon atoms, and further $R^{13}$ and $R^{14}$ may be bonded together to form a cyclic structure;

further $R^{10}$ and $R^{11}$ may be bonded together to form a group represented by the following formula (4):

(4)

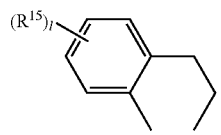

wherein $R^{15}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and l is an integer of 0 to 3, wherein the polymer film is a film cured by the optical radical polymerization of the photochromic curable composition of claim 4.

8. The photochromic curable composition according to claim 3 which further comprises a thermopolymerization initiator.

9. An optical product which comprises an optical substrate covered with a polymer film containing a chromene composition dispersed therein, wherein the chromene composition comprises a chromene compound represented by the following formula (1) and a chromene compound having an absorbance due to thermochromism of 0.1 or less and the absorption end of its ultraviolet absorption spectrum at 380 to 430 nm and represented by the following formula (2):

(1)

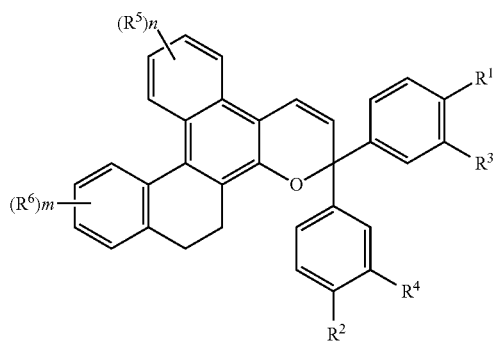

wherein $R^1$ and $R^2$ are each independently an alkyl group having 1 to 9 carbon atoms, cycloalkyl group having 3 to 12 carbon atoms, perfluoroalkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms or alkoxy group having 1 to 6 carbon atoms, with the proviso that $R^1$ and $R^2$ cannot be alkoxy groups having 1 to 6 carbon atoms at the same time;

$R^3$ and $R^4$ are each independently a hydrogen atom, hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms or aryloxy group having 6 to 10 carbon atoms;

$R^1$ and $R^3$ or $R^2$ and $R^4$ may be bonded together to form an alkylene group or alkylenedioxy group;

$R^5$ and $R^6$ are each independently a hydroxy group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, cyano group, nitro group, halogen atom, halogenoalkyl group having 1 to 6 carbon atoms or halogenoalkoxy group having 1 to 6 carbon atoms, and m and n are each independently an integer of 0 to 4;

(2)

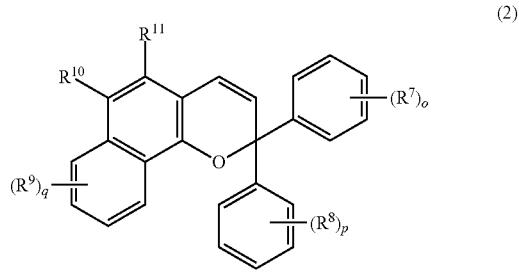

wherein $R^7$ and $R^8$ are each an alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring, or halogen atom, o and p are each an integer of 0 to 2, with the proviso that when o and p are each an integer of 1 to 2, $R^7$ and $R^8$, two $R^7$'s and two $R^8$'s may be the same or different;

$R^9$ is an alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, amino group, heterocyclic group having a nitrogen atom as a hetero atom and bonded to a benzene ring by the nitrogen atom bonded to the benzene ring, or halogen atom, and q is an integer of 0 to 2;

when q is 2, the both substituents may be bonded together to form an alkylenedioxy group having 1 to 8 carbon atoms;

$R^{10}$ and $R^{11}$ are bonded together to form a group represented by the following formula (3):

(3)

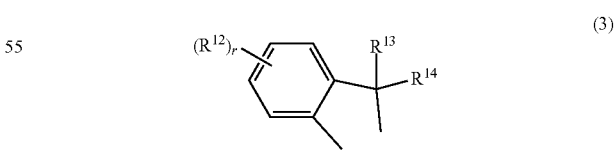

wherein $R^{12}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and r is an integer of 0 to 3;

$R^{13}$ and $R^{14}$ are each a hydrogen atom, hydroxyl group, alkyl group having 1 to 9 carbon atoms, cycloalkyl group having 3 to 12 carbon atoms, alkoxy group having 1 to 6 carbon atoms, halogenoalkyl group having 1 to 6 carbon atoms or halogenoalkoxy group having 1 to 6 carbon atoms, and further $R^{13}$ and $R^{14}$ may be bonded together to form a cyclic structure;

further $R^{10}$ and $R^{11}$ may be bonded together to form a group represented by the following formula (4):

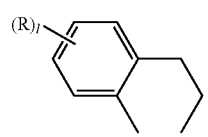

(4)

wherein $R^{15}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and l is an integer of 0 to 3, wherein the polymer film is a film cured by the optical radical polymerization of the photochromic curable composition of claim 8.

10. An optical product which comprises an optical substrate covered with a polymer film containing a chromene composition dispersed therein, wherein the chromene composition comprises a chromene compound represented by the following formula (1) and a chromene compound having an absorbance due to thermochromism of 0.1 or less and the absorption end of its ultraviolet absorption spectrum at 380 to 430 nm and represented by the following formula (2):

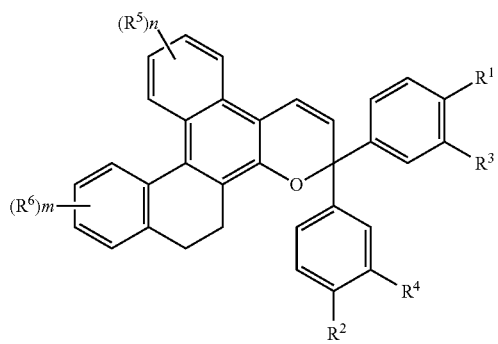

(1)

wherein $R^1$ and $R^2$ are each independently an alkyl group having 1 to carbon atoms, cycloalkyl group having 3 to 12 carbon atoms, perfluoroalkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms or alkoxy group having 1 to 6 carbon atoms, with the proviso that $R^1$ and $R^2$ cannot be alkoxy groups having 1 to 6 carbon atoms at the same time;

$R^3$ and $R^4$ are each independently a hydrogen atom, hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms or aryloxy group having 6 to 10 carbon atoms;

$R^1$ and $R^3$ or $R^2$ and $R^4$ may be bonded together to form an alkylene group or alkylenedioxy group;

$R^5$ and $R^6$ are each independently a hydroxy group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, cyano group, nitro group, halogen atom, halogenoalkyl group having 1 to 6 carbon atoms or halogenoalkoxy group having 1 to 6 carbon atoms, and m and n are each independently an integer of 0 to 4;

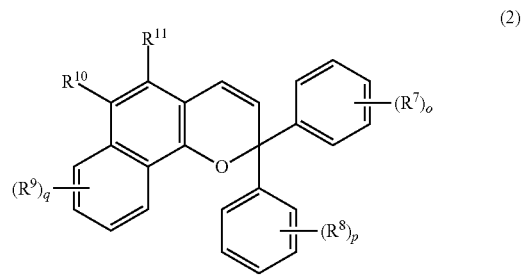

(2)

wherein $R^7$ and $R^8$ are each an alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring, or halogen atom, o and p are each an integer of 0 to 2, with the proviso that when o and p are each an integer of 1 to 2, $R^7$ and $R^8$, two $R^7$'s and two $R^8$'s may be the same or different;

$R^9$ is an alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, amino group, heterocyclic group having a nitrogen atom as a hetero atom and bonded to a benzene ring by the nitrogen atom bonded to the benzene ring, or halogen atom, and q is an integer of 0 to 2;

when q is 2, the both substituents may be bonded together to form an alkylenedioxy group having 1 to 8 carbon atoms;

$R^{10}$ and $R^{11}$ are bonded together to form a group represented by the following formula (3):

its ultraviolet absorption spectrum at 380 to 430 nm and represented by the following formula (2):

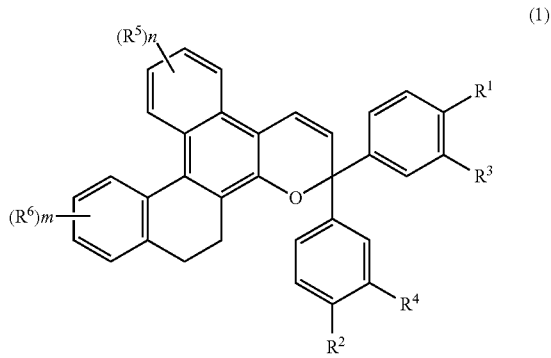

(1)

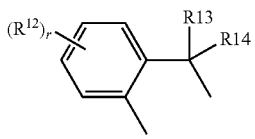

(3)

wherein R¹ and R² are each independently an alkyl group having 1 to 9 carbon atoms, cycloalkyl group having 3 to 12 carbon atoms, perfluoroalkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms or alkoxy group having 1 to 6 carbon atoms, with the proviso that R¹ and R² cannot be alkoxy groups having 1 to 6 carbon atoms at the same time;

wherein R¹² is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and r is an integer of 0 to 3;

R³ and R⁴ are each independently a hydrogen atom, hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms or aryloxy group having 6 to 10 carbon atoms;

R¹³ and R¹⁴ are each a hydrogen atom, hydroxyl group, alkyl group having 1 to 9 carbon atoms, cycloalkyl group having 3 to 12 carbon atoms, alkoxy group having 1 to 6 carbon atoms, halogenoalkyl group having 1 to 6 carbon atoms or halogenoalkoxy group having 1 to 6 carbon atoms, and further R¹³ and R¹⁴ may be bonded together to form a cyclic structure;

R¹ and R³ or R² and R⁴ may be bonded together to form an alkylene group or alkylenedioxy group;

R⁵ and R⁶ are each independently a hydroxy group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, cyano group, nitro group, halogen atom, halogenoalkyl group having 1 to 6 carbon atoms or halogenoalkoxy group having 1 to 6 carbon atoms, and m and n are each independently an integer of 0 to 4;

further R¹⁰ and R¹¹ may be bonded together to form a group represented by the following formula (4):

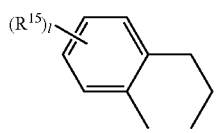

(4)

wherein R¹⁵ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and l is an integer of 0 to 3, wherein the polymer film is a film cured by the optical radical polymerization of the photochromic curable composition of claim 3.

11. The photochromic curable composition according to claim 2 which further comprises a photopolymerization initiator.

12. The photochromic curable composition according to claim 11 which further comprises a thermopolymerization initiator.

13. An optical product which comprises an optical substrate covered with a polymer film containing a chromene composition dispersed therein, wherein the chromene composition comprises a chromene compound represented by the following formula (1) and a chromene compound having an absorbance due to thermochromism of 0.1 or less and the absorption end of

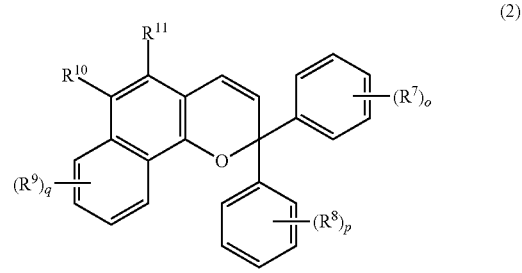

(2)

wherein R⁷ and R⁸ are each an alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring, or halogen atom, o and p are each an integer of 0 to 2, with the proviso that when o and p are each an integer of 1 to 2, $R^7$ and $R^8$, two $R^7$'s and two $R^8$'s may be the same or different;

$R^9$ is an alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, amino group, heterocyclic group having a nitrogen atom as a hetero atom and bonded to a benzene ring by the nitrogen atom bonded to the benzene ring, or halogen atom, and q is an integer of 0 to 2;

when q is 2, the both substituents may be bonded together to form an alkylenedioxy group having 1 to 8 carbon atoms;

$R^{10}$ and $R^{11}$ are bonded together to form a group represented by the following formula (3):

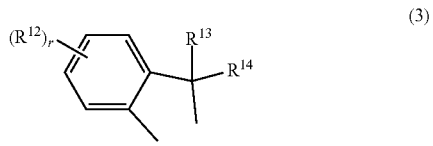

wherein $R^{12}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and r is an integer of 0 to 3;

$R^{13}$ and $R^{14}$ are each a hydrogen atom, hydroxyl group, alkyl group having 1 to 9 carbon atoms, cycloalkyl group having 3 to 12 carbon atoms, alkoxy group having 1 to 6 carbon atoms, halogenoalkyl group having 1 to 6 carbon atoms or halogenoalkoxy group having 1 to 6 carbon atoms, and further $R^{13}$ and $R^{14}$ may be bonded together to form a cyclic structure;

further $R^{10}$ and $R^{11}$ may be bonded together to form a group represented by the following formula (4):

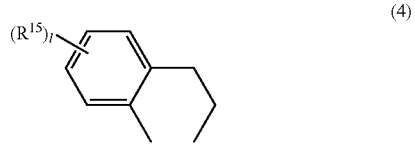

wherein $R^{15}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and l is an integer of 0 to 3, wherein the polymer film is a film cured by the optical radical polymerization of the photochromic curable composition of claim 12.

14. An optical product which comprises an optical substrate covered with a polymer film containing a chromene composition dispersed therein, wherein the chromene composition comprises a chromene compound represented by the following formula (1) and a chromene compound having an absorbance due to thermochromism of 0.1 or less and the absorption end of its ultraviolet absorption spectrum at 380 to 430 nm and represented by the following formula (2):

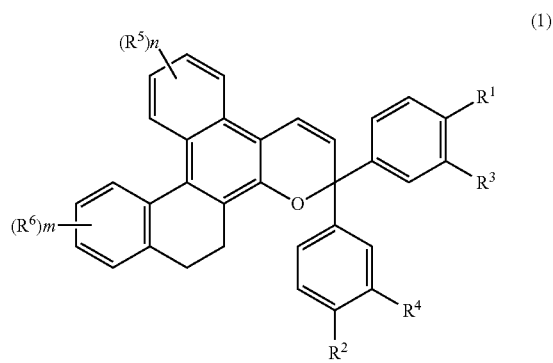

wherein $R^1$ and $R^2$ are each independently an alkyl group having 1 to 9 carbon atoms, cycloalkyl group having 3 to 12 carbon atoms, perfluoroalkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms or alkoxy group having 1 to 6 carbon atoms, with the proviso that $R^1$ and $R^2$ cannot be alkoxy groups having 1 to 6 carbon atoms at the same time;

$R^3$ and $R^4$ are each independently a hydrogen atom, hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms or aryloxy group having 6 to 10 carbon atoms;

$R^1$ and $R^3$ or $R^2$ and $R^4$ may be bonded together to form an alkylene group or alkylenedioxy group;

$R^5$ and $R^6$ are each independently a hydroxy group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, cyano group, nitro group, halogen atom, halogenoalkyl group having 1 to 6 carbon atoms or halogenoalkoxy group having 1 to 6 carbon atoms, and m and n are each independently an integer of 0 to 4;

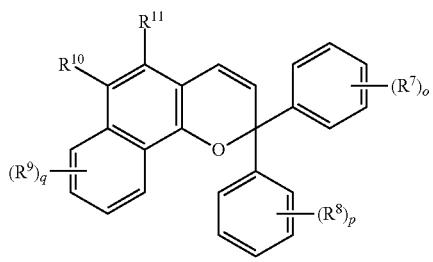

(2)

wherein $R^7$ and $R^8$ are each an alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring, or halogen atom, o and p are each an integer of 0 to 2, with the proviso that when o and p are each an integer of 1 to 2, $R^7$ and $R^8$, two $R^7$'s and two $R^8$'s may be the same or different;

$R^9$ is an alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, amino group, heterocyclic group having a nitrogen atom as a hetero atom and bonded to a benzene ring by the nitrogen atom bonded to the benzene ring, or halogen atom, and q is an integer of 0 to 2;

when q is 2, the both substituents may be bonded together to form an alkylenedioxy group having 1 to 8 carbon atoms;

$R^{10}$ and $R^{11}$ are bonded together to form a group represented by the following formula (3):

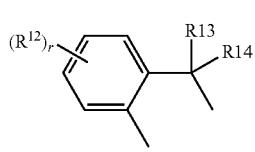

(3)

wherein $R^{12}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and r is an integer of 0 to 3;

$R^{13}$ and $R^{14}$ are each a hydrogen atom, hydroxyl group, alkyl group having 1 to 9 carbon atoms, cycloalkyl group having 3 to 12 carbon atoms, alkoxy group having 1 to 6 carbon atoms, halogenoalkyl group having 1 to 6 carbon atoms or halogenoalkoxy group having 1 to 6 carbon atoms, and further $R^{13}$ and $R^{14}$ may be bonded together to form a cyclic structure;

further $R^{10}$ and $R^{11}$ may be bonded together to form a group represented by the following formula (4):

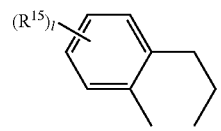

(4)

wherein $R^{15}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and l is an integer of 0 to 3, wherein the polymer film is a film cured by the optical radical polymerization of the photochromic curable composition of claim 11.

15. The photochromic curable composition according to claim 2 which further comprises a thermopolymerization initiator.

16. An optical product which comprises an optical substrate covered with a polymer film containing a chromene composition dispersed therein, wherein the chromene composition comprises a chromene compound represented by the following formula (1) and a chromene compound having an absorbance due to thermochromism of 0.1 or less and the absorption end of its ultraviolet absorption spectrum at 380 to 430 nm and represented by the following formula (2):

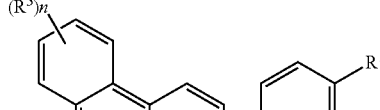

(1)

wherein $R^1$ and $R^2$ are each independently an alkyl group having 1 to 9 carbon atoms, cycloalkyl group having 3 to 12 carbon atoms, perfluoroalkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms or alkoxy group having 1 to 6 carbon atoms, with the proviso that $R^1$ and $R^2$ cannot be alkoxy groups having 1 to 6 carbon atoms at the same time;

$R^3$ and $R^4$ are each independently a hydrogen atom, hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms or aryloxy group having 6 to 10 carbon atoms;

$R^1$ and $R^3$ or $R^2$ and $R^4$ may be bonded together to form an alkylene group or alkylenedioxy group;

$R^5$ and $R^6$ are each independently a hydroxy group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, cyano group, nitro group, halogen atom, halogenoalkyl group having 1 to 6 carbon atoms or halogenoalkoxy group having 1 to 6 carbon atoms, and m and n are each independently an integer of 0 to 4;

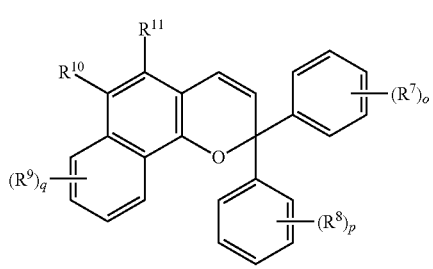

(2)

wherein $R^7$ and $R^8$ are each an alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring, or halogen atom, o and p are each an integer of 0 to 2, with the proviso that when o and p are each an integer of 1 to 2, $R^7$ and $R^8$, two $R^7$'s and two $R^8$'s may be the same or different;

$R^9$ is an alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, amino group, heterocyclic group having a nitrogen atom as a hetero atom and bonded to a benzene ring by the nitrogen atom bonded to the benzene ring, or halogen atom, and q is an integer of 0 to 2;

when q is 2, the both substituents may be bonded together to form an alkylenedioxy group having 1 to 8 carbon atoms;

$R^{10}$ and $R^{11}$ are bonded together to form a group represented by the following formula (3):

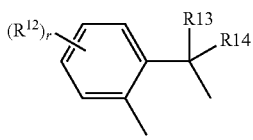

(3)

wherein $R^{12}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and r is an integer of 0 to 3;

$R^{13}$ and $R^{14}$ are each a hydrogen atom, hydroxyl group, alkyl group having 1 to 9 carbon atoms, cycloalkyl group having 3 to 12 carbon atoms, alkoxy group having 1 to 6 carbon atoms, halogenoalkyl group having 1 to 6 carbon atoms or halogenoalkoxy group having 1 to 6 carbon atoms, and further $R^{13}$ and $R^{14}$ may be bonded together to form a cyclic structure;

further $R^{10}$ and $R^{11}$ may be bonded together to form a group represented by the following formula (4):

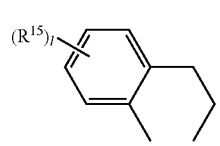

(4)

wherein $R^{15}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and l is an integer of 0 to 3, wherein the polymer film is a film cured by the optical radical polymerization of the photochromic curable composition of claim 15.

17. An optical product which comprises an optical substrate covered with a polymer film containing a chromene composition dispersed therein, wherein the chromene composition comprises a chromene compound represented by the following formula (1) and a chromene compound having an absorbance due to thermochromism of 0.1 or less and the absorption end of its ultraviolet absorption spectrum at 380 to 430 nm and represented by the following formula (2):

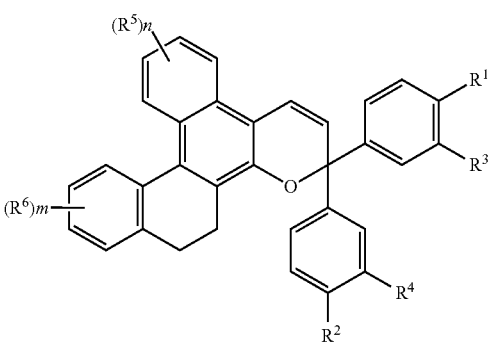

(1)

wherein $R^1$ and $R^2$ are each independently an alkyl group having 1 to 9 carbon atoms, cycloalkyl group having 3 to 12 carbon atoms, perfluoroalkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms or alkoxy group having 1 to 6 carbon atoms, with the proviso that $R^1$ and $R^2$ cannot be alkoxy groups having 1 to 6 carbon atoms at the same time;

$R^3$ and $R^4$ are each independently a hydrogen atom, hydroxyl group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms or aryloxy group having 6 to 10 carbon atoms;

$R^1$ and $R^3$ or $R^2$ and $R^4$ may be bonded together to form an alkylene group or alkylenedioxy group;

$R^5$ and $R^6$ are each independently a hydroxy group, alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, cyano group, nitro group, halogen atom, halogenoalkyl group having 1 to 6 carbon atoms or halogenoalkoxy group having 1 to 6 carbon atoms, and m and n are each independently an integer of 0 to 4;

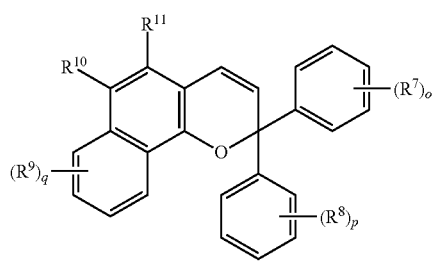

(2)

wherein $R^7$ and $R^8$ are each an alkyl group having 1 to 9 carbon atoms, alkoxy group having 1 to 6 carbon atoms, aryl group having 6 to 10 carbon atoms, amino group, heterocyclic group having a nitrogen atom as a hetero atom and bonded to a benzene ring by the nitrogen atom bonded to the benzene ring, or halogen atom, o and p are each an integer of 0 to 2, with the proviso that when o and p are each an integer of 1 to 2, $R^7$ and $R^8$, two $R^7$'s and two $R^8$'s may be the same or different;

$R^9$ is an alkyl group having 1 to 9 carbon atoms, cycloalkyl group having 3 to 12 carbon atoms, alkoxy group having 1 to 6 carbon atoms, aryl group having 6 to 10 carbon atoms, aryloxy group having 6 to 10 carbon atoms, amino group, heterocyclic group having a nitrogen atom as a hetero atom and bonded to a benzene ring by the nitrogen atom bonded to the benzene ring, or halogen atom, and q is an integer of 0 to 2;

when q is 2, the both substituents may be bonded together to form an alkylenedioxy group having 1 to 8 carbon atoms;

$R^{10}$ and $R^{11}$ are bonded together to form a group represented by the following formula (3):

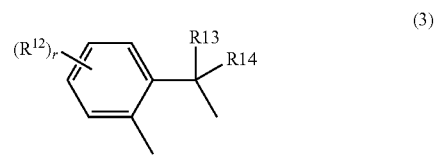

(3)

wherein $R^{12}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and r is an integer of 0 to 3;

$R^{13}$ and $R^{14}$ are each a hydrogen atom, hydroxyl group, alkyl group having 1 to 9 carbon atoms, cycloalkyl group having 3 to 12 carbon atoms, alkoxy group having 1 to 6 carbon atoms, halogenoalkyl group having 1 to 6 carbon atoms or halogenoalkoxy group having 1 to 6 carbon atoms, and further $R^{13}$ and $R^{14}$ may be bonded together to form a cyclic structure;

further $R^{10}$ and $R^{11}$ may be bonded together to form a group represented by the following formula (4):

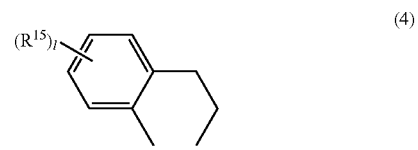

(4)

wherein $R^{15}$ is an alkyl group having 1 to 9 carbon atoms, cycloalkyl group having 3 to 12 carbon atoms, alkoxy group having 1 to 6 carbon atoms, aralkyl group having 7 to 11 carbon atoms, aralkoxy group having 7 to 11 carbon atoms, aryl group having 6 to 10 carbon atoms, aryloxy group having 6 to 10 carbon atoms, alkoxycarbonyl group having 2 to 7 carbon atoms, carboxyl group, amino group, heterocyclic group having a nitrogen atom as a hetero atom and bonded to a benzene ring by the nitrogen atom bonded to the benzene ring, cyano group, halogen atom, halogenoalkyl group having 1 to 6 carbon atoms or halogenoalkoxy group having 1 to 6 carbon atoms, and l is an integer of 0 to 3, wherein the polymer film is a film cured by the optical radical polymerization of the photochromic curable composition of claim 2.

18. A photochromic material comprising a polymer material and the chromene composition of claim 1 dispersed in the polymer material.

19. A photochromic optical product which comprises a polymer molded product containing the chromene composition of claim 1 dispersed therein.

20. An optical product which comprises an optical substrate covered with a polymer film containing the chromene composition of claim 1 dispersed therein.

* * * * *